US006207876B1

(12) United States Patent
Kellems et al.

(10) Patent No.: US 6,207,876 B1
(45) Date of Patent: Mar. 27, 2001

(54) ADENOSINE DEAMINASE DEFICIENT TRANSGENIC MICE AND METHODS FOR THE USE THEREOF

(75) Inventors: Rodney E. Kellems; Surjit K. Datta, both of Houston; Michael R. Blackburn, Pearland, all of TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/301,665

(22) Filed: Apr. 28, 1999

Related U.S. Application Data
(60) Provisional application No. 60/083,408, filed on Apr. 29, 1998, and provisional application No. 60/083,370, filed on Apr. 28, 1998.

(51) Int. Cl.$^7$ .............................. A01K 67/00; C12N 5/00
(52) U.S. Cl. ................................. 800/18; 800/9; 800/22; 435/320.1; 435/325; 435/455
(58) Field of Search .............................. 800/8, 9, 14, 13, 800/18, 3; 536/23.1; 435/320.1, 325, 455

(56) References Cited

U.S. PATENT DOCUMENTS 5,730,983   3/1998  Wegner et al. .................... 424/185.1

OTHER PUBLICATIONS

Abraham et al, "Animal models of asthma," In: *Asthma and Rhinitis*, Blackwell Ed., Inc, Boston, 961–977, 1995.
Arch and Newsholme, "The control of the metabolism and the hormonal role of adenosine," *Essays in Biochem* 14:82–123, 1978.
Azzawi et al, "Identification of activated T lymphocytes and eosinophils in bronchial biopsies in stable atopic asthma," *Am. Rev. Respir. Dis.* 142:1407–1413, 1990.
Barker, "Relation of fetal and infant growth to plasma fibrinogen and factor VII concentrations in adult life," *.B. M. J.*, 304:148–152, 1992.
Barnes, "Current Therapies for Asthma: Promise and Limitations," *Chest* 111:17S–26S, 1997.
Barnes, "A new approach to the treatment of asthma," *N. Engl. J. Med.* 321:1517–1527, 1989.
Barnes, "Pathophysiology of asthma," *Br. J. Clin. Pharmacol.* 42, 3–10, 1996.
Beasley et al, "Cellular events in the bronchi in mild asthma and after bronchial provocation," *Am. Rev. Respir. Dis.* 139:806–817, 1989.
Bellusci et al., "Involvement of sonic hedgehog (shh) in mouse embryonic lung growth and morphogenesis," *Development* 124:53–63, 1997.
Blackburn, and Kellems, "Regulation and function of adenosine deaminase in mice," in *Progress in Nucleic Acid Research and Molecular Biology*, W. E. Cohn and K. Moldave, eds., Academic Press, New York. vol. 55, pp 195–226, 1996.

Blackburn et al., "Adenosine–deaminase deficient mice using a two stage genetic engineering strategy exhibit a combined immunodeficiency," *J. Biol. Chem.*, 273:5093–5100, 1998.
Blackburn et al., "Metabolic and immunologic consequences of limited adenosine deaminase expression in mice," *J. Biol. Chem.*, 271:15203–15210, 1996.
Blackburn et al., "Adenosine levels in the postimplantation mouse uterus: Quantitation by HPLC–fluorometric detection and spatiotemporal regulation by 5'nucleotidase and adenosine deaminase," *Dev. Dynam.*, 194:155–168, 1992.
Blackburn et al., "Genetically engineered mice demonstrate that adenosine deaminase is essential for early postimplantation development," *Development* 124:3089–3097, 1997.
Blackburn et al., "Tissue–specific rescue suggests that placental adenosine deaminase is important for fetal development in mice," *J. Biol. Chem .*, 270:23891–23894, 1995.
Blaese, "Genetic immunodeficiency syndromes with defects in both T– and B–lymphocyte function," In: *The Metabolic and Molecular Basis of Inherited Disease.* (Scriver, C. R., Beaudet, A. L., Sly, W. S., and Valle, D., eds) vol. 3, pp. 3895–3909, McGraw–Hill, Inc., New York, 1995.
Blaese, "Development of gene therapy for immunodeficiency: adenosine deaminase deficiency," *Pediatr. Res.* 33:S49–S55, 1993.
Bollinger et al., "Brief report: hepatic dysfunction as a complication of adenosine deaminase deficiency," *N. Engl. J. Med.* 334:1367–1371, 1996.
Bordignon et al., "Gene therapy in peripheral blood lymphocytes and bone marrow for ADA immunodeficient patients," *Science* 270:470–475, 1995.
Bousquet et al., "Eosinophilic inflammation in asthma," *N. Engl. J. Med.* 323:1033–1039, 1990.
Bruns et al., "Adenosine receptor binding: structure–activity analysis generates extremely potent xanthine antagonists," *Proc. Natl. Acad. Sci. U.S.A.*, 80:2077–2080, 1983.
Bruns et al., "Allosteric enhancement of adenosine $A_1$ receptor binding and function by 2–amino–3–benzoylthiophenes," *Mol. Pharmacol.*, 38:939–949, 1990.
Bruns et al., "Characterization of the $A_2$ adenosine receptor labeled by [$^3$H]NECA in rat striatal membranes," *Mol. Pharmacol.*, 29:331–346, 1986.

(List continued on next page.)

*Primary Examiner*—John L. LeGuyader
*Assistant Examiner*—Sumesh Kaushal
(74) *Attorney, Agent, or Firm*—Fulbright Jaworski, LLP

(57) ABSTRACT

The present invention relates to the production of adenosine deaminase (ADA) deficient mice and the use of such mice as an animal model for dysfunctions associated with elevated adenosine levels. Also, provided by the present invention are methods of treating dysfunctions associated with elevated adenosine levels and methods of screening compounds for pharmaceutical activity in the treatment of dysfunctions associated with elevated adenosine levels.

15 Claims, 7 Drawing Sheets

OTHER PUBLICATIONS

Figure 2A:
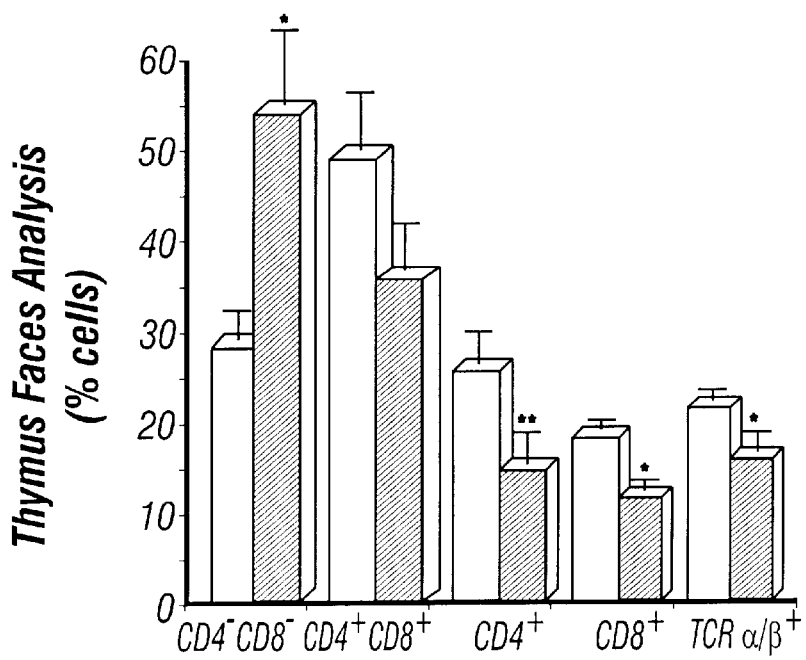

Brusselle et al., "Allergen–induced airway inflammation and bronchial responsiveness in wild–type and interleukin–4–deficient mice," *Am. J. Respir. Cell Mol. Biol.* 12:254–259, 1995.

Sears et al., "Relation between airway responsiveness and serum IgE in children with asthma and in apparently normal children," *N. Engl. J. Med.* 325:1067–1071, 1991.

Burrows et al., "The relationship of childhood respiratory illness to adult obstructive airway disease," *Am. Rev. Respir. Dis.* 115:751–760, 1977.

Busse et al., "Childhood–versus adult–onset asthma. NHLBI Workshop Summary," *Am. J. Respir. Crit. Care Med.* 151:1635–1639, 1995.

Cederbaum et al., "The chrondo–osseous dysplasia of adenosine deaminase deficiency with severe combined immunodeficiency" *J. Pediatr.* 89:737–742, 1976.

Cohen et al., "Deoxyadenosine triphosphate as a potentially toxic metabolite in adenosine deaminase deficiency," *Proc. Natl. Acad. Sci. USA* 75:472–476, 1978.

Colasurdo et al., "Airway hyperresponsiveness," In: *Asthma and Rhinitis,*. Blackwell Scientific Publications, Inc, Boston, 1044–1056, 1995.

Colasurdo et al., "Human respiratory syncytial virus produces prolonged alterations of neural control in airways of developing ferrets," *Am. J. Respir. Crit. Care Med.*, 157:1506–1511, 1998.

Colasurdo et al., "Human respiratory syncytial virus affects nonadrenergic noncholinergic inhibition in cotton rat airways," *Am. J. Physiol.* 268:L1006–L1011, 1995.

Colasurdo et al., "Maturation of the nonadrenergic noncholinergic inhibitory system in normal and allergen–sensitized rabbits," *Am. J. Physiol.* 267:L739–L744, 1994.

Coleman et al., "Identification and quantitation of adenine deoxynucleotides in erythrocytes of a patient with adenosine deaminase deficiency and severe combined immunodeficiency," *J. Biol. Chem.* 253:1619–1626, 1978.

Cushley et al., "Inhaled adenosine and guanosine on airway resistance in normal and asthmatic subjects," *Br. J. Clin. Pharmacol.* 15:161–165, 1983.

Cushley et al., "Adenosine–induced bronchoconstriction in asthma," *Am. Rev. Respir. Dis.*, 129:380–384, 1984.

Dixon et al., "Tissue distribution of adenosine receptor mRNAs in the rat," *Brit .J.Pharm.* 118:1461–1468, 1996.

Doherty et al., "Adenosine deaminase and thymocyte maturation," *Scand. J. Immunol.* 33:405–410, 1991.

Donofrio et al., "Overproduction of adenine deoxynucleosides and deoxynucleotides in adenosine deaminase deficiency with severe combined immunodeficiency," *J. Clin. Invest.* 62:884–887, 1978.

Dooley et al., "First trimester diagnosis of adenosine deaminase deficiency," *Prenat. Diagn.* 7:561–565, 1987.

Driver et al., "Adenosine in bronchoalveolar lavage fluid in asthma," *Am. Rev. Respir. Dis.* 148:91–97, 1993.

Dunwiddie and Fredholm, "Adenosine Neuromodulation," In: *Purinergic Approches in Experimental Therapeutics*, Eds., Jacobson, K. A. and Jarvis, Wiley–Liss Inc., New York, pp. 359–382, 1997.

Eggleston and Szefler, "Asthma in children," In: *Asthma and Rhinitis*, Blackwell Ed., 1380–1393, 1995.

Evans III et al., "National trends in morbidity and mortality of asthma in the US: prevalence, hospitalization rate and death from asthma over two decades (1965–1984)," *Chest* 91:65S–74S, 1987.

Feoktistov and Biaggioni, "Adenosine $A_{2b}$ Receptors Evoke Interleukin–8 Secretion in Human Mast Cells: An Enprofyllline–sensitive Mechanism with Implications for Asthma," *J. Clin. Invest.* 96:1979–1986, 1995.

Fink et al., "Molecular cloning of the rat $A_2$ adenosine receptor: selective co–expression with $D_2$ dopamine receptors in rat striatum", *Mol. Brain Res.* 14:186–195, 1992.

Gao et al., "Activation of apoptosis in early mouse embryos by 2'–deoxyadenosine exposure," *Teratology* 49:1–12, 1994.

Gergen et al., "National survey of prevalence of asthma among children in the United States (1976–1980)," *Pediatrics* 81:1–7, 1988.

Gleich, "The eosinophil and bronchial asthma: current understanding," *J. Allergy Clin. Immunol.*, 85:422–436, 1990.

Glezen and Denny, "Epidemiology of acute lower respiratory disease in children," *N. Engl. J. Med.* 288:498–505, 1973.

Godding et al., "Adhesion of activated eosinophils to respiratory epithelial cells is enhanced by tumor necrosis factor–α and interleukin–1β," *Am. J. Respir. Cell. Mol. Biol.* 13:555–562, 1995.

Gonzalo et al., "Mouse eotaxin expression parallels eosinophils accumulation during allergic inflammation but it is not restricted to a Th2–type response," *Immunity.* 4:1–14, 1996.

Hall, "Respiratory Syncytial Virus," In: *Textbook of Pediatric Infectious Disease*, RD Feigin and JD Cherry, Saunders Ed., 1653–1676, 1992.

Hall, "Prospects for respiratory syncytial virus vaccine," *Science* 265:1393–1394, 1994.

Hershfield.and Mitchell, "Immunodeficiency diseases caused by adenosine deaminase deficiency and purine nucleoside phosphorylase deficiency," In: *The Metabolic and Molecular Basis of Inherited Disease*. (McGraw–Hill, Inc., New York) 1:1725–1768, 1995.

Hershfield, "Apparent suicide inactivation of human lymphoblast S–adenosyl–homocysteine hydrolase by 2'–deoxyadenosine and adenine arabinoside," *J. Biol. Chem.* 254:22–25, 1979.

Hirschhorn, "Overview of biochemical abnormalities and molecular genetics of adenosine deaminase deiciency," *Pediatr. Res.* 33:S35–S41, 1993.

Hershfield et al., "In vivo inactivation of erythrocyte s–adenosylhomocysteine hydrolase by 2'–deoxyadenosine in adenosine deaminase–deficient patients," *J. Clin. Invest.* 63:807–811, 1979.

Horn et al., "Total eosinophil counts in the management of bronchial asthma," *N. Engl. J. Med.* 292:1152–1155, 1975.

Jackson, "Renal action of purines," In: *Purinergic Approches in Experimental Therapeutics*, Eds., Jacobson, K. A. and Jarvis, M. F. Wiley–Liss Inc., New York, pp. 217–250, 1997.

Jacobson et al.,"Electorphilic derivatives of purines as irreversible inhibitors of $A_1$ adenosine receptors," *J. Med. Chem.*, 32:1043–1051, 1989.

Janusz et al., Functional activity of the adenosine binding enhancer, PD 81,723, in the in vitro hippocampal slice, *Brain Research*, 567:181–187, 1991.

Jarvis et al., [$^3$H]CGS 21680, A selective $A_2$ adenosine receptor agonist directly labels $A_2$ receptors in rat brain, *J. Pharma. Exp. Therap.*, 251:888–893, 1989.

Kaminska and Fox, "Decreased S–adenosylhomocysteine hydrolase in inborn errors of purine metabolism," *J. Lab. Clin. Med.* 96:141–147, 1980.

Knudsen et al., "Ontogeny of adenosine deaminase in the mouse decidua and placenta: immunolocalization and embryo transfer studies," *Biol. Reprod.* 44:171–184, 1991.

Knudsen et al., "Effects of (R)–deoxycoformycin (pentostatin) on intrauterine nucleoside catabolism and embryo viability in the pregnant mouse," *Teratology* 45:91–103, 1992.

Kohno et al., "Activation of $A_3$ adenosine receptors on human eosinophils elevates intercellular calcium," *Blood* 88:3569–3574, 1996.

Kung et al., "Mast cells modulate allergic pulmonary eosinophilia in mice," *Am. J. Respir. Cell Mol. Biol.* 12:404–409, 1995.

Laitinen et al., "Damage of the airway epithelium and bronchial reactivity in patients with asthma[1–3]," *Am. Rev. Respir. Dis.* 131:599–606, 1985.

Ledent et al., "Aggressiveness, hypoalgesia and high blood pressure in mice lacking the adenosine $A_{2a}$ receptor," *Nature* 388:674–678, 1997.

Lee et al., "Interleukin–5 expression in the lung epithelium of transgenic mice leads to pulmonary changes pathognomonic of asthma," *J. Exp. Med.*, 185:2143–2156, 1997.

Lilly et al., "Expression of eotaxin by human lung epithelial cells: induction by cytokines and inhibition by glucocorticoids," *J. Clin Invest*, 99:1767–1773, 1997.

Linden, "Structure and function of $A_1$ adenosine receptors," *FASEB* 5:2668–2676, 1991.

Long et al., "Sequelae of respiratory syncytial virus infections," *Am. J. Respir. Crit. Care Med.* 151:1678–1681, 1995.

Mann et al., "Airway effects of purine nucleosides and nucleotides and release with bronchial provocation in asthma," *J. Appl. Physiol.* 61:1667–1676, 1986.

Marquardt, "Adenosine," In: *Asthma*. vol. 1. eds., Barnes, P. J., Grunstein, M. M., Leff, A. R. and Woolcock, A. J. Lippincott–Raven, Philadelphia, PA.pp. 585–591, 1997.

Marquardt et al., "Adenosine release from stimulated mast cells," *Proc. Ntl. Acad. Sci.* 81:6192–6196, 1984.

Marquardt et al., "Potentiation of mast cell mediator release by adenosine," *J. Immunol.* 120:871–878, 1978.

Martinez, "Viral infections and the development of asthma," *Am. J. Respir. Crit. Care Med.* 151:1644–1648, 1995.

Mattoli et al., "Eotaxin expression and eosinophilic inflammation in asthma," *Biochem. Biophys. Res. Commun.* 236:299–301, 1997.

Mentzer et al., "Release of adenosine by hypoxic canine lung tissue and its possible role in pulmonary circulation," *Am. J. Physiol.* 229:1625–1631, 1975.

Migchielsen et al. "Adenosine–deaminase–deficient mice die perinatally and exhibit liver–cell degeneration, atelectasis and small intestine cell death," *Nature Genet.* 10:279–287, 1995.

Morgan et al., "Heterogeneity of biochemical, clinical and immunological parameters in severe combined immunodeficiency due to adenosine deaminase deficiency," *Clin. Exp. Immunol.* 70:491–499, 1987.

Nadel and Holtzman, "Regulation of airway responsiveness and secretion: role of inflammation," In: Asthma: physiology, immunopathology, and treatment eds., Kay, A. B., Austen, K. F. and Lichtenstein, L. M. Academic Press, London, pp 129–155, 1984.

Najar et al., "Adenosine and its derivatives control human monocyte differentiation into highly accessory cells versus macrophages," *J. Leuk. Biol.* 47:429–439, 1990.

Nakajima et al., "CD4[+] T–lymphocytes and interleukin–5 mediate antigen–induced eosinophil infiltration into the mouse trachea," *Am. Rev. Respir. Dis.* 146:374–377, 1992.

National Heart, Lung, and Blood Institute National asthma Education Program. "Expert Panel report: guidelines for the diagnosis and management of asthma," *J. All. Clin. Immunol.* 88:425–534, 1991.

Nyce and Metzger, "DNA antisense therapy for asthma in an animal model," *Nature* 385:721–725, 1997.

Olah and Stiles, "Adenosine receptor subtypes: characterization and therapeutic regulation," *Ann. Rev. Pharmacol. .Tox.* 35:581–606, 1995.

Olsson, "Local factors regulating cardiac and skeletal muscle blood flow," *Ann. Rev. Physiol.*, 43:385–395, 1981.

Pierce et al., "Molecular cloning and expression of an adenosine A2b receptor from human brain," *BBRC* 187:86–93, 1992.

Ratech et al., "Pathologic findings in adenosine–deaminase–deficient severe combined immunodeficiency: I. Kidney, adrenal and chondro–osseous tissue alteration," *Am. J. Pathol.* 120:157–169, 1985.

Ratter et al., "S–adenosylhomocysteine as a physiological modulator of Apo–1–mediated apoptosis," *Int. Immunol.* 8:1139–1147, 1996.

Renz et al., "Aerosolized antigen exposure without adjuvant causes increased IgE production and increased airway responsiveness in the mouse," *J. All. Clin. Immunol.* 89:1127–1138, 1992.

Richardson, "Blocking adenosine with antisense," *Nature* 385:684–685, 1997.

Rothenberg et al., "Targeted disruption of the chemokine eotaxin partially reduces antigen–induced tissue eosinophilia," *J .Exp. Med.* 185:785–790, 1997.

Salvatore et al., "Molecular cloning and characterization of the human $A_3$ adenosine receptor," *Proc. Natl. Acad. Sci. USA* 90:10365–10369, 1993.

Schutz et al., "Different sites of adenosine formation in the heart," *Am. J. Physiol* 240:H963–970, 1981.

Schwarze et al., "Respiratory syncytial virus infection results in airway hyperresponsiveness and enhanced airway sensitization to allergen," *J. Clin. Invest.* 100:226–233, 1997.

Burrows et al., "Association of asthma with serum IgE levels and skin test reactivity to allergens," *N. Engl. J. Med.* 320:271–277, 1989.

Seto et al., Mechanism of deoxyadenosine and 2–chlorodeoxyadenosine toxicity to nondividing human lymphocytes, *J. Clin. Invest.* 75:377–383, 1985.

Shi et al., "Diverse regulatory motifs required for murine adenosine deaminase gene expression in the placenta," *J. Biol. Chem.* 272:2334–2341, 1997.

Shijubo et al., "Eosinophilic cationic protein in chronic eosinophilic pneumonia and eosinophilic granuloma," *Chest*, 106:1481–1486, 1994.

Sigurs et al., "Asthma and immunoglobulin E antibodies after respiratory syncytial virus bronchiolitis: a prospective cohort study with matched controls," *Pediatrics* 95:500–505, 1995.

Stehle et al., "Molecular cloning and expression of the cDNA for a novel $A_2$–adenosine receptor subtype," *Mol. Endocrinol.* 6:384–393, 1992.

Strek and Leff, "Eosinophils," In: *Asthma*. vol. 1. eds., Barnes, P. J., Grunstein, M. M., Leff, A. R. and Woolcock, A. J. Lippincott–Raven, Philadelphia, PA.pp. 399–417, 1997.

Stiles, "Adenosine receptors," *J. Biol. Chem.* 267:6451–6454, 1992.

Tang et al., "Targeted expression of IL-11 in the murine airway causes lymphocytic inflammation, bronchial remodeling and airways obstruction," *J. Clin. Invest.* 98:2845–2853, 1996.

Teran et al., "Eosinophil recruitment following allergen challenge is associated with the release of the chemokine RANTES into asthmatic airways," *J. Immunol.*, 157:1806–1812, 1996.

Ullman et al., "A biochemical genetic study of the role of specific nucleoside kinases in deoxyadenosine phosphorylation by cultured human cells," *J. Biol. Chem.* 256:848–852, 1981.

Van Calker et al., "Adenosine regulates via two different types of receptors, the accumulation of cyclic AMP in cultured brain cells," *J. Neurochem.*, 33:999–1005, 1979.

Vogel, "New clues to asthma therapies," *Science*, 276:1643–1646, 1997.

Wakamiya et al., Disruption of the adenosine deaminase gene causes hepatocellular impairment and perinatal impairment in mice, *Proc. Natl. Acad. Sci. USA* 92:3673–3677, 1995.

Walker, "Effects of adenosine on guinea pig pulmonary eosinophils," *Inflamm.* 20:11–21, 1996.

Wan et al., "Bindings of the adenosine $A_2$ receptor ligand [$^3$H]CGS 21680 to human and rat brain: Evidence for multiple affinity sites," *J. Neurochem.*, 55:1763–1771, 1990.

Wardlaw et al., "Eosinophils and mast cells in bronchoalveolar lavage in subjects with mild asthma," *Am. Rev. Respir. Dis.* 137:62–69, 1988.

Weiss et al., "The relationship of respiratory infections in early childhood to the occurrence of increased levels of bronchial responsiveness and atopy[1–4]," *Am. Rev. Respir. Dis.* 131:573–578, 1985.

Wiginton et al, "Complete sequence and structure of the gene for human adenosine deaminase," *Biochemistry*, 25 (25):8234–8244, 1986.

Winston et al., "5' flanking sequences of the murine adenosine deaminase gene direct expression of a reporter gene to specific prenatal and postnatal tissues in transgenic mice," *J. Biol. Chem.*, 267:13472–13479, 1992.

Zhang et al., "Influence of the route of allergen administration and genetic background on the murine allergic pulmonary response," *Am. J. Respir. Crit. Care Med.* 155:661–669, 1997.

Zhou et al., "Molecular cloning and characterization of an adenosine receptor: the A3 adenosine receptor," *Proc. Ntl. Acad. Sci. USA*, 89:7432–7436, 1992.

Wall. Theriogenology 45:57–68, 1996.*

Cameron Mol. Biotech. 7:253–265, 1997.*

Blackburn et al, J. Bio. Chem. 270(41):23891–23894, 1995.*

Blackburn et al, J Biol Chem 271(25):15203–15210, 1996.*

Winston et al, J Biol Chem. 267(19):13472–9, 1992.*

Blackburn et al. J. Bio. Chem. 270(41):23891–23894, 1995.*

Shi et al. J. Bio. Chem. 272(4):2334–2341, 1997.*

Blackburn et al. J. Bio. Chem. 271(25):15203–15210, 1996.*

* cited by examiner

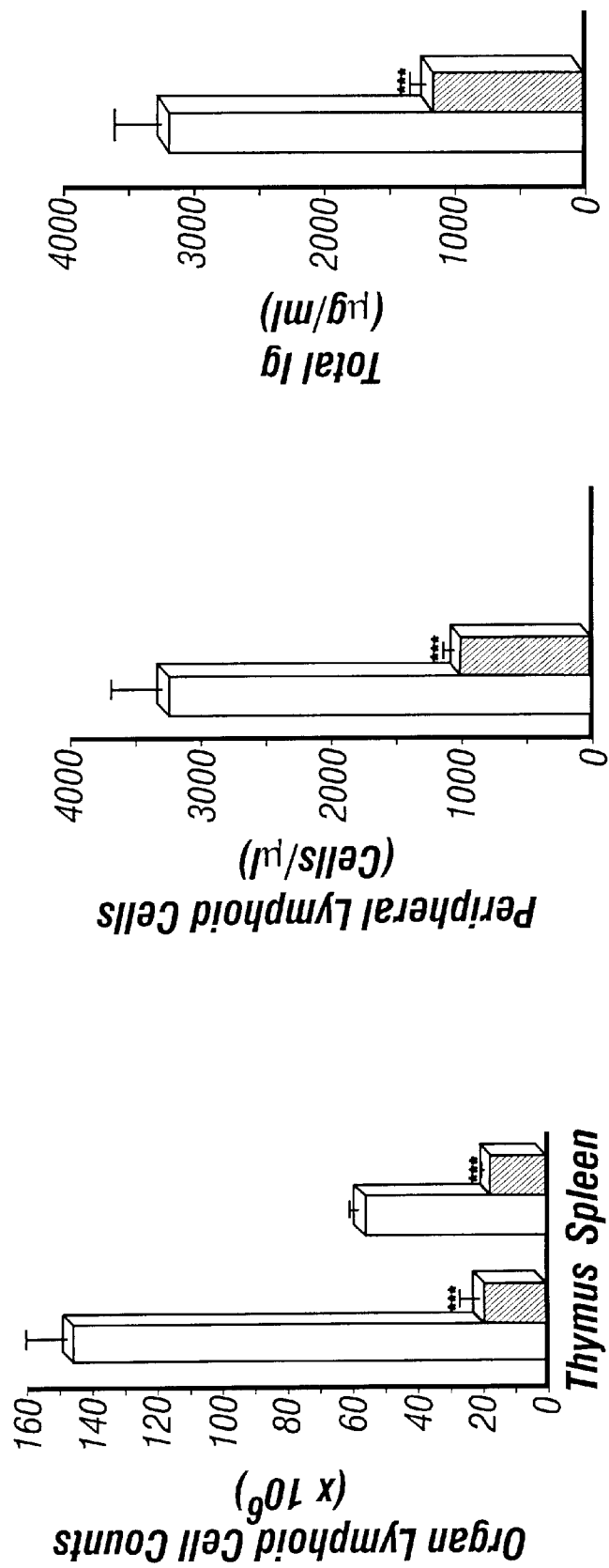

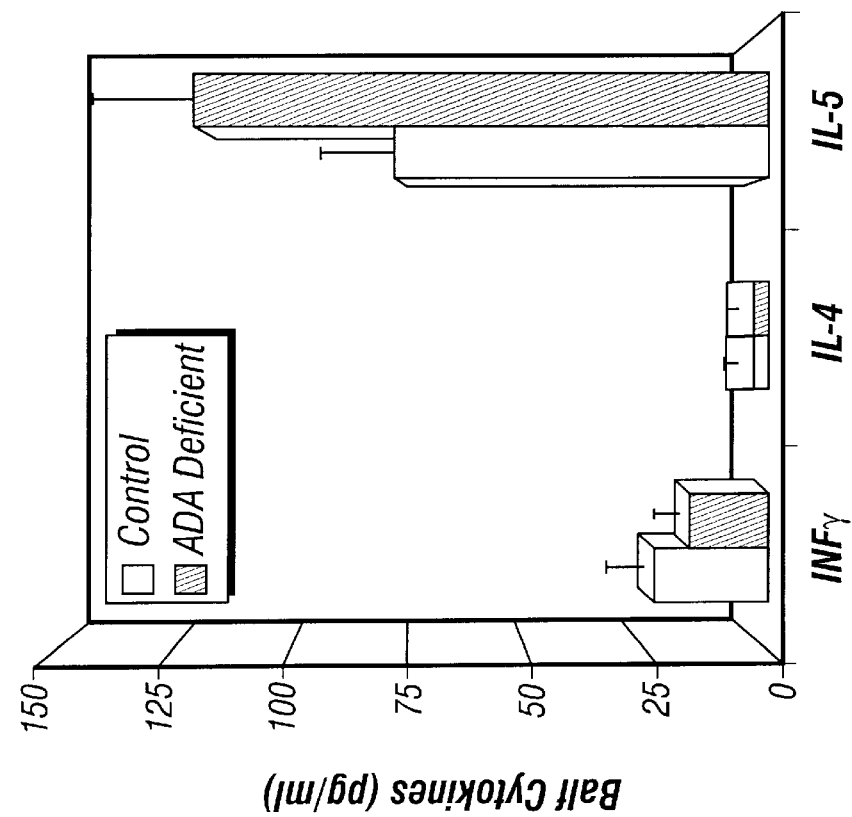
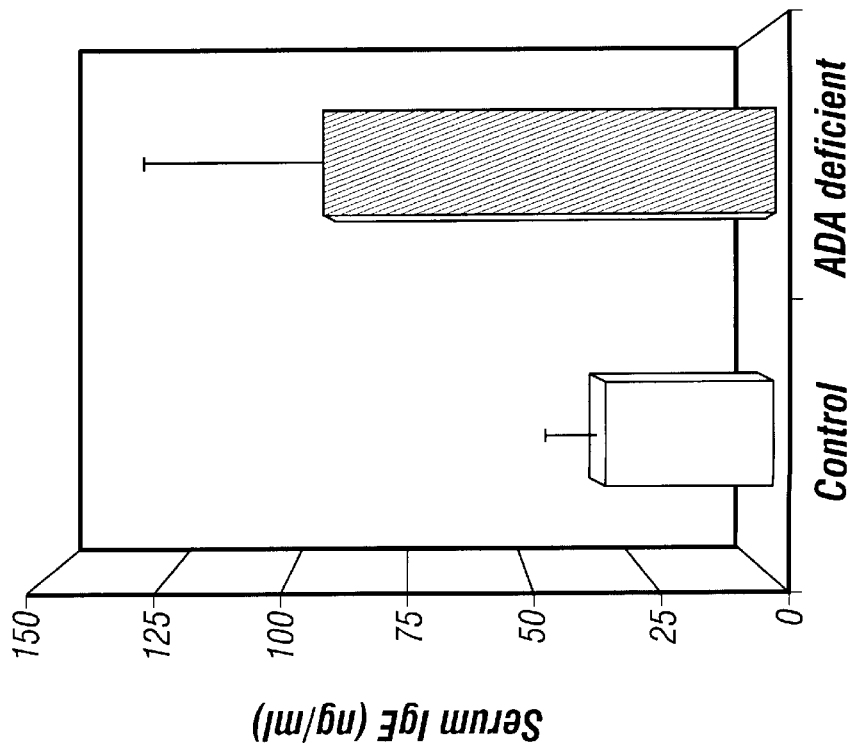
FIG. 6B
FIG. 6A

SEQUENCE LISTING

<160> NUMBER OF SEQ ID NOS: 4

<210> SEQ ID NO 1
<211> LENGTH: 1379
<212> TYPE: DNA
<213> ORGANISM: Mus musculus

<400> SEQUENCE: 1
cgaccctgcc agcgagccaa cgcagaccca gagagcttcg gcggagagaa ccgggaacac      60

-continued

```
gctcggaacc atggcccaga cacccgcatt caacaaaccc aaagtagagt tacacgtcca    120
cctggatgga gccatcaagc cagaaaccat cttatacttt ggcaagaaga gaggcatcgc    180
cctcccggca gatacagtgg aggagctgcg caacattatc ggcatggaca gcccctctc    240 gctcccaggc ttcctggcca agtttgacta ctacatgcct gtgattgcgg ctgcagaga    300 ggccatcaag aggatcgcct acgagtttgt ggagatgaag gcaaggagg gcgtggtcta    360 tgtggaagtg cgctatagcc cacacctgct ggccaattcc aaggtggacc caatgccctg    420
gaaccagact gaaggggacg tcacccctga tgacgttgtg gatcttgtga accagggcct    480
gcaggaggga gagcaagcat tggcatcaa ggtccggtcc attctgtgct gcatgcgcca    540
ccagcccagc tggtcccttg aggtgttgga gctgtgtaag aagtacaatc agaagaccgt    600
ggtggctatg gacttggctg gggatgagac cattgaagga agtagcctct cccaggcca    660 cgtggaagcc tatgagggcg cagtaaagaa tggcattcat cggaccgtcc acgctggcga    720
ggtgggctct cctgaggttg tgcgtgaggc tgtggacatc ctcaagacag agagggtggg    780
acatggttat cacaccatcg aggatgaagc tctctacaac agactactga agaaaaacat    840
gcactttgag gtctgcccct ggtccagcta cctcacaggc gcctgggatc ccaaaacgac    900
gcatgcggtt gttcgcttca agaatgataa ggccaactac tcactcaaca cagacgaccc    960
cctcatcttc aagtccacc tagacactga ctaccagatg accaagaaag acatgggctt    1020
cactgaggag gagttcaagc gactgaacat caacgcagcg aagtcaagct tcctcccaga    1080
ggaagagaag aaggaacttc tggaacggct ctacagagaa taccaatagc caccacagac    1140
tgacgggcgg gtcccctgaa gatggcaagg ccacttctct gagcctcatc ctgtggataa    1200
agtctttaca actctgacat attgaccttc attccttcca gaccttggag aggccaggtc    1260
tgtcctctga ttggatatcc tggctaggtc ccaggggact tgacaatcat gcacatgaat    1320
tgaaaacctt ccttctaaag ctaaaattat ggtgttcaat aaagcagctg gtgactggt    1379
```

<210> SEQ ID NO 2
<211> LENGTH: 352
<212> TYPE: PRT
<213> ORGANISM: Mus musculus

<400> SEQUENCE: 2

```
Met Ala Gln Thr Pro Ala Phe Asn Lys Pro Lys Val Glu Leu His Val
 1               5                  10                  15

His Leu Asp Gly Ala Ile Lys Pro Glu Thr Ile Leu Tyr Phe Gly Lys
            20                  25                  30

Lys Arg Gly Ile Ala Leu Pro Ala Asp Thr Val Glu Glu Leu Arg Asn
        35                  40                  45

Ile Ile Gly Met Asp Lys Pro Leu Ser Leu Pro Gly Phe Leu Ala Lys
    50                  55                  60

Phe Asp Tyr Tyr Met Pro Val Ile Ala Gly Cys Arg Glu Ala Ile Lys
65                  70                  75                  80

Arg Ile Ala Tyr Glu Phe Val Glu Met Lys Ala Lys Glu Gly Val Val
                85                  90                  95

Tyr Val Glu Val Arg Tyr Ser Pro His Leu Leu Ala Asn Ser Lys Val
            100                 105                 110

Asp Pro Met Pro Trp Asn Gln Thr Glu Gly Asp Val Thr Pro Asp Asp
        115                 120                 125

Val Val Asp Leu Val Asn Gln Gly Leu Gln Glu Gly Glu Gln Ala Phe
    130                 135                 140
```

-continued

```
Gly Ile Lys Val Arg Ser Ile Leu Cys Cys Met Arg His Gln Pro Ser
145                 150                 155                 160

Trp Ser Leu Glu Val Leu Glu Leu Cys Lys Lys Tyr Asn Gln Lys Thr
                165                 170                 175

Val Val Ala Met Asp Leu Ala Gly Asp Glu Thr Ile Glu Gly Ser Ser
            180                 185                 190

Leu Phe Pro Gly His Val Glu Ala Tyr Glu Gly Ala Val Lys Asn Gly
        195                 200                 205

Ile His Arg Thr Val His Ala Gly Glu Val Gly Ser Pro Glu Val Val
    210                 215                 220

Arg Glu Ala Val Asp Ile Leu Lys Thr Glu Arg Val Gly His Gly Tyr
225                 230                 235                 240

His Thr Ile Glu Asp Glu Ala Leu Tyr Asn Arg Leu Leu Lys Glu Asn
                245                 250                 255

Met His Phe Glu Val Cys Pro Trp Ser Ser Tyr Leu Thr Gly Ala Trp
            260                 265                 270

Asp Pro Lys Thr Thr His Ala Val Val Arg Phe Lys Asn Asp Lys Ala
        275                 280                 285

Asn Tyr Ser Leu Asn Thr Asp Asp Pro Leu Ile Phe Lys Ser Thr Leu
    290                 295                 300

Asp Thr Asp Tyr Gln Met Thr Lys Lys Asp Met Gly Phe Thr Glu Glu
305                 310                 315                 320

Glu Phe Lys Arg Leu Asn Ile Asn Ala Ala Lys Ser Ser Phe Leu Pro
                325                 330                 335

Glu Glu Glu Lys Lys Glu Leu Leu Glu Arg Leu Tyr Arg Glu Tyr Gln
            340                 345                 350

<210> SEQ ID NO 3
<211> LENGTH: 36741
<212> TYPE: DNA
<213> ORGANISM: Homo sapiens

<400> SEQUENCE: 3
gatctgggta aagggttttc caggtgtcag gatggaagtg actaaggtgc agaggctgga      60
gggctggggc aggtagaagc aagcattcct gttacctact gctgtgtgac aatctccccc     120
taaaacacaa tggcttaaaa taacatccat ttcattacat atctcaatac tataggtcag     180
gaatttgggc tgggcttact tgggtaattc ttctgtccca catggcattg accaaagcct     240
ggttttcagt gggcagctgg gctggatggc ccaacacagc ttcgctaaca tgattgctgt     300
cttcgtaggg atggtggaag cctgggctca gtgggactgt caactggaat ggccatatgt     360
ggactctctt agcatgatgg tctcttctag aagcttgggt cccagagag aatgttcaag      420 aggccccaaa ggacaccaca aagcttcttt atgaccaagg ctcggaaatc aggaagctt      480 gctcccatca cgctctatta ctccaacaag tcactcaggc cagcccaggt ccaagaggag     540
gaaacctaga ctccatcttg caatgtgaag aattgcaaat aatttgtgtc accctttaagc    600 aaccagcaac tcatctaggt tgattggcat ttcagcaatg tggtgggaag tggtgggact     660
gatgttgaag agggacttga atgtcatgag aggctgggga ggcaataagg tgggagtga     720 agtttctcga gtcagattca aatttaaacc ccagttttgc cacttacaac ccatgagcca     780
agcaggctgt ctctctatct gaacctcagt gtcctcatct gtaaaatgag gagaacacct     840
cctacatctg aggatgactg taaagatgaa atgggatggg tgcttataaa gtgcttccca     900
gtgtacctgg ctccaaacct gtctcagtaa atggcagccc ctattattga acccgagtaa     960
```

-continued

```
cacagagagc caagaaagga tcttacaaaa aactcccctg gctttgacaa tgtatgagac    1020
ccactgatag ggtttggctt tgtgtcctca cccaaatctc atctagtagc tcccataatt    1080
cctacatgtt gtgggagaga ctcggcggga gataattgaa tcatgggggga tggtctttcc   1140 catgctgttc ttgtgatagt aaataagtct cacaagatct gatggtttta aaaatgggag    1200
tttccctgca ggcgctctct ctttgtctac tgccatccat gtaagacgtg acttgctcct    1260
cctttgcctt ctgccatgat tgcaaggcct ccccaccatt gtggaactgt aagtctatta    1320
aagcctcttt cttttgtaaa ttacccagtc tcaggtatgt cttttttttt ttttcatga    1380 gatggagttt cgctcttgtt gcccaggctg gaatgcaatg gtgtaatctt ggctcaccac    1440
aacctccacc tcccaggttc aagcgattct cctgcctcag cctcccgagt agctgggatt    1500
acagtcatac accaccacgc ctggctaatt ttgtattttt ttttttttt ttagtagaga    1560 cggggtttca ccatgttggt caggctggtc tcaaactccc gacctcaggt gatcctcctg    1620
ccttggcctc ccaaagtcct gggattacag gcatgaacca ctgcgcccag gctcgggtat    1680
gtcttcatca gtagcatgaa aataatggac taatacagcc accctctccc tcactcccac    1740
atacaaccaa accccaaatc cagctgattt tacaccctaa atgcagcttg aatatgagtt    1800
tctccacttc ccccactgac atcactatgc cctacccaga ccatggcagt tgcctccttc    1860
ctggtatcct gtcctccctc accccgctg gcccctgta atgccctccc ctcacagcag    1920
ggagcccagg cttctcaaag tgccctgtgg gtgcgaacca cctggggtc ctgtttgtat    1980 aaaatacaga ttctacttca gtaggtctgg gatgggtct gaaagtctgc atttgtagtc    2040
agctcccagg tgatgtgggt gctgatgatc cctggatcac actttcagta gctggagaat    2100
attttttcca aataaaaggg tgattttgtc tcgcctccac ttaaaacact ccactgactt    2160
cctaggaatc ccacaccatc gctgggtccc acatccctgg caggattcag ctcccatcag    2220
accttctagc cccttgctct ccactctccc actctctctt tccccttgt ttatgggttt    2280 gttaatttat ttatgatgaa atgaaatgaa gctaccatcc accccagtac tggaacatta    2340
tcaataacct gtgtgtggcc aggcgtggtg gctcatgcct gtaatcacgc cttgggaagc    2400
cgaggtgggt ggatcatgtg aggtcaggtg ttcgagacca gcctggccaa catggtgaaa    2460
ccccgtctct actacaaatc caaaacttag cagggcacgg tgccacgcgc ctgtaatccc    2520
agctactcgg gacgctgagg ccgagaactg cttaaaatcc aggaggtgga ggttgcagtg    2580
agccgagatt tcgccactgc actccagcct gggcgacaga gcaagagtcc atctcaaaaa    2640
aacaaaaaca aaacaaaaa aacaaaaaac aaaaattagc caggcgtggt tgtgggcgcc    2700
tataatccca gctactcggg aggctgagac aggaaaatcg cttgaaacgc tggggtgcg    2760 gggggcggt ggggaggagg cgggccagag gggcagaggt tgcagtgagc ccagatcgcg    2820
ccacttcact gcagcctccg cgaaagagcg aaactccgtc tcagtaaata aataaataaa    2880
taaataaata aataaataaa taacctgtac ccgcgtgtta tttccctccg tccttacctc    2940
ctcccggctc cttcccttc acctgagata accactcttc tcgtatctat gctcatcttt    3000
cccttgcttt acattttttc caccgatgca tgtgtctaaa catacatact tttggttttg    3060
cttttacaca ttctaaaagt tgcaccattg tatgcagttt tccgcaactt agtttttttc    3120
actcaacatt gtttctgaga cattgtttct gttgttgtct ggctgaagtt cattccgttt    3180
cactgctgtc taacgtttca tggtgtgaat attccggttt atttgcccac tcgcccgtgg    3240 agggggcattt gagggtgttt ccaatgttcc tgttattcgg aatagcgctg gtgtgaacat    3300
tctgcacagg tctctggctg cgcctgggcg ggtttcttaa aggtgaatgc ccaggagggg    3360
```

-continued

```
actgtctgtg ttctccctcc ctccgagctc cagccttcct cgcctccttt cactcccagc    3420
tccctggagt ctctcacgta gaatgtcctc tccaccccca cccacccctg atgaactcct    3480
gcaggttctg caggccacgg ctggccccc  tcgaaagttc cttaactata caattatggt    3540
gtgtgtttct gcgacgagcg tccgtctatc cggtggaagg cacgccgctc gaggcttgcg    3600
atgctcccgg ggtccccgct tctagcttgg gcctggcgca cagcagcgcc cagactgcag    3660
ggggacgctt gaaagttgct ggaggagccg gggggaaggc agcgcccagc gaggcggctg    3720
gagcgcgcgc ccacaggtgg gtccggtcgg gcgccgcggg gccgtagttt tcgggtcggc    3780
gggcgaggac gccgggtcca gaattccagg aaatgcgcga tccaggccgg cgggcggggc    3840
gggggctccg gcgagagggc gggccccggg aacggcggcg ggcggggcgg gaggcggggc    3900
ccggcccgtt aagaagagcg tggccggccg cggccaccgc tggccccagg gaaagccgag    3960
cggccaccga gccggcagag acccaccgag cggcggcgga gggagcagcg ccggggcgca    4020
cgagggcacc atggcccaga cgcccgcctt cgacaagccc aaagtgagcg cgcgcggggg    4080
ctccggggac ggggtccgg  cgcctgggcg gcccgagggg cttagcgggg cccagcccgg    4140
ggcgtccaaa ccctgggaac gaacgggggc tcctgcaggc gagttcttcc ttcggcttag    4200
gccgtggctt gcttgcgggc taatcaggga caatggggca gagaaggtcc agaacccgga    4260
ggcctccaga gtctgcttct gcccctgact tgaccctct  gggtctcagt ttcgctgtct    4320
gtcaagtggg catcctagca ccgctgagcg ctgtgtgggc ctgggcaggg acttgaggtc    4380
tctgaagctc agctgtatga tcaggcccga tgtctacgcc ggatagcgac ctagtgctgt    4440
gccccgcgcc tactgagtgc tcagtgaatg gaagcagctt tgtacgccag cgttatggtg    4500
gtgagcgcca aggagctcag gtttgtggat gcgccccggg gaagaaccgt gagccctgcc    4560
agaaagggga gggaggggag cagagcaccc cccttccccc gcgcgggaag aacaggagct    4620
aggtaggccc tgggtttggg gccctagcag ggttcactcg aggccaagcc atgcccact     4680
ggccccaggg gagaatcccc ttgtttctcc gcccaccagc tgtggcgtct tgggactgtt    4740
ggggtcaggg agggtctgga cccccttggc ctgtctcaga gtccgagagg aggggcccag    4800
gagtctgcca agcaggtgga gtcagccagt agggtgtgag agtggttggg gaaggagtca    4860
gctgcagtca gcctcaactt acccttctaa gaaataggtg tgagtggccc aggaggttgg    4920
ctcacgcctg taatcccagc actttgtgag gctgaggcgg gaggatcatt tgagtccagg    4980
agtttgagac tagcctggac aacaaaacta gaccccgtct ctccaaaaaa taaaaaaagt    5040
taggggaagt gtgtgtggtg gtgcactccc gtagtcccag ctactcagga ggctgaggcg    5100
ggaggatcgc ttgagcccag gaggttgagg ctgcagtgag gtgtgatggt gccactgacc    5160
ttcagcctgg gagacagagc gagaccctgt ctcaaaaaaa aagagaagaa aagaaaaga    5220
aaagaaatag gtgtgaatga tgatgacagc tatcacaaaa gtgccggtga gaatccagtg    5280
agtgtgcatg tgtcagtgag ggagacaggc tgtggagagc ccacctacct tctgaggagg    5340
gtgaggcctg gccccactag ctgatgcccc cagcccaggg aaaatgctca gctactcccc    5400
gtcagaagct ggaacgactg aggtgctgta caagccctcc tacccccacc cctgcctcct    5460
tcacgtctta ctggagctgg ggcccatgat tggcgcctcc cctttgcagt cttttttatta    5520
aatgctctgg gctccctctg cccttgggct ggggacccac tgtaccctga tgtgaatcct    5580
atggcagtag caaagctctt tgattggcgg ggtgcagtgg ctcacgcctg taatcccagc    5640
actttgggag gcaaaggtgg gtggatcatg aggccaggag ttcgagacca gcctggccaa    5700
```

```
catggcaaaa cccatttct actaaaaata caaaaaatta gctgggcatg gtgcgggcgc   5760
ctgtagtccc acgtacgcag aaggctgagg caggagaatg gcataaaccc gggaggtgga   5820
gcttgcagtg agccgagatc tcgccattgc actccagcct gggtgacaga gtgagactct   5880
gtctcaaaaa aaaaaaaaaa aaaaaaagg ctccttgatt gcgaacatgt tgggagttat   5940
ggagagaaca gcagggccca cttctagagc acttgttgca gacacccatt ggatccttgc   6000
agttcttctg taacagccca tcaagggagg ggctcatatt attatcccca ttttttggcc   6060
ttgctcagtc ctcccatctg attcaagctg gcagatcatt ttccctattg ggacctcagt   6120
gtccacacct ggaggatgga acatcagctg cttatgtggg tgtcccgtgt cctgagtccc   6180
aaggccacaa ggtgatgctt gagagtaagg gtagaatgtt acctgccatg tgtttgaggc   6240
gtgacaaatc ttgtatgatt gtgaggagga acttgtgtga gctggcagga aagtgggaa   6300
ggagtgtgaa tctcagagcc actgtgacca gagccagctc cctgccctct tgtgggaggg   6360
acagatgaca gttataatta ttagcattac tagctgcagc taatggagtg ttgatgtttc   6420
tgccaggcac cgttctaaac acattatctg cattttttat ttaatccagg cacagagagg   6480
ttaactaggc ccaagatcac acagctagga aatgtccaac tctggggttt gagtccaagg   6540
gaggctggct tcgaaatccc atgcctctaa ccatctttcc taaactacct ctgcagaagc   6600
ctttggggat agaggtgcca gtgccccagg tgcaaacctc ctgagacagg agcctttgct   6660
gtgtccttca gcttctcata cctgccacca gctgaggcct gggacctggt cagctagaag   6720
aaagcagagc agggcagcgc ttttcaaact gcactcaagt ggcctgactt ttaatgttca   6780
cactgtgatt ctgtgtgggt cgggttgggg cctgcgatgc tgcactgctg accagctccc   6840
aggaaatgct aatgtcaacg atccaggaac acactttgct tagcaaggcc ctaggcagct   6900
gccttctgtt gtgcgggacc cctattgact ccaatggata tagcaccagg ttcaagaggc   6960
taccttcttt ggaagaggta gcaaacaaga tacgggtttt tactggggc ttagacacag   7020
ggaagagagt ccagtggcgg cagactgagc agaagaaccg caaccacttg caaatcatgc   7080
agtttatgta gcattttcat ttaacaccttc ctcccaacca tctccaccta gtaaccttca   7140
tttaacccaa acaaagggc ctcggtccct ataccctgt atggtcagtg tcccgtggga   7200
atggggtggg gctcagatgt tcctcataga taacgactgg atctccaggt tggccactct   7260
tggattcctt cgctcagaac tctgaacacc cattcaagtg tgcctgccat gcagggtcat   7320
cgtcagggga tgcccaagtc aagtttgcct gtcgggtgtg cctcccatac ccccacctgg   7380
tttgacttag cacctgctgg gcactggaag aagtgcaaag gggggttgca ggggtggccc   7440
ttatcagcct atgttcacag gtggcaccag gcactcaggc attctgcatc ctggaggcca   7500
gtgctgatca catgcctgtt acaataatca taacaatagc tgtccttgaa gtagtcctgg   7560
gtaccaggtg ccttcagtga ctttttcttc tttgccagaa tctcactctg tcgcccaagc   7620
tggagtgcag tggcaagatt ttgggtccct gcaacctctg cctcctgggt tcatgcgatc   7680
ctcctgcctc agcctcccaa gtagctggga ctacaggcgt gtgccgcagt ctcactctgt   7740
tgcccaggct ggagtgcagt ggtgtgatcc tggctcacta caacctccac ctcccgagtt   7800
caagccattc ttctgcctca gcctccggag tagctgggat tacaggcgtc caccaccacg   7860
cccggctaat ttttgtattt ttagtagaga cagggtttca ccacgttagc cagctggtct   7920
cgaactcctg atctcaggtg atcctcccac cttggcttcc caaagcgctg ggattacagg   7980
tgtgagccac tgtgccggc tagtaacttt tatctcacgg aatcctctgg acgacttgac   8040
aaggcatggg tcttcatccc catttacaga tgaagaaact gaagcttagg gagtggaggg   8100
```

-continued

```
acttgccagg gctacacaaa atctgagagc cttgaagctg tagactggca agtgaacagg    8160
tacaggctgg gacagcagtt tctttctttt tttcttttt tagacagagt ttcgctcttg     8220
ttgcccaggc tggagtgcaa tggcacgacc tcggctcact gcaaccttcg cctcccaggt    8280
tcaagtgatt cttctgcctc agcctcccaa gtagctggaa ttacaggcat gcaccaccat    8340
gcccggctaa ttttttgtat ttttagtaga cgggtttt ctccttgttg gccaggctgg      8400
tctcgaactc ccgacttcag gtgatccgcc cacctcagcc tcccaaagtg ccggattac     8460 aggcatgagc caccgcaccc ggccaaggga cagcagtttc taaactgtcc ctctctgatg    8520
cagaggggaa ttgggctaa atcagcaatg tgccttttct gtctcatatt tgaatgtcta     8580
ctctgcacga ggcgctgtcc tgctttgcat acagtgactc atttaatgtt tatgtcagcc    8640
ctctgaggaa ggtcctgtcc tattattaac ttcacttatt atgaggaaac tgagactcag    8700
agaggggagg gaacttgcca aagtcacaca gctggcaagc agcagagcta gacttgaacc    8760
cagatctgcc tgcactcaag tagaagctgt tcattgcttt gctcatttgc caattccact    8820
ttatgcaaaa aagaggggc agtgtggggg gaagagttag aatcagggtg gcagggtggg     8880
ccagtgcatt agccctgggc ttcagatgta ctggggttga attcctgcct gccgcttagc    8940
agctagggta cctcaggtag acaactcctg aaactcagct tcccctctg taaaatgggg     9000 tgacaaaacc aagatcttgg ggttcttggg gaaactgaca tgctgattgg ttttgtaca    9060 gtgcctggct ggtaacagca ggccctcagg ggtgcgtttc cttcctgggg actggagtgg    9120
gggttgcagt agactctggg aggcctctcc agctgcagaa tctccctcct ccctcctcct   9180
ttttgtcttc ctgacacaaa acccaccagc tgcacttctt tgggcttgca gtggctttca    9240
gttaccagag ccacctgtta aaacaaaaat gtgcctagga agagcctgcc ttacccattt   9300
tgactcacat ggcagttggt ggtggagggg aacaaaggag actgagtttc atcgaagcct    9360
tttgcttcgg aggaggaagg gaggatcaga gagaggaagt ggtctgtgtt cacacaggga    9420
ggcaggggag gccaggcagc ttcccaatcc tgcattcaac ctcagggtgg gcttgacctg    9480
ggtggctggg ggccctgtga tccaggagag acttgtccac ctgctcaggt gtcttgaagg    9540
ggtccctgtg gtacccctg ggcggggcaa ggtagtagga ccatggtctg gctggggagg     9600
tggagaggag caggctgtgg gcgcagagtg aggttggaat ctgtatttac ccaaggtgtt    9660
gggggtaggc ttgccctcag cccttaatgt tctcaggccc ctgagcagtt gtggggata     9720 acctctgcac tcctagtgac cagggagcta gaacagcaag gaatttgaac ttggacacca    9780 gctgggtca ggctctctgg gtctgagtcc tgatttccca ctttccagct agaggagctt     9840
gaatgagtca tttaacttca cggtgcctca gtttcccctc tctaaaatga gaattatacc    9900
catacccacc tctcaaacac caagtgcagg cctggctcag agcaggtgct gcagcaatag    9960
ctgccattgg tcagcatcat catcatggtt ggtaatggtc ctactttgac ttttgagaca   10020
gagtctcact ctgtcgccca ggctggagtg cagtggtgca atctcggctc actacaacct   10080
ctgctcccgg gttcaagtga ttcttctgcc tcagtctccc aagtagttgg gattacaggt   10140
gtgcgccacc atgcctggct aattttttgtg ttttagtag acagggtt tcaccatgtt     10200 ggccataaca atgctgtcc ttgaagtagt cctgggtacc aggtgccttc agtgactttt    10260
tttttttttt tttttttgag ctggagtctt cctctgtcac ccaagctgga gtgcagtggc   10320
acgattttgg ctcactgcaa cctctgcctc ctgggttcat gcgatcctcc tgcctcagcc   10380
tcccaagtag ctgggacttg ggatacactt gccccgctg gtcctccctt ccacctctgt    10440
```

-continued

```
gaagaggagg tctcaaactc ctggcctcaa gtgatccacc cacctcagcc tcccaaagtg     10500
ctgggatttc aagagtgagc caccgcacct ggccctgtt tagatgttag catcagtgac      10560
ccagcacctt gctatgtggc atgcagggag cgtgctgcta gacctccggg tttagagtca     10620
aatagcttcc tggctgtggt gtgcattaga ctttctaact caaggtcctc ccactctctg     10680
agcctcagtc ttgttgcctt taaaacgagt ttaagtgtgc tgagtcccta tgctgtggct     10740
ccacaggaat ttccccaggt ggaagacaca tcttgccttc tgtgaaacct ctcagcagca     10800
gagctgtcag gccccgtcag caggagacac tgtgggact gctcagtccc ttccactgtg      10860
tacctcggag ctggcggagc ctagatgagg ctgagcatag agggcttcct ggaggaagtg     10920
gagctgaaac agtttctcag cccagggctg ctctgtctcc tggcctcaca ctaaaagtca     10980
gttgagaggc catagtggca taagtcactg accctggcac tgcccagctc atcaccaaaa     11040
gcagggctag ggagggaggg gacattcgat tggcagtggg cacctgtggc tcatctgggt     11100
tctggccacg gtgctcaggt tctgtgagct gaccaggcag ccctggctcc tctgccccg      11160 tgtgggttct gccaggtccc atggggcagg tcagcccctt ccttgttgca gggagagcac     11220
ccagcattgc tgacatggga cagggaaacg aggaaataac ggtgtggtca ttgaacacag     11280
agagcactag gtgctgtgcg aggtgctgag gacacgacat gatgacacag acaaggtccc     11340
ccctctcagc aaacggctca tgaggagac agacatgtta catacatgaa cccaaaaagt      11400
cagacgaaaa caaaacagag cgatgtgttt gggaggcaaa cccaactgcc ggagggcgag     11460
cagttgggaa cgtggaaaca tgagtcagat ctggagtat ctgtcccagg agtccaagac      11520
ctgggtcctc atggtagctc tgccaccgac acactgagtg accttgggta agtgaaccca     11580
ccgccctgga cctctctggc acgcatctct tgagagcagg gacttagtgc atttcccgag     11640
ggcctccacg gtgcctggca catagtgggg cttagtaaat atttgttggt aactgaggat     11700
gcttcctgtt cacatcagcg ctgggaggat ttcctgctgt tcagacaaat gctgggctgg     11760
ctgtgagtca gccttgcaga gagcaaaggc agtgggaagg ggcgtgagat tcccctctgg     11820
agaggtcagg aggccaggca ctgtctcgac atgagtgcca gggagggggt gtggcctgtg     11880
ggcagggctt gggctgaggc agagggactt gagttccacc ctagctctac caccatcaat     11940
tttgtgtaac tctggacagg ccactgaact tctccgggct tagcctggca agtccatttc     12000
cccatctgta acatgggccg atatgtacat tgcctaggga ttaaatgaga taaagggtct     12060
gaaaacagta ggtagctgct ttatcattat tattatttct gtattattga tgtctgaggc     12120
taggcccaca gaggcagtac agtagagtgg ttaggagctc aagaatcaga ctagggttca     12180
aattctgact ccatcactga ctgtttttggg gtacttctttt gaacctcagt ttcttcatca    12240
gtaaaatggg agtgaagtct ctaccttgct ggttgtaagg atgaaataag ataatgcata     12300
tagatggtct agcacatagt agatactcaa aagtttgagg ccactgctga ccctttcccc     12360
tgaaaggaga caggagagcg gggtcgccac cccattgtca ttgtcatctg aataggctg      12420 acagacttcc catggtgtgt tgcagttttc tagaaaattc agtaggaggc ctgcctgagc     12480
ttgagccacc tgtggaggtg cttcctgcct ctgctccaca cctgaaacgc gtctgggcct    12540
cttctcaggc agccgtgaga agggatgagt gctactggtc atggtgggca gctggctctg    12600 cttttccccct tcccagaggc gctcctgcct cctgcccagc tccctgaacc cctagcttct    12660
gcaccccggc actgtctggc ttctgccccg ctgagcaccc actgtctctg acgctgcctt     12720
gagtacttcc cgcatgttat tcaaatccca atcagatctt ccctcccca gtagctggtc      12780 ttctgttctg gcttcctgcc atcctgtcct ccacacagca gccgggaaag gttttttttaa   12840
```

```
agggggactct ccgatttaac acacttgggt ggaaaaccct ttgcttcggc ctctgcaatc  12900
tccctgcccc ctctccactt tgccctggcc tcatttctca ccactaacct cactctgcac  12960
tctggccaac tccccgcctg cttcctgatt cagacactaa gcacacgcag ctcccctgcc  13020
tggagccatt ctccctctcc ttctttcttc tccctggaga actccccctt taagtgatct  13080
tttcccaaca cactttctaa attgcccccca ccccagtgtg attttttcttt atctcatagc  13140
acttggtctg cttcttatca cagtttgcaa ggctgagttc agaaaggtgt gtttgctcat  13200
tctgaggcag gagaggctac cttgtgctgc tgtggtaaca acagccccc aggtctgagg  13260
ggtctgcaga gacccaggtt gacctcatac tgcttgtccc tccagggcct ccagtgaggt  13320
ttcggctcct tggatcactc agggccccag gcagatggga agattccact ctgaacattg  13380
ccaattgttg tgccagagta aagcagagct gggaggtggg ctcttgaatt ggcatttaaa  13440
tacttttgcc aggcagggta aggcagctca cgcctgtaat cataacactt tgggaggcct  13500
aggtgggtgg atcacctgag gtcaggagtt caaaaccagc ctggccaaca tggtgaaacc  13560
ctgtctctac taaaagtaca aaaattagcc gggcatggtg tgggcgcct gtaatcccag  13620
ctacttggga ggctgaggca cgagaatccc ttgaacctgg gaggcagagg ctgcaatgag  13680
ctgagatctt gccactgcac tccagcctgg gcaacagagc cagactccat ctcaaaaaaa  13740
aaaaaacaac aacaacaaat aaataaatga ataaatactt tagccagaag tagccatgca  13800
gacctcccccc caccagtccc acccacaagc ggacgtgact accgccccca ttcactgcct  13860
gatcctcctg ttctcagggg ctccaaggcc aggcctggtt tgaccttctg actttctgac  13920
ttcctcctac cttcccagta acctcatgca actcctttca ctcagcctca atcatcccca  13980
tgggtgttta aacttgccca agacatgccc ctttgaaaaa gcctgccatt ctcttgaccc  14040
acatgcacgt cctgcccccct ccaaggctgc tagttccttt aggggcaaaa ttgtgaaaga  14100
gtagtctaaa ccttcttcct cttcttacct ccacttcttt cttaccttat tcccatgtgg  14160
attctaccct cactcaggcc tctagaacgg ttcctctacg gcagtggttc ccaatcttga  14220
ctacgtgttt ttttaaaaaa agtcctccac ctgggcctgc caccaaggat ttttctttaa  14280
ttgacctcag atgggggttga ggccttggga actggccaga acttcccgtg ctcctaactt  14340
gcagccgggg ttaagaacta ctcctctgaa gcccccagtg cctgcgcttt tagcccgacg  14400
gacaagtttc tgcccttcca tcctgtgacc tccagcaggg cctgaccatg tgagttttct  14460
gtggctgccg tgacaagttg ccacaccctg catggcttca accaacagaa acgtgtgccc  14520
tggcagttct gggggccaga agtccaacat caagatatca tcagagccac atgcccactg  14580
aaggctctcg ggggaatcca ttccttgcct cttctggttg ctggtggctc taggcattcc  14640
ttggcttgtg gctgcatcat tccagtctct gcctctgagg tcacgttgct gcttcctctt  14700
gtgtgtgttt ctcttaaaac tctctgcttc tgtcttataa ggatacatgt gattgcatct  14760
agggcccaac cagataatcc aggataaact cttcctgtca agacatttaa taatcacact  14820
tgccatata aggtaatttt ttttttttt tgaggtggag ttttgcactt tcacccaggc  14880
tggagtaaag tgatttaatc tcggctcact ggaatctctg cccccaggtt caagcaattc  14940
tcctgcctca gcctcctgag tagctgggat tataggtacc tgccaccatg cccagctaac  15000
ttttgtattt ttagtagaca tggggtttca ccatgttggc caggctggtc tcgaactcct  15060
gacctcaggt gatccacccg ccataagtta atatttttt tttgagaggg agtattgctc  15120
tgttgcccag gctggagtgc tagtggctca atctcggctc actgcaacct ccgcctccca  15180
```

-continued

```
ggttcaaatg attctcctac ctcagtctcc tgagtagctg ggactacaga tgcatgccac    15240
catgcctggc tgattttttgt attttttaata gagaggggat ttcaccatgt tggccaggct   15300
ggtgttgaac tcctaacctc aagtgatcca cccacctcag cctcccaaag tgttgggatt    15360
acaggcatga accaccacgc ccgacccata taaggtaata tttacaggtt ctgggggatta   15420 ggattagcat gtagacagct ttgtgggggc caccattcag cccactatgc taaccctgtg    15480
aaccgttgct cgcttctcct tgacatctga cggcctggcc ttctgcatac cacacaccct    15540
cccacctctc tggccacagt tctgtaggct cagcctcctc cgtaaggcca ttaagtgctt    15600
gtgctggtca aagtttcatc ctaggccttt tccttacctc ccttgatatt ttctccctag    15660
gtgagctcct tcaagcccac agcttctgtg cttacccaca ctcctaccta cattcccagc    15720
ttgggcttct caggccagct ctagactctt gtatcccact gggttcttcc acttaccttt    15780
ggatatctca aaggcatctc cagttggctg ggcacgatgg ttcacacctg taaccccagc    15840
actttgggag gccgaggtgg gcagatcact tgaggtcagg agttcaagac cagcctggcc    15900
aatatggtga aaccccatct ctactaaaaa tacaaaaatt agctgggcat ggtggtgggt    15960
gcctgtagtc ccaactactc gggaggctga ggcaggagaa tcgcttgaac ccgggaggtg    16020
gaggtttccg tgagctgagc tggagccact gcactccagc ctgggcaaca gagtgaaact    16080
ccgtcttaaa aaacaaaaa acaaaaggtg tctctagtgt aacataacta aaaccaaacc     16140
aatcatgcct ccctcccccg catcctccct cctggaggga gctccaggac ttggtcttct    16200
cttccagagt tctctgtctc aaactgcggg aattgctccc cacccaggcc taacctgaag    16260
tgtgagcctt ggcatctctt tctatccacc tgtttttcct ctatgcacct cacaaccctg    16320
gtccaagcca ccgtcatctt tcaaatggct gcagtagcct ctaactggcc ttggaggagc    16380
catcctcttt ctctaaccag ctgccaaccc tgcaatggcc tctgtgtgct ttccagataa    16440
agcctgactc ctcgtggccc gcacagccct gcctgggtgg tcctatcctg cagcctctcc    16500
agtaccatga accctccctt ctctgaacct ctatttaatc catttcatat accccgtttt    16560
ctcctgccat agggccttgc acatgctgtt ccttctgcct ggaattttct tcctgcctcc    16620
ctccgcaccc ctgccttgtg ttgtgggttc ctcgctatcc tctagctttt cgctcaggct    16680
cattgttggc cctctagatg tattcacttc tcttgtttgt tacctctgt cataggactg     16740 tgttcgtact tcccaaggag tcgtcttggt ttgtgactgt acattttccc atgtgacatt    16800
tgcttaatgc ctctcccact ctggggcctg tacaagcccc aggaacagga cttgaccct     16860 cctgtttaac tctacaatct agcatccagc aggcgcgcag gccttcgttg acttttatt     16920 tattcttatt ttttattttt gagatgcagt ttcgctcttg tcgcccaggc tggagtgcag    16980
tggcgtaatc tcggctcact gcagcctctg cctcccaggt tcaggtgatt ctcctgtctc    17040
agcctcccaa gtagctggga ttacaggtgt gcgccaccac gcctggctaa ttttttgcat    17100
ttttagtaga gatgggggttt caccatgttg gccaggctgg tctcaaactc ctggcctcag   17160
gtgatccacc cacctcggcc tcccaaagtg gctggattac aggggtgagc ccccatgccc    17220
agccttcatt gactttagt tgacaactat ttagcatttg ctatgtgcca agaactccct     17280
gcctactaat gcagttaacc ctcatgaagc ctagaaggaa ggactgccat tctcccact    17340 taacagatga ggatgccgag gcacaggaag tgaagtgact ttctcagggt caagcaggga   17400
gtgagtggag gagccgagat tccagctcta accgcatgat gctctataca gtgtgactcc    17460
ggctctctgg ctgggccctc tccatagccc tgtgagggtt aaggatagaa aacagaggct    17520
cagagagttg aggtcccttg cctgaggtca cacagctggt tggccgttcc ctgggctata   17580
```

```
agcttcagta ttcccaatgc tgagcatatt ttgagaaccc gagaaacaga cgtttggctg   17640
ggtgggaact gaactcattt tgtcagggaa ttcaacaact aagttggccc tgagactggg   17700
tgtgaagacc gctctgtccc ctgccagctg atgacctca ggagagatct gatgactctg    17760
aggtcctgct gataggacct ctggtgtctc tgttccctgc tggcctcccc tgggcctggg   17820
ttgggtttcc tctgcaggag gcagctcatg tatgtgctcc tagacgccct tgggccagca   17880
gctccttggc tgttcctccc tgagccaggg cagccaactt tcttatccag ctctccatgc   17940
tccccacccc agcatgagat gtcagctgag agttttctgg atctccccta gctaggggga   18000
aagcttccat catttggaac aggaacagca ggaacagcaa agtccctttc cccaccatct   18060
cccactgcct gctgtgcttc tcctaacagc tcatggtaaa caccctgact gagcggcagg   18120
ggctgtttcc tttgggctat ccatgtccac ctacactgcc ctttttaatc cttacaattt   18180
ttcttggaca cggggcata atattccatt gtttttcagt tgaggaaact gaggctcaga    18240
gaggtcaagt gtcttgtctg aggtcacaca gcagaactgg gagtcaagcc agatgggctg   18300
cctccaagga tcctactctt aaactctaga gtactagaaa gatcttccgt tgcctaatat   18360
tgattcctga taggctatgc ttgagtagca tctgcttttg aaaatggagc ctgggtcggt   18420
tgcggtggca catacctgta atcccagcac tttgggaggc tgaggtgggt ggacacctga   18480
ggtcaggagt tcgagactag cctgagcaac atggtgaaac cctgtctcta ctaaaaatac   18540
aaaaattaac tgggtgtggt ggcacctgcc tatagtccca gctactccgg aggctgaggc   18600
acaagaattg cttaacccca ggaggtggag gttgcagtga gaggagatca cgtcactgca   18660
ctccagcctg ggagacagag cgagactcca tccgtctcaa aaaaaagaaa acgaaaatgg   18720
atcctgaatt ttgaaatatg ctgtgactct tccctagttt gggacatctg ggtcaatccc   18780
ttttgttaaa gtagtttatt tagttggctg agagcgggag ctgcctacgt gacctggagc   18840
acaagctttg gaattgggct tgggttagaa ttccgcctct gccactcacc agctgcgatt   18900
aagaacaaag atactgggtt gggctcctgc ctctattact tgcaatctgt gtggccttgg   18960
atgagatatt taacacctcc gaacctcagt gtcctcaatt gtgaaagaga tcgagataac   19020
agctgaaccc acatcccagg agcggattaa atgagatagt gcagtacaga gtttaccgaa   19080
gtatatgggg tcagcagcca gccagtaaaa tggtggctaa tggttatcat gattaatgtt   19140
aacattaagc tctgaaaggt ccttcgtgaa ctcataggta tttgttctct ctctcccttt   19200
ctctctctct tcccccctgcc cccttgcagg tagaactgca tgtccaccta gacggatcca   19260
tcaagcctga aaccatctta tactatggca ggtaagtcca tacagaagag ccctctctcc   19320
ctgggatttg agtggggtcc ccagctccac ccagaggccc ctggggaatt ccaggggtcac  19380 tgttccttcc tgtctccctg tgggaatcaa gccagctcca ggccagaagt gggactgtga   19440
ggacatggag gcctcggcac tgagctgcag acccgcagac caactcctga gctttctggg   19500
cctctgagtc ttgtcctcct ggtgtcaggt gagccaggcc tgagcctgct ctccccaccc   19560
acccacatac gtgcatgaag gtagttccca gggctgaatc cgtctttttt tttttctttt   19620
gagatagagt cttgctctgt cgcccaggct ggagtgcagt ggcatgatct cggctcactg   19680
caacctccac ctcctgggtt caagtgattc tcctgcctca gcctcctgag tagctgggat   19740
tacaagcaca tgccaccaca tccagctaat ttttgtattt ttagcggaga tggggtttca   19800
catgttggcc aggctggtct cgaactcctg acctcaagtg atccacccag cttggcctcc   19860
cacagtgctg ggattacagg catgagccac tgtgcctggc tcctgtcttt tgacttaact   19920
```

```
gagagcctat atatagcagg tgatgtgctc acatgagatg ccagtacaat ttcttgagca    19980
tctcctagag ctgggctggg ctttatcagc tcattgaatt cctccacgct tggaagagga    20040
ggatacgctc tctgcatttt actgaggagg gaatgggctc agccaagaca gttgtccacg    20100
gtcacacaaa ttaatagcag atcaagagtt gaacccaagg ctgtctgacc cctaaggctt    20160
tactacatca tcagggtcat aacctgctag gagtcacgga aaagtggctc cccaactctg    20220
ggcctaaatc tctgcatctt ccaagtgaga acacacttcc tgcctcagct ctcagagatg    20280
ctagggggcc agagggtccc cctgttcccc agcgaggaag gttcttccct tcctacccag    20340
acctcaaggg ctcacagcag ctcctctctt aggaccagct tttaagggca gggactttaa    20400
aggccagtgg atctggattc aaatttggac atattatctc ctgtctgcga acttggtctc    20460
tatcaactga ggctaagaac aggccctccc tagagagatg acctaggagc tagggctcc    20520 ttgtccaccc agccctgccc ccgcagacct gtgttcctcg gatgtttgca caacactcat    20580
tttgtttgga gctgaaagaa ctcagcctct ctgtcacagt cttgaaattc agctcgggac    20640
ccaaatttga acatttctgc tccataagcc agaatcctgt tattcagagg cctgccctca    20700
tggagagaat gagggatccc gggggttgcc cccaactctc gggagcatct ccaccaactc    20760
cctgagagat ttctggtaag tccactattc tccatctttt cacacttcca gggaccttct    20820
tctgccccag gaagctgcca ttgatttaat tcctatttaa ctgcaaggca taagcacagt    20880
agcacctcct gtgtgccaaa cactccttta agtgcgttac ccgggttaag ttattgaagc    20940
ctcacaacaa tttgtaagat aggaactcta ttgccgtcat ttacagatga ggagactgag    21000
ccgtggtagg tggagtaagg tgcccagtaa gcacagggcg gaggtttgaa cccagatagt    21060 ctgccccga gtccatggcc ctggccatta cccctgtca gttagaggtt ttggtaagtg    21120
atgcccgtaa aatgcttagt tcagggccta gcacacatta atgtgctcca taaatgtcac    21180
ttaatgataa tattcttatt aattggagct tatatctcta agtggggtga aacctcttgg    21240
cttatctctg cctggccttt gcccatgtca agccgccaac ttgccacaag gcccctaatg    21300
aggtcgttca gtggggcacc aagatgagat cgaacccagg cactcattaa ggggtcacgg    21360
agggctcatc agctgcagcc aggggctggg agcgccgggt ggggctaaga gaaagggaa    21420 aggagccgcc gggaggggca ctggtctgat cgtccattcc tcacaccacc tctgggcctt    21480
ggagatggcg tgcggcaggt gccagctgga gcttggcctg aagtcagcag gcagggact    21540 ggggagtttg tcacactcag atatgggtgt ctgtaaatgc acacaaatat gggctaagaa    21600
tggaaggagg aggggagccc ctggcctgag ccctgctagg cccaattcag tggcccttt    21660 tccagctctg ggactcaggc ctgcctcatt aactgtcctc acccatttct ccttcctcca    21720
gttcccagga ttctggcctt tcaggggcc tctccaacct ctttctcagt cttgtttata    21780
accctgtcaa ctatttctac agagattctg aaactggctg ctctttcctc cgatcactgc    21840
cctggtctgg gccaccactg cccctccctg tgctgtggc ctcctgattg gtctcagcca    21900
tctactctgg ccttcctctc tacgggccct gcagtgctgt agttggagca agagccttaa    21960
cccatggtct tcccagctca ttccccagct tccccatctc actcagagtc aaagccaaag    22020
tccacacatg ggccttaaag ttctgcaaag cctgcattgc ctctctgacc tctctaaggc    22080
tccttgctta gtccacactg gatgtttttc aaacatgcca gacctaggaa acagagagtc    22140
tgggttactt gccaaggtc acacagcctt aagtcacag agctgggatt caaacccaga    22200
ccactgggct tcagagtctg ctctttctca tgacacacaa agtttcattt cttcctctgt    22260 gcaccccctac atggaaaata ttatgtttta ctgacaaggg caccaagggc cttagagggg    22320
```

-continued

```
agcgctcctg cctgggatga tgtggtaaat aggggtggga gatggacttg acctgcaacc   22380
cctgcgctca tcctccctcc ctccctgggc tcctgatggt gggcttcttg tgactgtgtt   22440
gcccaccaag gccggaagag gaccagacag tgccccagca cagcagctgt ggctgaccag   22500
ggagtaggga tcatctaaga acagagcgtg catggtgctc acgcctgtaa tcccagcact   22560
ttgggaggcc aaggcgggtg gatcacctga ggtcaggagt tcaagaccag cgtggccaac   22620
atgggaaacc ccgtgtctac taaacataca aaaaattagc caggcatggt ggtgggcatc   22680
tataatccca gctacttgag aggctgaggc aggagaatca cttgaaccag ggaggtgaag   22740
gttgcagtga gtcgaggtcg tgccattgca ctccagcctg ggcaacaaga gcaagactcc   22800
gtctcaaaaa aacaaaacaa aagaaaaaac agagggtggc cctatgagga gccttcgctt   22860
gtgtgggtgg ccagggacag caagaggtgc cagggcccta ggaacagctc tttcctgctt   22920
caactttggg ctccagatgg gcgctttcca gctcagtctg agcagcttcg ggaagctgtg   22980
tcccatggga gacactggga gtccctgtg ctctttgtct cctgtcgggc ccccacatta   23040
gctctctggc ctcagctctg gcttccctcc aatttgtttc ccacgcagca gccagaggag   23100 cttcaaaaa ggtaaattat ttcatgctag tccctgctt gaaatcctac agtgccttcc   23160
cagtgctttc agccaaagcc ccagtccctt cctaagccca gctggccct gcctccctgg   23220 tgcatcatct gcacaaatgc ctgctctctg acctccagcc accctgcact tccaatgccc   23280
gcggcttcct gcctgcagct ttagtacaga cccctcccct gcccagaact gcccccaccc   23340
caaggcttct gctgaaatgt cacctcctca gagaggcctt ccctggctgc tctgtctaaa   23400
ctctgtgttg agaagttcct tcttgatggt tgttgaggag ggaggctgga gaagaagaat   23460
caaagaggag aaatagaaag caaaataatt tgttcttggg gacgggctgg tgctgggcac   23520
ggggaggcgc ccgtctctgg tgtgggcagc tgggtagatg gaggagccgt atttggaaat   23580
gtggaaccca ggaagggagt gatctagagg gaggggaaag gtggcgcgag atgcctgcct   23640
ctcaacaggt agccagacac atgggtctgt cttggtcact gctatctgcc cagtgcccag   23700
cacatcacag gccctcagtg gtggtgtgtg ggcatagaga attagaagct gtggacctct   23760
ggatccggag ctgaaaacca ccaaaggaga tgagttggcc tggccaggtg tgtaaaaggc   23820
agagtctgag agagaacgac cagagggcag agccccgcag gtggagtcct gggggctgga   23880
gggagaccat taggagaatc gcacatggct ggcgcagcag gtcccaggca aatgtggcca   23940 ctgggttttgg caatatggga gccagagccc tagtgtcatc tccctgcctt ctacccagca   24000
gttcccagag tgatatcccc aacagtgttt gacaactggt acaggctctt cagcggccac   24060
agttactggg caaggccttg tgagggtgac tttggggcag ctggccagca gtgggagggg   24120
aagcagtctc aggggtacct gaggcactga gctccgacct ccaggtgcca atgccgcacc   24180
agggcaccgt tccctgcag gctcttacag ggattagggg ctggtaagga gcagtgatta   24240
ggggctgact agcaggctgg tgggcaccag catgaccct tggtggtacc ctctgggcac   24300
tcatggggac ttgggctaac agatggggaa gggagcacat tcaggggct taggaaacat   24360 atttatgtag ggaagcattt taatatttta gtaacagaag ctattaaagg acttacaaac   24420
ttacttacat acactaaaac actatttggt caaacttctg tttcttggc acttttcctcc   24480 tttattcttt tttatttttt tgagacaggg tcttgctctg tcacccaagc tggagtgcag   24540
tggtgcaatc ttggcccgca gtagccttga cttccaggct caggtggtcc tcccacctta   24600
gcctcccaag tagctgggac tacaggtgca cgccaccacg cctggtgaat ttttgttttg   24660
```

```
aaggggtttc actgtgttgc ccaggctggt ttcaaactcc tgggcttaag tgatccgcca    24720
gccttggctt cccaaagtac tgtgattaca ggtatgagcc actgcacccg gcctcctatt    24780
tttctgcttc tgctttgtgg ataattggat gcttggacct cctgatttaa tcttctaatt    24840
tccttaactg tttactccta tttttcatca tcttgtcttt ttgttctact ttgtggagga    24900
tttcttcact tttagcttcc agttcttttc ttacatcgtg acagttgctg ccgcattctc    24960
ttgtaaattt ccgagggctc gttcttgggt tctgaatgtt ccctcctttc aaggatcttc    25020
tcatctcttt gaggatattc atgtcttttt tgttttggtt cttaggtttt catctgttct    25080
ctgtgctgtt tcctcggagt gcttttgtct attctgttgt tttgtccctc atgttagaag    25140
catttctttt ttttttcttt ttttttttgt gatacagagt cttgctctgt caccaggctg    25200
gagtgcagta gcatgatctc ggctcaccac agcctctgac tccctggttc aagtgattct    25260
cctgcctcag cctcctgagt agctgggatt acaggcacac accaccacac ccaactaatt    25320
tttgtatttt tggtagagac ggggtttcac catgttggcc aggatagtct caatctcctg    25380
acctcatgat cctccgacct tgcctgggag gccaaagtgc tgggattaca ggcgtgagcc    25440
accatgccca gcctagaagc atttcttaat gtctggtgtt ctctggctgt tgtatcttaa    25500
aaaaaaaagg gggggaaaac tgaggctcga ggtgaccttg tgagctggag cagagccggg    25560
atgggatgag gaggcaggag cgtgtgcaga agagaggag ccccctgag ctcgcaccct    25620 gcttcccgtg gctgggaggg gaggccgaga tgcttgggga gaaatggagg ctccaagcca    25680
gaggggctgt ttccagcacg ctcttactga gcgctgctgt agtccagctt ggtgtggcgg    25740
ctgtgggcag ggagggggaga gaggtctgag ctggctggcg gcccactggg cccctcccct    25800
gagcctccac cggccctctc ccagtgcgct gggctgggca agcctctgat gtgccagcca    25860
gatggagggt gaagtcctga tgcctgcccc taccctggga attgtgatgc tgcagttact    25920
gcccctgata acccctgact gggcatagga ccagctggct gagccagctc ctggggctga    25980
ggaggaagcc atgaacttga cctggcactt tccttgtctc caagcatcag tcaaccaagg    26040
atatggaggg ggtgtgtgca tgtgtgcaca catacacaca cacacacaca cacacttcaa    26100
cctgtttatc ccccttgaga tttgctgact tgtgcattgg gggtagaagg tgctggaaaa    26160
attccggtcc tggttctcag tttccccatc tgtccagtgg gagcagctgg actgagagac    26220
gcccatgtct cctgctgtgg tcctgcaagg aggctggcgc tcctgagtct gctccatcct    26280
ggcctgtcag gcctgcctgg atcctgcccc gggttggtcc accactcact gttttgtttc    26340
caggaggaga gggatcgccc tcccagctaa cacagcagag gggctgctga acgtcattgg    26400
catggacaag ccgctcaccc ttccagactt cctggccaag tttgactact acatgcctgc    26460
tatcgcgtga gttgccccca acccacaggt cctagggcag cattgatccc tatgactagg    26520
accaggcctg tccctcagcc tgtggggggcc agagaagttg ctctgaaacc acagctgtct    26580
ttctcaccat tgtgtacact tagtgagtct ctccagtgcc tttaggcctc agttttccct    26640
tctgagatgt gggtgtgatg gactgaaatt gcttcaagtt ctacagagaa atggcagaat    26700
atgggagcta agaacacagg gtcagaggca gtgcagggct tgaacccggg ccatctatct    26760
cctagttcag ggcttcgtgt tgtgagggga ggagaggcct gaatataggg tggggcggg    26820 gagatgtggg gaagattctc caaaaggctt tttctttttc ttgtcttgag tcgccaggga    26880
acagcactag gtaccgaaaa ggccagaagg ggtatgggcg agtactagag agaaatttcc    26940
atgactgctt tatttattta tttatttatt tatttattta tttattgaga cagagtctca    27000
ctctgttgcc caggctgaag tgcagtggtg cgatctcagc tcactgcaac ctccacctcc    27060
```

```
cagtttaagg gattctcctg ctttagcctc ccaagtagct gggatcacag gcacccacca    27120
tcacacccaa ctaatggttt tgtattttta gtagagatgg ggtttttacta tgtttgccag    27180 gctggtctcg aattcctgac ctcaggtgat ctgcccgcct cggcctccca aaatgctggg    27240
attacaggcg tgagccactg cgcctggcct ccatcctcat cctgaagatg caagaacttc    27300
tggtgacccc ttctcctgag agtggcctga tctcccctgg gcagggcact ttcttcccac    27360
gctgggctct cccacgactt gtgtgccttc cctcacacat tctagtaacc acttcatttt    27420
cactcttcat ggtgggaact tccagctaag cacagtccac cgttacgtga tcaacacagt    27480
ggccctggca ggccaatttg tgccttgctt ctggaacaaa catgcagtaa taacaacgaa    27540
aatgttttga gcatttgtcc gctctgctcc aagcactgac ccgggtgggg tttatgaagt    27600
ttgactcatt tgtccccgca ataactcctt gacctaggtg tcagagggtg actaaccagg    27660
ggtcacacag cagataagtg tgggcacaag gatccaagtc catgactgta tcccacgtgt    27720
ctcccacatc caggcatccc tctggacttg tccagctgtg tccttttctc tcatttctct    27780
tccctgccag ccttaactcc atcaccaaca aatattgggc tactctgtcc taggcatggt    27840
cctcagctga gaggtcgcag ccatcccaag acagaggggt ccttgccaca tggagactgc    27900
attctagtag ggaatacagc aaactggctg ataagccata tgacacacaa tgttgagtag    27960
tgataaggac ctgggagaaa aagaaagccc aggagaatgg tggaggggcc gttttaagat    28020
aaggcggtct gggccaggta cagtggctca cgcctgtatc cccagcactt tgggaggctg    28080
aggtgggcgg atcatgaggt caggagatcg agaccatcct ggctaacaca gcgaaacgct    28140
gtctctacta aaaatacaaa aaattagccg ggcgtggtgg catgcgcctg taatcccagc    28200
tacttgggag gctgaggcag acgaatcact tgaacccagg aggcagaggc tgcagtgagc    28260
tgagatggcg ccactgcact ccagcctggg cgacagagca agattctgtc tcaaaaaaaa    28320 aaaaaaaga taaggtggtc agggaaggcc tctctgagga ggtgaagctt cagctggctc    28380
taaaccaggg gagcgggaga gacgcagtgt aggacagtat cggggaagag caggcctgtg    28440
tcttctccgg tggcctcagg gaatgaggga gaaggaaggt gctggggagg ctggcaaggc    28500
tggaggatgc aggcttgtgg gcaggacctg ggagttgcga tgtcactctc cgtggcagga    28560
agctactggg gcttcgaggg gagaagtgat atgctttgat ttaccttctt aaaagattgc    28620
cccaactgct gggtggagaa caggatgaca ggggcaagca tggagacagg gaggccagtt    28680
agagatggcg tgattcaggc caggatgagg ggtgagaact ggtatgcagt tccaaagtag    28740
agctgatagg acttgcccag tgtctggatc ttatccagtg gatgcccaga gcttgggtct    28800
ggggatgaag tgggttttaat ctgccaaggg ttggggatgt catttgctcc tggagctccc    28860
aagggacttg gggaaggttg ttcccaaccc ctttcttccc ttcccagggg ctgccgggag    28920
gctatcaaaa ggatcgccta tgagtttgta gagatgaagc ccaaagaggg cgtggtgtat    28980
gtggaggtgc ggtacagtcc gcacctgctg gccaactcca agtggagcc aatcccctgg    29040 aaccaggctg agtgagtgat gggcctggaa ggggccatgc tgagggtgtg gctgggaggc    29100
tcagctctga gactggaagg gcgaactgct gggaatccct gacccaagca agaccttgtt    29160
cttgccccca gtctggtcca tggcctcaga aagatgggtt taactctgtc acaagagacg    29220
tggttcccat cctccctttg ccgttatgtt cttaccttgg gcacaagtgt ttggctgtgt    29280
cttgctctgg ccacaggcct gctgtccagg aatgttaacc tgcttagcca cccaggattt    29340
ctgaggggtc tcccttgtca ctgatgctga tcagatctct aaaggcccta aggtcctgc     29400
```

```
tctaacttca taactgaagt gagtctggcc catttctagc cccctgcctg ggcccccatg    29460
gatctctaag tggtatcaca aaaccaccct gccccatttt ctgagccatg attctgatac    29520
atatagaatg tgaacatcat ggcaggccca agcttagcaa tgctgtccat ctggggggtgg    29580 ggagggccat gttgacaccc cacacctccc actaagatct aggagcaccc agctgcttta    29640
agagctagag gacatgcta gggcctgggg gcatctctgc cagtctttcc tctgaggcag    29700
tgggtcagtg ggggaggagg gtcctcccca aagcctcctc ttcctcctct gtcccagtcc    29760
cagagctgcc ctttaggcct tccttttgcc tcaggcccat ccctactcct ctcctcacac    29820 agagggacc tcaccccaga cgaggtggtg gccctagtgg gccagggcct gcaggagggg    29880
gagcgagact tcgggtcaa ggcccggtcc atcctgtgct gcatgcgcca ccagcccagt    29940
gagtaggatc accgccctgc ccagggccgc ccgtctcacc ctggccctga cctcctggcc    30000
tagcagtggg gctgtacctg atctcccctg tgccccacag ccccatggtg tcccctttgag    30060 cccactggca tgaacttggg gcttcatgaa caactggag acctcctagg caggctcaga    30120
acttctggag atgttctccc cagggacacc atgcctttat agccaccctg caggaagctc    30180
aacaccaaat aggaacgtaa ctattgaaaa aaaaatctag gctagattct gatcagccca    30240
tagtcctccc tcgagaccca gtggaccagg ccccatcctg tctgggcctg aataggtctg    30300
atttccaaga tttctgaggg gtctcccttg tcactgacgc agatcagatc tctagagttt    30360
gtgcctcatg gtgcacagcc tcactgtgtg atattgggca ggtcacactg ctgctctggt    30420
tatgcaccaa gacacctcag ttgtgcactg tcacaaggag atgatcacac ttacttcatt    30480
cctctaccct caggattagt aagaaccaaa gagctacctg cacgcatttc ctctaatcct    30540
cgcagcagcc tgcaaagcag aactaccatt gcttagtccc atttgacaga tgaggaaact    30600
gaggtggagt gaggtgcagc ctcttgcaag gcacaaaccc tggatttgta tccggggaca    30660
tctagttcca aagcctgtgt tcattcattc tttcttaaac acttcagaat aactttattg    30720
gttaagagta cctaatacat tagcgagata cttcccaata ctagtgtgag ttctattttta    30780 gatgacgtgt taaacggtcc tccgtttcct catctgcgca tgggaataag cctaccatga    30840
gtgttgttgg aaacaccagg tgagagaagg gtccgtgtca tttactgagc tcaggccccg    30900
tccttggtgc tttacacaca tggcctcggc aaagcctggc cgtgaccctg tgcaatagct    30960
ggcagggttc tttctgaaaa gggcggaaac tgaggccata agcagagcag ttttccgcag    31020
ccatgtggtt aggacatagc agttaggatt tgaagacact gagccctgtt ttgtgctggc    31080
ctcccatggg gggtttgggt gggacagcag gcaggtaggc tgggaggtct ctccatggtg    31140
ctggtgacag agcctgggtg ggcatctgcc cacagactgg tcccccaagg tggtggagct    31200
gtgtaagaag taccagcagc agaccgtggt agccattgac ctggctggag atgagaccat    31260
cccaggaagc agcctcttgc ctggacatgt ccaggcctac caggtgggtc ctgtgagaag    31320
gaatggagag gctggccctg ggtgagcttg tctcccaccc atagttggga gaaatcacaa    31380
gaaccaggga ccatggtgtc tcctgagttc tgaagtgtgt cttttgttggg tcttaaggct    31440 tggaactgga atccccctgg gccaggcgtg gtggttcatg cctgtgatcc cagcactttg    31500
ggaggcgagg caggaggatt gcttgagcct aggagtttga gaccagccag gcaacatag    31560 tgagatccat ctctgcaaat acaaaaaaaaa gtagtcaggc atggtggtgc atgcctgtag    31620
tcccagctac ttgggaggct gaggtgggag aattgcttga gtccaggaag tcaaagctgc    31680
agtgagctgt gataatgcga ctgcactcca gcctgggtga cagagggaga ccctgtctca    31740
aaaaaaaaaa aaaggaagaa agaagaaaga gaaaagaaag agaaagaaag agaggaagga    31800
```

```
aggaaaaaga ggaagggagg gagggaggaa ggaaggaaag aaggaaggaa gggagagaga    31860
aagaaaagcc tccacttggt gttgggagtc ctgtgctgag cctgcttctg gctgtgattt    31920
gctgtgtgaa cctgggcaac actgtgtctt ctctgggcct ctgtttcttc tattgggatg    31980
actgagttgg agccgacatc tcaaaagtcg cttccagcgt gatgatgaat gggcctcctg    32040
tggagggtgc agcatggtgg agaagtcagg gctctggagt cccactgccc gggctcagag    32100
cttggttcca cacttcctgt ctgaccttgg tcacattact tgaatctcct gagcttcagt    32160
ccttcatcat aaaatgggtg ggataatagt tgtgaatatt agataatgta tacaagtcac    32220
ttcatatact acctgacaca tggtaactgg ctaatgagtg acagctacca cttagataag    32280
gacttggagg gtaaaagacc aggtttcccc atgctgttga agcaggcagc atgactagga    32340
tggttcaatc tccacagcat ggtcaaggca ggctgccggg gccctcccgc tagggcaccc    32400
atgacctggc tctcccccttt ccaggaggct gtgaagagcg gcattcaccg tactgtccac    32460 gccgggagg tgggctcggc cgaagtagta aaagaggtga gggcctgggc tggccatggg    32520
gtccctcctc actgcctcct cccatacttg gctctattct gcttctctac aggctgtgga    32580
catactcaag acagagcggc tgggacacgg ctaccacacc ctggaagacc aggcccttta    32640
taacaggctg cggcaggaaa acatgcactt cgaggtaagc gggccaggga gtggggagga    32700
accatccccg gctgtcccaa cttcctgtat agagaggcag aaagcagggc gggtcccagg    32760
aactcgaggg gtgcccccag gcccagacat ggggggagga atcagcatgg cctgggggcca    32820 tccctgccag ccacacacct gctcttccag atctgcccct ggtccagcta cctcactggt    32880
gcctggaagc cggacacgga gcatgcagtc attcggtgag ctctgttccc ctgggcctgt    32940
tcaattttgt tccaggaagg ccaaagaggg aagaaacttt agggattggg catcagccca    33000
tgccgcgtct tttagatatg aaatctcttc gacaccctgg gaagcaggca ttgccgtcct    33060
catcttacaa atgaggaatc cgaggcccag atgtgctgtg gcttgactgg gattacccag    33120
ctgctaacca gcagagctgg ggccctacag ctcatcagct ggagcagaac gctcccattac   33180 tctgagggaa gcttccacac ttccaattct cccaactctg cccccctggg catcgcatagg  33240 aagcaggagt ccctctggcc agcatgttct ctcttcctga cacctggccc ttgggacccc   33300
tgggcattcc cctgagcgcc atcttgaagc tttccaccgg aggtctgttc caccctgcct   33360
ggctcccatc ctggagtcta accagggtca aggccctcct tccgtcctgt cgccaagcca   33420
caggagcagt atcaggcctt aggaaaaagc cgccttcccc aagacaagga cagcaagaac   33480
tcagggtgac catggtcagg ccagcactta tccatctgcc aggcatatga aaggggagg    33540 ggcttcggct ctgatgttct gatgacaagg gggtcttggg gcttgcttag ggacacgtgg   33600
cacctgtgga ggttcttgga ggcatgtggg tataccatgg gctggaaaaa gatccaggag   33660
tcatctgcac agatatggtg gctgaaggag aagcagtggc cccaggaggt ggtggagcaa   33720
gaagggccta ggatagaacc cagaaggaca atggtattta agggaccagc aaaagagaca   33780
agtaggagga aagtcaaaag tgtggtgtca cagaaatcca gggaaaaggt ttcaagaaac   33840
agtcaacagt gtgaaattct gctatgcaag tcgattatgg tcagagctag gaaagatcca   33900
ttagatacaa caagatggtg gtcagggatc gtgccaagaa cagcttccat ggtatgttgg   33960
agtagccagc tcccagtggg actgaggaac aagcagggta gggtgcagag gggaaggctg   34020
gagagggtgg cagccggagg gggatgttgc tttcttggct cccaccccca cgccccacc    34080 ggctgccatt ctgcctggtt cccatgtctg gcccctctgc tgcctttgcc cagctctggt   34140
```

```
cttcaggatg ggctggattc tggactttct ggttacatag acttgaacaa gtcacctaag   34200
ttctgaattt atttccccct ctgcacaagg atcagatctt tcagatctgt ttgaggctgc   34260
tgtgaggatc aaaggcgggt gaacgtcaat gtgttctgac tatttatgta agagtaaaag   34320
gaggctgatt ctctcctcct ccctcttctg caggctcaaa aatgaccagg ctaactactc   34380
gctcaacaca gatgacccgc tcatcttcaa gtccaccctg acactgatt accagatgac    34440 caaacgggac atgggcttta ctgaagagga gtttaaaagg ctggtgagtg ggtgtgagcc   34500
atactggcct tgactcgggt ttgggagtat ggtatctaca ggtccagtcc ggggcctgga   34560
atctttggag agagggagtg agtctgcctc aacagtccaa gacaagccca acctagacac   34620
tttccacaga gaagacatct ttgtgttgac gtcctgacct aggaccaggt ttttgatcct   34680
ttgcttgggt tgagtgcctt taaagaatcc agtgaaagct gtcaaccctc tccccagaaa   34740
ggtgtgtgca gcagctatga agtcttgcac actctcttca ggttgttctt aaatcccagg   34800
ctgaataagt ccattcctgc acgtgtctgc gaggtgtctc tggcccccta catgccaccc   34860
tgtctctcaa aggtttctcc aacttccttc tcacagccct ttttcatgta atgacaaatt   34920
aagaacacga cctcatggtc tctactctgg cacttgctgc cgtgtgacag tggacaaatc   34980 cttcccccctc taagcgtatc tgcccatgtt gagtgaagag gatggactat cactacattg   35040
ctaagagctg ccttctttgt tctctggttc catgttgtct gccattctgg cctttccaga   35100
acatcaatgc ggccaaatct agtttcctcc cagaagatga aaagagggag cttctcgacc   35160
tgctctataa agcctatggg atgccacctt cagcctctgc aggtaggttc ctgtctgggc   35220
ttctgggcag ttgcctgtcc tggccccagt gtggctttct gtgggacttc tagcaagatg   35280
cccttccatt cttgggcagc gcatgaatgt gtgatgactc cctggtttct gggccctggc   35340
tgggagcagc gtctcattag atcggtttgt tttctataaa agttcttgag aggctgttct   35400 aagggggagac tttctgaagc ccagtcccaa aggtctgggc agttggggac acctccatgg   35460
ctgcccaaag ccaagggcag ggagaggggc ccaggctgtt ctgctccttt cttcctatgt   35520
ggtcttggca aggcatcttc ttgccatcat aggaaggagt tcctttctgg ttctggtgtt   35580
ctatgatttt tacaacatcc tgggtactac aagttgcctg atcttttgc ttctctgaac    35640 caacgagcag ggcagaacct tgaagacgc cactcctcca agccttcacc ctgtggagtc    35700
accccaactc tgtggggctg agcaacattt ttacatttat tccttccaag aagaccatga   35760
tctcaatagt cagttactga tgctcctgaa ccctatgtgt ccatttctgc acacacgtat   35820
acctcggcat ggccgcgtca cttctctgat tatgtgccct ggccagggac cagcgccctt   35880
gcacatgggc atggttgaat ctgaaaccct ccttctgtgg caacttgtac tgaaaatctg   35940
gtgctcaata aagaagccca tggctggtgg catgcagcag gtggcatgta atttggtggt   36000
cttgggcggg ccgatgtggg caggatgagc atggagggag ctgggtcagc ctgctcagca   36060
gcagggcctg agcctaaggg tggctgtgaa tgccaggcca gagatcccaa tgctgtgggc   36120
caagaggggg ccagaggctg tcctccttcc agaagaaata aggcttctct ggttgttgct   36180
caaacattcc ctgaactctc agcccctcct aactctaggt tttaaggagt aaagcttcct   36240
tttgggttcc tgaagctggc agttggggtg agagcagatg agatggaaga gggctcatca   36300
gacactggcc ttgagggtg ctggcctctg cagaacgcca gcatcttctc agaatcgtat    36360
gttctagaag cctgggcgaa gtccggctaa ttgtggactt ggggaaaata aggcccaacc   36420
cctgtttttg caaggttaag gagaaataat cttaaaccag tcacacaaat catcggcatt   36480
tatttcctgg gtcctaggtg tcacttatcc tggtggacag ggcagaggtg gtcagatcgt   36540
```

```
tttgagccaa aatcccttcc ctaaaaatgg atctgtggag ctccatgagg gaacctcaga   36600
gatgcacaat gacagtttag ctaaaatggc ttaaaaaatg tgaattgatt gtcagctctc   36660
tccatatctg ctgaaaaaag gtttaaaatt tttaaaaagt ttaaaagtgt tttctaaaaa   36720
agggacaagc aggtctggac c                                            36741
```

<210> SEQ ID NO 4
<211> LENGTH: 363
<212> TYPE: PRT
<213> ORGANISM: Homo sapiens

<400> SEQUENCE: 4

```
Met Ala Gln Thr Pro Ala Phe Asp Lys Pro Lys Val Glu Leu His Val
  1               5                  10                  15

His Leu Asp Gly Ser Ile Lys Pro Glu Thr Ile Leu Tyr Tyr Gly Arg
                 20                  25                  30

Arg Arg Gly Ile Ala Leu Pro Ala Asn Thr Ala Glu Gly Leu Leu Asn
             35                  40                  45

Val Ile Gly Met Asp Lys Pro Leu Thr Leu Pro Asp Phe Leu Ala Lys
 50                  55                  60

Phe Asp Tyr Tyr Met Pro Ala Ile Ala Gly Cys Arg Glu Ala Ile Lys
 65                  70                  75                  80

Arg Ile Ala Tyr Glu Phe Val Glu Met Lys Ala Lys Glu Gly Val Val
                 85                  90                  95

Tyr Val Glu Val Arg Tyr Ser Pro His Leu Leu Ala Asn Ser Lys Val
            100                 105                 110

Glu Pro Ile Pro Trp Asn Gln Ala Glu Gly Asp Leu Thr Pro Asp Glu
        115                 120                 125

Val Val Ala Leu Val Gly Gln Gly Leu Gln Glu Gly Glu Arg Asp Phe
130                 135                 140

Gly Val Lys Ala Arg Ser Ile Leu Cys Cys Met Arg His Gln Pro Asn
145                 150                 155                 160

Trp Ser Pro Lys Val Val Glu Leu Cys Lys Lys Tyr Gln Gln Gln Thr
                165                 170                 175

Val Val Ala Ile Asp Leu Ala Gly Asp Glu Thr Ile Pro Gly Ser Ser
            180                 185                 190

Leu Leu Pro Gly His Val Gln Ala Tyr Gln Glu Ala Val Lys Ser Gly
        195                 200                 205

Ile His Arg Thr Val His Ala Gly Glu Val Gly Ser Ala Glu Val Val
    210                 215                 220

Lys Glu Ala Val Asp Ile Leu Lys Thr Glu Arg Leu Gly His Gly Tyr
225                 230                 235                 240

His Thr Leu Glu Asp Gln Ala Leu Tyr Asn Arg Leu Arg Gln Glu Asn
                245                 250                 255

Met His Phe Glu Ile Cys Pro Trp Ser Ser Tyr Leu Thr Gly Ala Trp
            260                 265                 270

Lys Pro Asp Thr Glu His Ala Val Ile Arg Leu Lys Asn Asp Gln Ala
        275                 280                 285

Asn Tyr Ser Leu Asn Thr Asp Asp Pro Leu Ile Phe Lys Ser Thr Leu
    290                 295                 300

Asp Thr Asp Tyr Gln Met Thr Lys Arg Asp Met Gly Phe Thr Glu Glu
305                 310                 315                 320

Glu Phe Lys Arg Leu Asn Ile Asn Ala Ala Lys Ser Ser Phe Leu Pro
                325                 330                 335
```

```
Glu Asp Glu Lys Arg Glu Leu Leu Asp Leu Leu Tyr Lys Ala Tyr Gly
            340                 345                 350

Met Pro Pro Ser Ala Ser Ala Gly Gln Asn Leu
            355                 360
```

ADENOSINE DEAMINASE DEFICIENT TRANSGENIC MICE AND METHODS FOR THE USE THEREOF

The present application claims the benefit of provisional applications, Ser. No. 60/083,408, filed on Apr. 29, 1998, and provisional application, Ser. No. 60/083,370, filed Apr. 28, 1998.

The government owns rights in the present invention pursuant to grant number AI43572, DK46207, HD34130, HD07843 and HL61888 from the National Institutes of Health as well as grant number 011618-060 from the Texas Higher Education Coordinating Board Applied Technology Grant.

1.0 BACKGROUND OF THE INVENTION

1.1 Field of the Invention

The present invention provides adenosine deaminase (ADA) deficient mice. Also provided are methods of using the mice as an animal models for the analysis of physiological states that are sensative to disturbances in adenine nucleoside metabolism.

1.2 Description of Related Art

1.2.1 Adenosine Deaminase Deficiency

Genetic defects in purine metabolism in humans result in serious metabolic disorders, often with pronounced tissue-specific phenotypes (Blaese, 1995a). A striking example of this is adenosine deaminase (ADA) deficiency, which results in impaired lymphoid development and a severe combined immunodeficiency disease (SCID) (Hershfield and Mitchell, 1995).

ADA deficient SCID was the first of the inherited immunodeficiencies for which the underlying molecular defect was identified (Giblett et al., 1972); however, despite over 20 years of subsequent research, a satisfactory explanation for the lymphoid specificity of this metabolic disease has not emerged. This is largely due to the inaccessibility of human tissue for detailed phenotypic and metabolic analysis and the absence of an animal model which retains features of ADA deficiency in humans.

Additional interest in ADA deficiency stems from recent attempts to use novel therapeutic strategies, including enzyme therapy (Hershfield et al., 1993) and gene therapy (Bordingon et al., 1995; Blaese et al., 1995), to treat the condition in humans. Although the results of these therapeutic approaches are encouraging, unexpected outcomes have raised numerous important questions regarding the efficacy of specific treatment protocols (Hershfield et al., 1993; Blaese, 1995b). The pace with which new enzyme and gene therapy protocols can be tested would be greatly increased by the availability of an animal model for ADA deficiency.

The availability of a genetic animal model for ADA deficiency would make possible a wide range of biochemical and immunological experiments that are not permissible with humans.

Attempts to generate ADA deficient mice were initially reported by two groups (Wakamiya et al., 1995; Migchielsen et al., 1995), resulting in animals with independent sites of Ada gene disruption. However, these attempts did not lead to the production of viable ADA deficient mice. In each case a similar phenotype was observed. ADA deficient fetuses died perinatally due to severe liver damage (Wakamiya et al., 1995; Migchielsen et al., 1995). This phenotype was accompanied by profound disturbances in purine metabolism, including marked increases in the ADA substrates adenosine and 2'-deoxyadenosine.

2'-Deoxyadenosine is a cytotoxic metabolite that can kill cells through mechanisms that include disturbances in deoxynucleotide metabolism (Ullmann et al., 1978; Cohen et al., 1978) and the inhibition of cellular transmethylation reactions (Hershfield, 1979; Hershfield et al., 1979). ADA deficient fetuses exhibited evidence for both of these mechanisms of 2'-deoxyadenosine cytotoxicity, in that levels of the 2'-deoxyadenosine metabolite, dATP, were markedly elevated, and the enzyme S-adenosylhomocysteine (AdoHcy) hydrolase was inhibited (Wakamiya et al., 1995; Migchielsen et al., 1995). These metabolic disturbances are thought to contribute to the liver damage and subsequent death of ADA deficient fetuses.

Previous attempts by the inventors to produce mice that expressed ADA in the fetus but not in the neonatal mouse had failed (Blackburn et al., 1995). The strategy was to introduce an ADA transgene that would only be expressed in the placenta into heterozygous ADA knockout mice. The heterozygous transgenic mice could then be mated to yield homozygous ADA knockout mice that were able to develop because of the transgene provided ADA expression in the placenta. Viable mice were obtained by this strategy; however, the promoter used to express the transgene was not specific to the placenta and ADA expression was detected in the gastrointestinal tract of these animals, predominantly in the forestomach. Therefore, although ADA was not expressed in the lungs of these animals, ADA expression was present in the gut.

Disclosed herein is description of a mouse lacking postpartum ADA expression. This was acheived by creating a placenta specific promoter (Shi et al., 1997) and using this promoter in a transgene construct to express ADA. Indeed, the ADA deficient mice have immunodeficiencies similar to that of humans with ADA deficiency (Blackburn, 1998). Surprisingly and unexpectedly, the ADA deficient mice showed lung abnormalities. Upon extensive examination, the inventors were able to determine that the lung abnormalities in ADA deficient mice were reminiscent of those seen in asthma.

1.2.2 Asthma

Asthma is an inflammatory disease of the airways. In the U.S., 13% of children and 6% of adults suffer from asthma and 1% of health care cost are devoted to asthma treatment (Vogel 1997, Cochrane et al., 1996; Weiss et al., 1992). The disease is typified by the infiltration and activation of immune cells in the lung, followed by airway inflammation and obstruction (Vogel 1997). Many factors can trigger asthma, however, the mechanisms by which these triggers lead to airway inflammation and damage are not well understood. There is increasing evidence that asthma has its roots in early life (Barker 1992; Busse et al., 1995), but the mechanisms involved are not understood. Nor is it known how genetic and environmental influences interact to manifest asthma. Therefore, there is a need in the art for a model system with a predetermined genetic background that would allow testing of the influence of environmental factor on asthma development.

1.2.3 Animal Models and Asthma

Because of the limitations on the availability of human tissues, a number of animal models have been developed to better define the structural and functional consequences produced by environmental agents within the respiratory tract (Larsen and Colasurdo, 1997; Abraham and Baugh, 1995). While an ideal animal model should exhibit all the features of human asthma, there is general agreement that a single animal model does not exhibit all the functional and biological changes that would mimic the disease process seen in humans (Larsen and Colasurdo, 1997).

1.2.4 Adenosine Signaling in Asthma

Adenosine is a regulatory nucleoside that has the potential to be produced from all cells as a product of ATP catabolism (Arch and Newsholme, 1978). In mammalian tissues there exist two metabolic pathways through which adenosine can be generated: One is through the enzyme 5'-nucleotidase, which generates adenosine by enzymatic dephosphorylation of 5'-AMP (Zimmerman 1992). The other involves the hydrolysis of S-adenosylhomocysteine to adenosine and homocysteine (Schutz et al., 1981). Once generated, adenosine is freely transported in and out of cells through an ubiquitous nucleoside transporter (Arch and Newsholme, 1978) and serves as an extracellular signal. Inside the cell it is either deaminated to inosine by ADA (Blackburn and Kellems 1996) or is phosphorylated to AMP by adenosine kinase (Arch and Newsholme, 1978). Extracellular adenosine can bind to cell surface receptors to elicit a wide variety of cellular responses (Stiles 1992).

The regulatory actions of adenosine are mediated by several distinct membrane receptors that are classified as P1 purinergic receptors (Olah and Stiles 1995). Distinct subtypes of adenosine receptors have been identified on the basis of cDNA sequence and pharmacological profiles and are termed A1, A2a, A2b, and A3 adenosine receptors (Libert et al., 1989; Stehle et al., 1992; Pierce et al., 1992; Rivkees and Reppert, 1992; Fink et al., 1992; Zhou et a., 1992; Salvatore et al., 1993). Adenosine receptors are tightly coupled to effector enzymes by guanine nucleotide (G-protein) regulatory proteins (Stiles 1992; Olah and Stiles 1995), and each receptor subtype has a distinct affinity for adenosine and its structural congeners. Both A2 receptor subtypes couple to adenylate cyclase by stimulatory Gs-proteins and subsequently raise intracellular cAMP levels; in contrast, A1 and A3 receptors couple to inhibitory Gi-proteins and have the opposite effect (Olah and Stiles 1995). A1 and A3 receptors have also been shown to mediate the activation of potassium channels, inactivate calcium channels, stimulate or inhibit phosphatidylinositol turnover, inactivate phospholipase A2 or C, and inhibit chloride transport (Linden, 1991; Olah and Stiles 1995). Thus, adenosine signaling can have input into multiple intracellular signal transduction pathways. There is evidence that all four of these receptors are expressed in lung tissue and inflammatory cells and have all been implicated in participating in asthma (Dixon et al., 1996; Marquart 1997; Marquart et al., 1994).

Adenosine has been recognized as a potential signaling molecule in asthma (Holgate et al., 1992; Marquart 1997). Theophyline, an adenosine receptor antagonist, has been used in the treatment of asthma for decades (Barnes 1997). Adenosine is produced in response to tissue damage such as hypoxia (Arch and Newsholme, 1978) and has been shown to be released from hypoxic lung tissue (Mentzer et al., 1975), and to be elevated in bronchoalveolar lavage fluid (Driver et al., 1993) and blood (Mann et al., 1986) from asthma patients. Adenosine receptor expression increases in lung tissues from asthma patients (Richardson, 1997), and asthmatics are much more sensitive to exposure to adenosine than non-asthmatics (Cushley et al., 1983).

In vitro studies have shown that adenosine can enhance mediator release from human lung mast cells (Marquart et al., 1978), and adenosine itself can be released from stimulated mast cells (Marquart et al., 1984). Mast cell degranulation has been attributed to the A3 receptor (Reeves et al., 1997) and the A2b receptor has been implicated in IL-8 secretion from mast cells (Feoktistov and Biaggioni 1995). Adenosine also modulates pro-inflammatory events in eosinophils (Kohno et al., 1996; Walker 1996) and promotes macrophage differentiation (Najar et al. 1990). In addition, asthma induced in a rabbit model was prevented by preexposing the lungs to antisense oligonucleotides directed at blocking expression of the A1 receptor (Nyce and Metzer 1997).

Many of the known methods of treating asthma that are adenosine related focus on disrupting adenosine signalling through the receptors of the lung tissue. However, the present invention is the first to focus on lowering adenosine levels in an animal as a treatment for asthma. Surprisingly, the inventors were able to demonstrate that reduction of systemic adenosine levels alleviates asthma.

1.2.5 Adenosine and Deoxyadenosine Signaling in Severe Combined Immunodeficiency ADA deficiency in humans is most often associated with a severe combined immunodeficiency (SCID) that is thought to arise from perturbations in signaling processes that result from the accumulation of the ADA substrates adenosine and deoxyadenosine (Hershfield and Mitchell, 1995). The exact mechanism through which accumulations in adenosine and/or deoxyadenosine lead to SCID are not know. Since the thymus and spleen, major immune organs, exhibit expression of adenosine receptors (Dixon et al., 1996), it is likely that adenosine signaling may be involved. Deoxyadenosine does not bind extracellular receptors, but has potent cytotoxic effects that are mediated through various intracellular pathways (Hershfield and Mitchell, 1995). Both adenosine and deoxyadenosine levels are elevated in the immune organs of the ADA deficient mice that are the topic of this invention OBlackburn et al., 1998). In addition, these animals suffer from a combined immunodeficiency similar to that seen in ADA deficient humans. It is therefore likely that ADA deficient animals will serve as excellent models for determining how adenosine and deoxyadenosine signaling contribute to SCIDS, as well as serve as models for developing and testing therapies for the treatment of this disease, including enzyme therapy and gene therapy.

1.2.6 Adenosine Signaling in Other Physiological Systems

By generating animals that lack ADA, the enzyme responsible for controlling adenosine levels in tissues and cells, the inventors have created animals that exhibit systemic elevations in adenosine levels. It is therefore likely that these mice will prove useful in assessing the role of adenosine signaling in some if not all of these physiological systems. These systems include cardiovascular and vascular, neurologic, immunologic, renal, gastrointestinal, vascular, skeletal, and reproductive systems.

2.0 SUMMARY OF THE INVENTION

Homozygous Ada null mice fail to develop properly and die in utero (Wakamiya et al., 1995). Subsequently, the inventors attempted to rescue the Ada deficient fetuses by providing Ada encoded on a transgene that would only be expressed during development. The inventors were able to rescue the homozygous Ada null fetuses but the promoter was not specific to the placenta and ADA expression was detected in the intestinal tracts of the mice (Blackburn et al., 1995). The present invention provides homozygous Ada null mice that lack expression of ADA post-partum.

The inventors report here a mouse that is homozygous for a null Ada allele and comprises a tissue-specific ADA transgene. In preferred embodiments, the tissue-specific transgene is expressed at a specific developmental stage during the fetal development of the mouse, most preferably trophoblasts. An important aspect of the present invention is that the expression of the transgene after birth is at a level that leads to increased adenosine levels in the mouse. In preferred embodiments, there is no detectable ADA activity in the mouse after birth. The inventors have shown herein that such expression is provided by a transgene comprising an ADA gene and a trophoblast specific promoter.

Of course, the present invention is not limited to transgenes with trophoblast specific promoters. The inventors contemplate that essentially any promoter that is expressed in any or all tissues of the developing fetus may comprise the transgenes of the present invention. However, for some aspects of the invention, it is preferred that the promoters not be expressed postpartum. In some embodiments, very low levels are permissible but expression is at a level such that adenosine levels within the mice are increased as compared to mice expressing endogenous ADA, such as heterozygous Ada null mice. By "endogenous expression" it is meant expression from the natural Ada allele.

Also provided by the present invention are methods of producing a mouse that is homozygous for a null Ada allele. The methods comprise crossing a first mouse comprising a tissue-specific ADA transgene with a second mouse heterozygous for a null Ada allele, thus obtaining a third mouse comprising the transgene and the null Ada allele. This third mouse is then crossed with a fourth mouse that may be heterozygous or homozygous for a null Ada allele to produce a fifth mouse that comprises the tissue-specific ADA transgene and is homozygous for the null Ada allele. The inventors contemplate that the fourth mouse may comprise a tissue-specific ADA transgene.

In preferred embodiments, the tissue-specific transgene is expressed at a specific developmental stage during the development of the fifth mouse. Most preferred are methods comprising transgenes that are expressed in trophoblasts during the development of the fifth mouse.

Further provided by the present invention is a mouse comprising a tissue-specific ADA transgene which is homozygous for a null Ada allele preparable by crossing a first mouse comprising a tissue-specific ADA transgene with a second mouse heterozygous for a null Ada allele, thus obtaining a third mouse comprising the transgene and the null Ada allele. This third mouse is then crossed with a fourth mouse that may be heterozygous or homozygous for a null Ada allele to produce a fifth mouse that comprises the tissue-specific ADA transgene and is homozygous for the null Ada allele. The inventors contemplate that the fourth mouse may comprise a tissue-specific ADA transgene.

The present invention also provides methods of screening for compounds having pharmaceutical activity in the treatment of dysfunction indicated by an elevated level of adenosine. These methods comprise obtaining a viable mouse which has a reduced level of ADA activity and manifests a dysfunction indicated by an elevated level of adenosine, obtaining a candidate compound; administering the candidate compound to the mouse, and monitoring the mouse to determine whether the candidate compound manifests pharmaceutical activity. In preffered embodiments, the dysfunction is in the respiratory, nervous, cardiovascular, vascular, renal, skeletal, reproductive, or immune systems.

In preferred embodiments, the mouse has substantially no ADA activity after birth and is homozygous for a null Ada allele. However, in some embodiments, the mouse may exhibit some ADA activity after birth but the ADA activity is at a level that is reduced relative to a normal mouse. A normal mouse may be a mouse of the same strain as the mouse with reduced levels of ADA activity and, preferably, heterozygous for an Ada null allele. In some preferred embodiments, the ADA activity is the result of expression of an ADA transgene in the gastrointestinal tissue of the mouse after birth.

By "having pharmaceutical activity" it is meant that the compound is capable of reducing the disfunction associated with elevated levels of adenosine. In prefered embodiments, the dysfunction can be in the respiratory, nervous, cardiovascular, vascular, renal, skeletal, reproductive, or immune systems. In some preferred embodiments, respiratory disfunction may be measured by a number of ways including, but not limited to, measurement of respiratory resistance, determining the breathing rate of the animal, or quantifying the number of eosinophils in the lungs of the mouse. In preferred embodiments, determination is done by way of quantifying the number of eosinophils in the lungs. Eosinophils may be acquired from the lungs of animals by bronchoaveolar lavage.

The inventors contemplate that essentially any compound, including any drugs known to affect a pulmonary phenotype, may be screened for pharmaceutical activity using the methods of the present invention. In prefered embodiments, the compound may interact with adenosine receptors. Such compounds can be agonists or antagonists of the adenosine receptors. In preferred embodiments, the candidate compound is a polypeptide with an ADA polypeptide being most preferred. However, polypeptides capable of metabolizing adenosine or 2'-deoxyadenosine are contemplated as candidate compounds. Such compounds include nucleoside phosphorylases.

A further important embodiment of the present invention is a method of treating a mammal having a dysfunction, indicated by an elevated level of adenosine, comprising treating the mammal to reduce the level of adenosine relative to the elevated level of adenosine. The treatment can be for dysfunctions of the respiratory, nervous, cardiovascular, vascular, renal, skeletal, reproductive, or immune systems. In prefered embodiments, the dysfunction is in the respiratory system, such as asthma. In preferred embodiments the treatment comprises providing ADA to the mammal. This may be done by the injection of ADA into the mammal, preferably at a dosage of 3 to 300 Units per kilogram weight of the mammal. The introduction of ADA to an animal may be by a single introduction procedure (acute treatment) or by a series of introduction procedures (chronic treatment). The series of introduction procedures may comprise a series of injections. In preferred embodiments, the injections occur roughly once or twice weekly.

In another embodiment, the ADA is provided by introducing into the mammal a gene encoding ADA in a manner that leads to expression of ADA in the mammal. This may be done through the gene therapy methods. The inventors further contemplate that ADA activity may be provided to the mammal by introducing ADA-producing cells in the mammal.

Also provided by the present invention are methods of rescuing an ADA deficient fetus which comprise providing one or more tissues of the fetus with ADA. This providing may be by means of a transgene or by means of providing ADA polypeptides to the fetus. Of course other methods of rescuing a ADA deficient fetus are contemplate and include providing one or more tissues of the ADA deficient fetus with a compound selected from the group consisting of S-adenosylhomocysteine hydrolase, ribonucleotide reductase, caspases, DNA fragmentation factors, and adenosine receptors. These compounds are capable of reducing the effects of high adenosine levels in the developing fetus, thus allowing the complete development of the fetus. In preferred embodiments, these compounds are no longer provided to the mice post-partum.

The inventors contemplate that the unique features of the mice of the present invention provide excellent model systems for a number of disorders and are not limited to lung dysfunctional disorders. Such disorders include cardiac and cardiovascular regulation, neurological, immunologic, renal, gastrointestinal, vascular, skeletal and reproductive systems (Jacobson and Jarvis, 1997). The mice also are an excellent tool for the study of adenosine signaling in an animal.

Furthermore, the mice of the present invention may be used to determine the effect of environmental conditions or pathogens on asthma. This may be accomplished by comparing a mouse of the present invention that is subjected to the environmental condition to a mouse of the present invention not subjected to the environmental condition.

In preferred embodiments, the inventors use ADA compositions to reduce the level of adenosine in an animal. Of course, other compounds are contemplated to be useful in the compositions and methods of the present invention. Essentially any compound that metabolizes adenosine or is capable of reducing systemic adenosine concentrations is contemplated for use in the present invention. In addition to compounds that metabolize adenosine, compounds that influence the action of adenosine receptors is contemplated for use in the present invention. These include both specific and nonspecific agonists and antagonists of adenosine receptors. Throughout this application referral to ADA compositions and functional equivalents thereof is meant to include any compound that metabolizes adenosine or reduces systemic levels of adenosine in an animal.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. ADA deficient mice exhibit a severe lymphopenia and immunodeficiency. Lymphoid cell numbers from thymuses and spleens are given as mean cell numbers in millions±SEM, n=7 for control organs (open bars), n=6 for ADA deficient organs (solid bars). *** represents a significant difference from control values with $P>0.001$.

FIG. 1B. ADA deficient mice exhibit a severe lymphopenia and immunodeficiency. Peripheral lymphoid cell counts are given as cells/$\mu$l blood±SEM, n=29 for control values (open bar), n=16 for ADA deficient values. *** represents a significant difference from control values with $P>0.001$.

FIG. 1C. ADA deficient mice exhibit a severe lymphopenia and immunodeficiency. Total immunoglobulin levels were measured in the serum of control (open bars) and ADA deficient (solid bars) mice. Values are given as $\mu$g/ml±SEM, n=7 for control mice, n=6 for ADA deficient mice. *** represents a significant difference from control values with $P>0.001$.

FIG. 2A. Analysis of lymphoid cell distributions in ADA deficient mice. Flow cytometry was performed on thymus cell preparations from aged-matched control and ADA deficient mice. Values are given as mean percentages±SEM, n=7 for control organs (open bars), n=6 for ADA deficient organs (solid bars). * represents a significant difference from control with $P>0.05$, ** $P>0.01$.

Figure 2B:
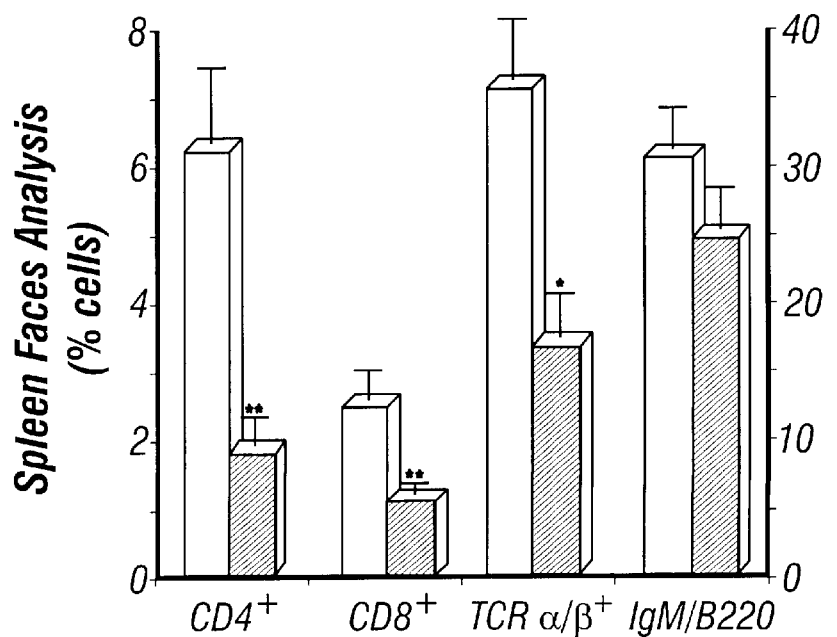

FIG. 2B. Analysis of lymphoid cell distributions in ADA deficient mice. Flow cytometry was performed on spleen cell preparations from aged-matched control and ADA deficient mice. Values are given as mean percentages±SEM, n=7 for control organs (open bars), n=6 for ADA deficient organs (solid bars). * represents a significant difference from control with $P>0.05$, ** $P>0.01$.

Figure 3A:
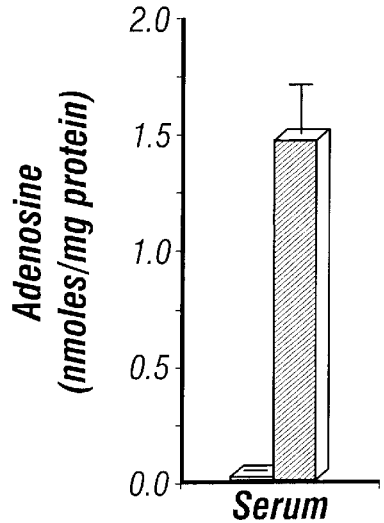

FIG. 3A. Disturbances in adenosine levels in tissues of ADA deficient mice. Adenosine levels were quantitated in serum. Mean values are given as nmoles adenosine per mg protein±SEM, n=8 for control mice (open bar), n=4 for ADA deficient mice (solid bar).

Figure 3B:
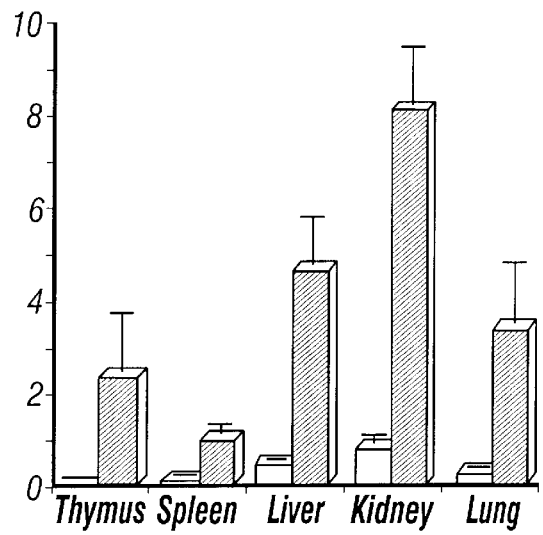

FIG. 3B. Disturbances in adenosine levels in tissues of ADA deficient mice. Adenosine levels were quantitated in the indicated tissues. Mean values are given as nmoles adenosine per mg protein±SEM, n=8 for control mice (open bars), n=4 for ADA deficient mice (solid bars).

Figure 3C:
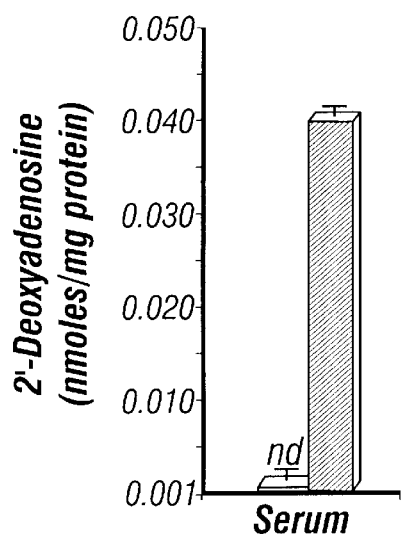

FIG. 3C. Disturbances in 2'-deoxyadenosine levels in tissues of ADA deficient mice. 2'-Deoxyadenosine levels were quantitated in serum. Mean values are given as nmoles 2'-deoxyadenosine per mg protein±SEM, n=8 for control mice (open bar), n=4 for ADA deficient mice (solid bar), nd, not detected at a lower limit of 0.001 nmole/mg protein.

Figure 3D:
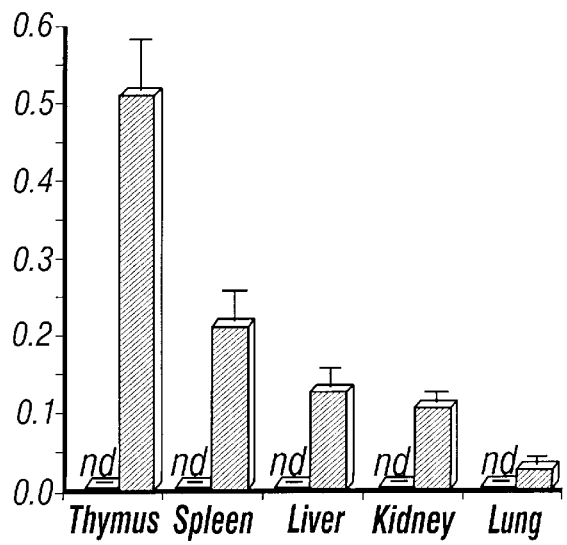

FIG. 3D. Disturbances in 2'-deoxyadenosine levels in tissues of ADA deficient mice. 2'-Deoxyadenosine levels were quantitated in the indicated tissues. Mean values are given as nmoles 2'-deoxyadenosine per mg protein±SEM, n=8 for control mice (open bars), n=4 for ADA deficient mice (solid bars), nd, not detected at a lower limit of 0.001 nmole/mg protein.

Figure 4A:
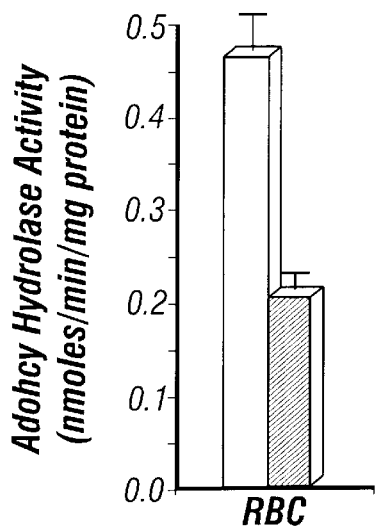

FIG. 4A. Disturbances in AdoHcy hydrolase enzymatic activity in tissues of ADA deficient mice. AdoHcy hydrolase enzymatic activity was measured in red blood cells (RBC) of control (open bar) and ADA deficient (solid bar) mice. Mean values are given as nmoles AdoHcy formed per min per mg protein±SEM, n=10 for control RBC, n=7 for ADA deficient RBC.

Figure 4B:
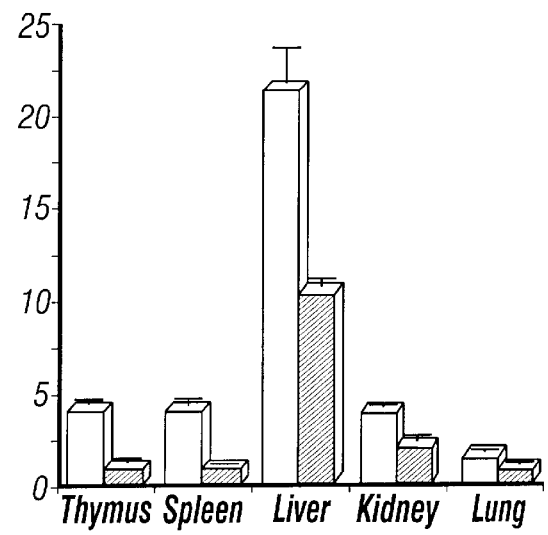

FIG. 4B. Disturbances in AdoHcy hydrolase enzymatic activity in tissues of ADA deficient mice. AdoHcy hydrolase enzymatic activity was measured in the indicated tissues of control (open bars) and ADA deficient (solid bars) mice. Mean values are given as nmoles AdoHcy formed per min per mg protein±SEM, n=4 for other control tissues, n=3 for other ADA deficient tissues.

Figure 4C:
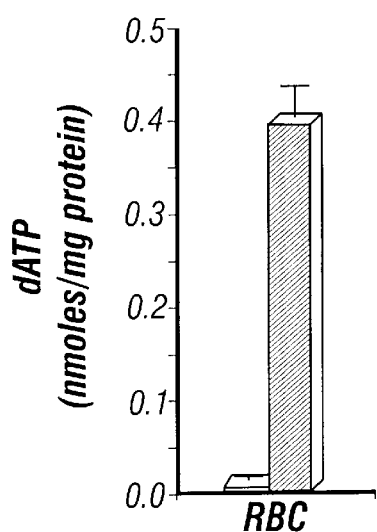

FIG. 4C. Disturbances in dATP levels in tissues of ADA deficient mice. dATP levels were quantitated in RBC of control (open bar) and ADA deficient (solid bar) mice. Mean values are presented as nmoles dATP per mg protein±SEM, n=7 for control RBC, n=6 for ADA deficient RBC.

Figure 4D:
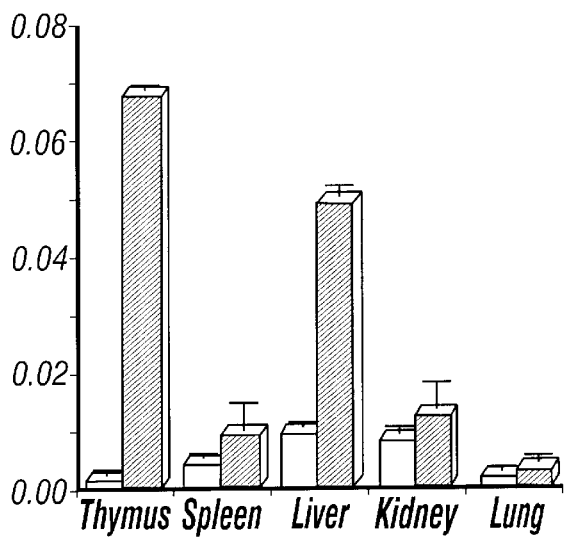

FIG. 4D. Disturbances in dATP levels in tissues of ADA deficient mice. dATP levels were quantitated in the indicated tissues of control (open bars) and ADA deficient (solid bars) mice. Mean values are presented as nmoles dATP per mg protein±SEM, n=3 for other control and ADA deficient tissues.

Figure 5A:
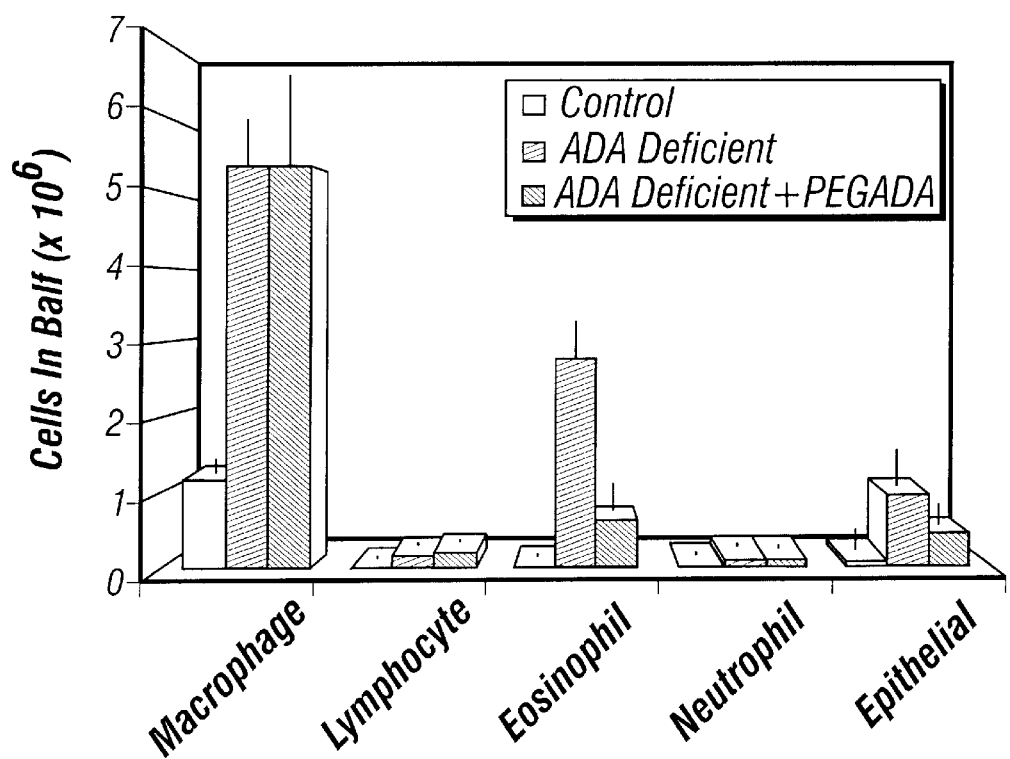
Figure 5B:
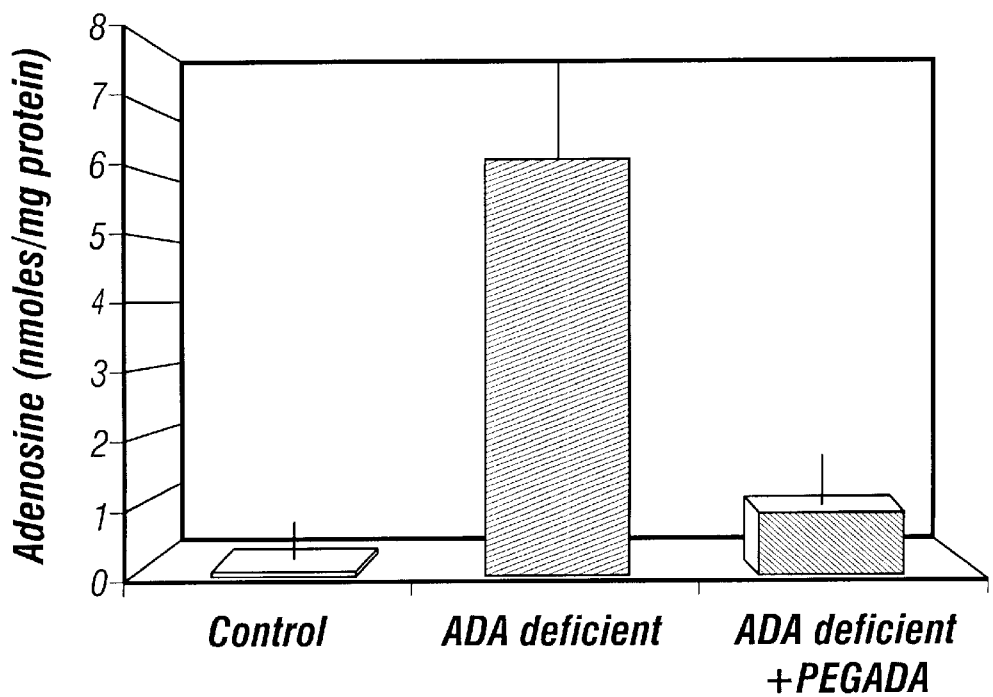

FIG. 5A and FIG. 5B. Reversible lung eosinophilia and lung adenosine levels in ADA deficient mice treated with PEGADA. FIG. 5A, Total cellular differentials of cells collected from BALF of 18-day old control mice (n=19), ADA deficient mice (n=12) and ADA deficient mice treated with PEGADA and examined 72 hours later (n=5). Differentials were determined by counting 200 cells from BALF cytospins of each sample, and multiplying the percentage of each cell type found by the total number of cells in the BALF. Mean values are given as total cells (S.E.M.). FIG. 5B, Adenosine levels were quantitated in the lungs of 18-day old control mice (n=5), ADA deficient mice (n=4), and ADA deficient mice treated with PEGADA and examined 72 hours later (n=4). Mean values are given as nanomoles adenosine per mg protein±S.E.M.

FIG. 6A and FIG. 6B. Levels of serum IgE and BALF cytokines in ADA deficient mice. FIG. 6A, Total IgE levels were measured in the serum of 18-day old control (n=11) and ADA deficient (n=8) mice. Mean values are given as nanogram per ml (S.E.M.). FIG. 6B, The levels of IFNg, IL-4, and IL-5 were measured in BALF collected from 18-day old control (n=10) and ADA deficient (n=7) mice. Mean values are given as picogram per ml. (S.E.M.).

Figure 7A:
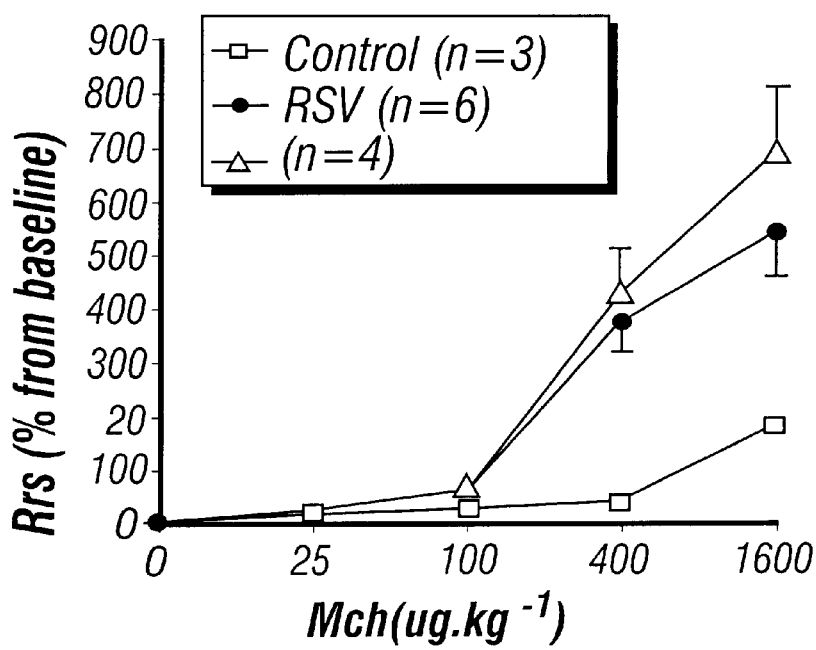
Figure 7B:
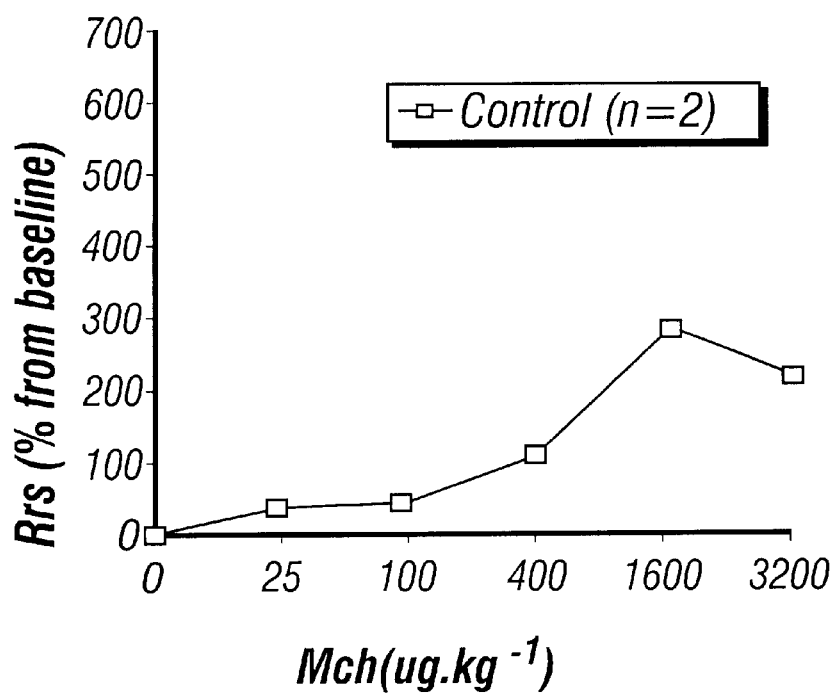

FIG. 7A and FIG. 7B. Airway function analysis following RSV and ovalbumin challenges, and baseline responsiveness in mice heterozygous for the null Ada allele. FIG. 7A, For RSV studies, female BALB/c mice, 6–8 weeks of age, were infected intranasally with RSV while control mice received uninfected media. 6 days post-infection, airway function was measured in response to increasing doses of iv Mch. For ovalbumin, mice were immunized with an intraperitoneal injection of 4 $\mu$g of ovalbumin on protocol days 0 and 14. On days 14, 25, 26, 27 and 28, mice were challenged intranasally with 40 $\mu$l of PBS containing 4$\mu$g of ovalbumin (Zhang et al., 1997). In vivo airway function analysis was performed 24 hours after the last intranasal exposure to antigen. The respiratory resistance (Rrs), used as an index of airway caliber, is obtained as mean±SE and shown as % baseline Rrs. Results are expressed in terms of maximal constrictor response (MR) and ED50 (concentration of Mch that causes 50% of the maximal contractile response). In RSV-infected and ovalbumin challenged animals, the values for ED50 and maximal constrictor response were significantly lower and greater, respectively, when compared to control animals (p<0.05). FIG. 7B, Airway function was also assessed in 6 week old mice heterozygous for the null Ada allele.

4.0 DESCRIPTION OF ILLUSTRATIVE EMBODIMENTS

The present invention provides adenosine deaminase (ADA) deficient mice. Also provided are methods of using the mice as models for the analysis of physiological states that are sensitive to disturbances in adenine nucleoside metabolism. Such physiological states include respiratory disorders such as asthma. Methods include testing suspected respiratory therapeutics. Furthermore, genetic and biochemical compositions for and methods of treating asthma are disclosed. These methods are based on the novel approach disclosed herein of lowering systemic adenosine levels to alleviate asthma. Methods are also included concerning the use of ADA deficient mice to study the mechanism of immunodeficiency that results from the lack of ADA enzyme activity as well as using the mice to test the efficacy of treatment protocols. Additional physiological systems that may be sensitive to the metabolic consequences of ADA deficiency include renal, cardiovascular, neurological, lung development, gastrointestinal tract and bone.

4.1 Knockout Mice

An important aspect of the animal models of the present invention is the lack of ADA expression post-partum. The lack of ADA enzyme activity allows for the accumulation of adenosine and deoxyadenosine. The accumulation of these potent regulatory molecules thus provokes various types of pathophysiological disturbances that are mediated via disturbances in adenosine and deoxyadenosne signaling. One method of inhibiting the endogenous expression of ADA in an animal is to disrupt the gene in germline cells and produce offspring from these cells. This method is generally known as knockout technology.

In a general sense, preparation of a knockout mammal requires first introducing a nucleic acid construct that will be used to suppress expression of a particular gene into an undifferentiated cell type termed an embryonic stem (ES) cell. This cell is then injected into a mammalian embryo, where it hopefully will be integrated into the developing embryo. The embryo is then implanted into a foster mother for the duration of gestation.

U.S. Pat. No. 5,616,491, incorporated herein by reference in its entirety, generally describes the techniques involved in the preparation of knockout mice, and in particular describes mice having a suppressed level of expression of the gene encoding CD28 on T cells, and mice wherein the expression of the gene encoding CD45 is suppressed on B cells. Pfeffer et al. (1993) describe mice in which the gene encoding the tumor necrosis factor receptor p55 has been suppressed. The mice showed a decreased response to tumor necrosis factor signaling. Fung-Leung et al. (1991a; 1991b) describe knockout mice lacking expression of the gene encoding CD8. These mice were found to have a decreased level of cytotoxic T cell response to various antigens and to certain viral pathogens such as lymphocytic choriomeningitis virus.

The term "knockout" refers to a partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of: (1) DNA from some portion of the gene (exon sequence, intron sequence, and/or promoter sequence) to be suppressed; and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA).

The knockout construct nucleic acid sequence may comprise 1) a full or partial sequence of one or more exons and/or introns of the gene to be suppressed, 2) a full or partial promoter sequence of the gene to be suppressed, or 3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

Usually, the DNA to be used in the knockout construct will be one or more exon and/or intron regions, and/or a promoter region from the genomic sequence provided herein, but may also be cDNA sequence. In a preferred embodiment, the DNA to be used in the knockout construct comprises exon 5 of the murine Ada gene (Wakamiya et al., 1995) Generally, the DNA will be at least about 500 bp to 1 kilobase kb) in length, and in certain aspects up to 3–4 kb in length, thereby providing sufficient complementary sequence for hybridization when the knockout construct is introduced into the genomic DNA of the ES cell.

The Ada sequence to be used in producing the knockout construct is digested with a particular restriction enzyme selected to cut at a location(s) such that a new DNA sequence encoding a marker gene can be inserted in the proper position within the Ada DNA sequence. The proper position for marker gene insertion is that which will serve to prevent expression of the native Ada gene; this position will depend on various factors such as the restriction sites in the sequence to be cut, and whether an exon sequence or a promoter sequence, or both is (are) to be interrupted (i.e., the precise location of insertion necessary to inhibit promoter function or to inhibit synthesis of the native exon). Preferably, the enzyme selected for cutting the DNA will generate a longer arm and a shorter arm, where the shorter arm is at least about 300 base pairs (bp). In some cases, it will be desirable to actually remove a portion or even all of one or more exons of the Ada gene so as to keep the length of the knockout construct comparable to the original Ada genomic sequence when the marker gene is inserted in the knockout construct. In these cases, the genomic DNA is cut with appropriate restriction endonucleases such that a fragment of the proper size can be removed.

The marker gene can be any nucleic acid sequence that is detectable and/or assayable, as for example an antibiotic resistance gene such as neo (the neomycin resistance gene) or a gene, such as beta-galactosidase; however typically it is an antibiotic resistance gene or other gene whose expression or presence in the genome can easily be detected. In a preferred embodiment, the marker gene in the neomycin resistance gene. The marker gene is usually operably linked to its own promoter or to another strong promoter from any source that will be active or can easily be activated in the cell into which it is inserted; however, the marker gene need not have its own promoter attached as it may be transcribed using the promoter of the Ada gene to be suppressed. In addition, the marker gene will normally have a polyA sequence attached to the 3' end of the gene; this sequence serves to terminate transcription of the gene.

After the genomic DNA sequence has been digested with the appropriate restriction enzymes, the marker gene sequence is ligated into the genomic DNA sequence using methods well known to the skilled artisan (for example Sambrook et al., 1989). The ends of the DNA fragments to be ligated must be compatible; this is achieved by either cutting all fragments with enzymes that generate compatible ends, or by blunting the ends prior to ligation. Blunting is done using methods well known in the art, such as, for example, by the use of Klenow fragment (DNA polymerase I) to fill in sticky ends. The ligated knockout construct may then be inserted directly into embryonic stem cells.

Embryonic stem cells are typically selected for their ability to integrate into and become part of the germ line of a developing embryo so as to create germ line transmission of the knockout construct. Thus, any ES cell line that is believed to have this capability is suitable for use herein. One mouse strain that is typically used for production of ES cells is the 129J strain. A preferred ES cell line is murine cell line D3 (American Type Culture Collection catalog no. CRL 1934). The cells are cultured and prepared for DNA insertion using methods well known to the skilled artisan such as those set forth by Robertson (1987), Bradley et al. (1986) and Hogan et al. (1986). Insertion of the knockout construct into the ES cells can be accomplished using a variety of methods well known in the art including for example, electroporation, microinjection, and calcium phosphate treatment, as described herein above.

Each knockout construct DNA to be inserted into the cell must first be linearized if the knockout construct has been inserted into a vector. Linearization is accomplished by digesting the DNA with a suitable restriction endonuclease selected to cut only within the vector sequence and not within the knockout construct sequence. For insertion of the DNA sequence, the knockout construct DNA is added to the ES cells under appropriate conditions for the insertion method chosen.

Screening can be done using a variety of methods. Where the marker gene is an antibiotic resistance gene, the cells are cultured in the presence of an otherwise lethal concentration of antibiotic. Those cells that survive have presumably integrated the knockout construct. If the marker gene is other than an antibiotic resistance gene, a Southern blot of the ES cell genomic DNA can be probed with a sequence of DNA designed to hybridize only to the marker sequence. Finally, if the marker gene is a gene that encodes an enzyme whose activity can be detected (e.g., beta-galactosidase), the enzyme substrate can be added to the cells under suitable conditions, and the enzymatic activity can be analyzed.

The knockout construct may be integrated into several locations in the ES cell genome, and may integrate into a different location in each cell's genome, due to the occurrence of random insertion events; the desired location of the insertion is in a complementary position to the Ada DNA sequence to be knocked out. Typically, less than about 1–5 percent of the ES cells that take up the knockout construct will actually integrate the knockout construct in the desired location. To identify those cells with proper integration of the knockout construct, the DNA can be extracted from the cells, and then probed on a Southern blot with a probe or probes designed to hybridize in a specific pattern to genomic DNA digested with one or more particular restriction enzyme(s). Alternatively, or additionally, the genomic DNA can be amplified by PCR™ with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells are inserted into an embryo. Insertion may be accomplished in a variety of ways, however a preferred method is by microinjection. For microinjection, about 10–30 cells are collected into a micropipet and injected into embryos that are at the proper stage of development to integrate the ES cell into the developing embryo. The suitable stage of development for the embryo is very species dependent, however for mice it is about 3.5 days. The embryos are obtained by perfusing the uterus of pregnant females. Suitable methods for accomplishing this are known to the skilled artisan, and are set forth by Bradley (in Robertson, 1987).

While any embryo of the right age/stage of development is suitable for use, preferred embryos are male and have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo is implanted into the uterus of a pseudopregnant foster mother. While any foster mother may be used, they are typically selected for their ability to breed and reproduce well, and for their ability to care for their young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above) has been employed. In addition, or as an alternative, DNA from tail tissue of the offspring may be screened for the presence of the knockout construct using Southern blots and/or PCR™ as described above. Offspring that appear to be mosaics are then crossed to each other if they are believed to carry the knockout construct in their germ line to generate homozygous knockout animals. If it is unclear whether the offspring will have germ line transmission, they can be crossed with a parental or other strain and the offspring screened for heterozygosity. The heterozygotes are identified by Southern blots and/or PCR™ amplification of the DNA, as set forth herein. The heterozygotes can then be crossed with each other to generate homozygous knockout offspring. Homozygotes may be identified by Southern blotting of equivalent amounts of genomic DNA from mice that are the product of this cross, as well as mice that are known heterozygotes and wild type mice. Probes to screen the Southern blots can be designed as set forth above.

Other means of identifying and characterizing the knockout offspring are available. For example, Northern blots can be used to probe the mRNA for the presence or absence of transcripts encoding either the Ada gene knocked out, the marker gene, or both. In addition, western blots can be used to assess the level of expression of the Ada gene knocked out in various tissues of these offspring by probing the Western blot with an antibody against the ADA protein, or an antibody against the marker gene product, where this gene is expressed. In adddition, since Ada is an enxyme, catalytic activity can be directly measured in tissues and cells (Blackburn et al., 1995, 1996, 1998). Finally, in situ analysis (such as fixing the cells and labeling with antibody) and/or FACS (fluorescence activated cell sorting) analysis of various cells from the offspring can be conducted using suitable antibodies to look for the presence or absence of the Ada knockout construct gene product.

As noted in Section 1.2.4, homozygous knockouts of ADA were not viable. Therefore, only heterozygotes or wild-type ADA mice will be born. However, if knockouts are made onto a background containing a transgene comprising an Ada, then the expression of ADA in the placenta will allow mice that are homozygous for disruption of the genomic Ada gene to be born.

4.2 Transgenic Mice

Another important aspect of the present invention is the ability to limit expression of ADA in the placenta, preferably the trophoblasts. The subsequent lack of ADA post-partum leads to the development of asthma and other types of pathophysiology in the transgenic/knockout mice of the present invention. In a general aspect, a transgenic animal is produced by the integration of a given transgene into the genome in a manner that permits the expression of the transgene, or by disrupting the wild-type gene, leading to a knockout of the wild-type gene. Methods for producing transgenic animals are generally described by Wagner and Hoppe (U.S. Pat. No. 4,873,191; which is incorporated herein by reference), Brinster et al. (1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

U.S. Pat. No. 5,639,457 is also incorporated herein by reference to supplement the present teaching regarding transgenic pig and rabbit production. U.S. Pat. Nos. 5,175,384; 5,175,385; 5,530,179, 5,625,125, 5,612,486 and 5,565,186 are also each incorporated herein by reference to similarly supplement the present teaching regarding transgenic mouse and rat production.

Typically, a gene (in the case of some present embodiments, a construction comprising an adenosine deaminase gene) is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. In a particularly preferred embodiment, transgenic mice are generated which only express ADA in the trophoblast cells of the placenta.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA. Other methods for purification of DNA for microinjection are described in Hogan et al. (1986), in Palmiter et al. (1982); in *The Qiagenologist, Application Protocols*, 3rd edition, published by Qiagen, Inc., Chatsworth, Calif.; and in Sambrook et al. (1989).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma).

Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5 % BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5 % avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

4.3 Excision of Transgenes

In certain embodiments of the present invention, rescue of a ADA gene or genetic construct may be desired. The present invention contemplates the use of site-specific recombination systems to rescue specific genes out of a genome, and to excise specific transgenic constructs from the genome.

Members of the integrase family are proteins that bind to a DNA recognition sequence, and are involved in DNA recognition, synapsis, cleavage, strand exchange, and religation. Currently, the family of integrases includes 28 proteins from bacteria, phage, and yeast which have a common invariant His-Arg-Tyr triad (Abremski and Hoess, 1992). Four of the most widely used site-specific recombination systems for eukaryotic applications include: Cre-loxP from bacteriophage P1 (Austin et al., 1981); FLP-FRT from the 2μ plasmid of *Saccharomyces cerevisiae* (Andrews et al., 1985); R-RS from *Zygosaccharomyces rouxii* (Maeser and Kahmann, 1991) and gin-gix from bacteriophage Mu (Onouchi et al., 1995). The Cre-loxP and FLP-FRT systems have been developed to a greater extent than the latter two systems. The R-RS system, like the Cre-loxP and FLP-FRT systems, requires only the protein and its recognition site. The Gin recombinase selectively mediates DNA inversion between two inversely oriented recombination sites (gix) and requires the assistance of three additional factors: negative supercoiling, an enhancer sequence and its binding protein Fis.

The present invention contemplates the use of the Cre/Lox site-specific recombination system (Sauer, 1993, available through Gibco/BRL, Inc., Gaithersburg, Md.) to rescue specific genes out of a genome, and to excise specific transgenic constructs from the genome. The Cre (causes recombination)-lox P (locus of crossing-over(x)) recombination system, isolated from bacteriophage P1, requires only the Cre enzyme and its loxp recognition site on both partner molecules (Sternberg and Hamilton, 1981). The loxp site consists of two symmetrical 13 bp protein binding regions separated by an 8 bp spacer region, which is recognized by the Cre recombinase, a 35 kDa protein. Nucleic acid sequences for loxP (Hoess et al., 1982) and Cre (Sternberg et al., 1986) are known. If the two lox P sites are cis to each other, an excision reaction occurs; however, if the two sites are trans to one another, an integration event occurs. The Cre protein catalyzes a site-specific recombination event. This event is bidirectional, i.e., Cre will catalyze the insertion of sequences at a LoxP site or excise sequences that lie between two LoxP sites. Thus, if a construct for insertion also has flanking LoxP sites, introduction of the Cre protein, or a polynucleotide encoding the Cre protein, into the cell will catalyze the removal of the construct DNA. This technology is enabled in U.S. Pat. No. 4,959,317, which is hereby incorporated by reference in its entirety.

An initial in vivo study in bacteria showed that the Cre excises loxp-flanked DNA extrachromosomally in cells expressing the recombinase (Abremski et al., 1988). A major question regarding this system was whether site-specific recombination in eukaryotes could be promoted by a bacterial protein. However, Sauer (1987) showed that the system excises DNA in *S. cerevisiae* with the same level of efficiency as in bacteria.

Further studies with the Cre-loxP system, in particular the ES cells system in mice, has demonstrated the usefulness of the excision reaction for the generation of unique transgenic animals. Homologous recombination followed by Cre-mediated deletion of a loxp-flanked neo-tk cassette was used to introduce mutations into ES cells. This strategy was repeated for a total of 4 rounds in the same line to alter both alleles of the rep-3 and mMsh2 loci, genes involved in DNA mismatch repair (Abuin and Bradley, 1996). Similarly, a transgene which consists of the 35S promoter/luciferase gene/loxP/35S promoter/hpt gene/loxP ($luc^+hyg^+$) was introduced into tobacco. Subsequent treatment with Cre causes the deletion of the hyg gene ($luc^+hyg^s$) at 50% efficiency (Dale and Ow, 1991). Transgenic mice which have the Ig light chain κ constant region targeted with a loxp-flanked neo gene were bred to Cre-producing mice to remove the selectable marker from the early embryo (Lakso et al., 1996). This general approach for removal of markers stems from issues raised by regulatory groups and consumers concerned about the introduction of new genes into a population.

An analogous system contemplated for use in the present invention is the FLP/FRT system. This system was used to target the histone 4 gene in mouse ES cells with a FRT-flanked neo cassette followed by deletion of the marker by FLP-mediated recombination. The FLP protein could be obtained from an inducible promoter driving the FLP or by using the protein itself (Wigley et al., 1994).

The present invention also contemplates the use of recombination activating genes (RAG) 1 and 2 to excise specific transgenic constructs from the genome, as well as to rescue specific genes from the genome. RAG-1 (GenBank accession number M29475) and RAG-2 (GenBank accession numbers M64796 and M33828) recognize specific recombination signal sequences (RSSs) and catalyze V(D)J recombination required for the assembly of immunoglobulin and T cell receptor genes (Schatz et al., 1989; Oettinger et al., 1990; Cumo and Oettinger, 1994). Transgenic expression of RAG-1 and RAG-2 proteins in non-lymphoid cells supports V(D)J recombination of reporter substrates (Oettinger et al., 1990). For use in the present invention, the transforming construct of interest is engineered to contain flanking RSSs. Following transformation, the transforming construct that is internal to the RSSs can be deleted from the genome by the transient expression of RAG-1 and RAG-2 in the transformed cell.

4.4 Adenosine Receptors and Receptor Agonists and Antagonists

In prefered embodiments of the present inventions, ADA deficient transgenic mice are useful for studying adenosine receptors, including studying and screening for agonists and antagonists of adenosine receptors. Characteristics of adenosine receptors and receptor agonists and antagonists are discussed below.

4.4.1 Adenosine Receptors

The actions of adenosine are mediated through G-protein coupled receptors, the A1, A2a, A2b and A3 adenosine receptors. The adenosine receptors were initially classified into A1 and A2 subtypes on the basis of pharmacological criteria and coupling to adenylate cyclase (Van Caulker et al., 1979). Further pharmacological classification of adenosine receptors prompted subdivision of the A2 class into A2a and A2b subtypes on the basis of high and low affinity, respectively, for adenosine and the agonists NECA and CGS-21680 (Bruns et al., 1986; Wan et al,1990). Molecular cloning and characterization of the human A3 adenosine receptor is described in Salvatore et al., 1993. The existence of A1, A2a, A2b and A3 subtypes has been confirmed by cloning and functional characterization of expressed bovine, canine, rat and human receptors. Cloning and characterization of the human A1, A2a, A2b and A3 receptors are described in GB 2264948-A. Based on the use of these cloned receptors, an assay has been described to identify adenosine receptor agonists and antagonists and determine their binding affinity (see GB 2 264 948 A, published Sep. 15, 1993; see also Bruns et al., 1983; Bruns et al., 1986; Jarvis et al., 1989; Jacobson et al., 1989).

Adenosine exhibits diverse and potent physiological actions in the cardiovascular, nervous, pulmonary, renal and immune systems. Adenosine has been demonstrated to terminate superventricular tachycardia through blockage of atrioventricular nodal conduction (DiMarco et al., 1985; Munoz et al., 1984). Adenosine is a potent vasodilator except in the kidney and placenta (Olsson, 1981). Adenosine produces bronchoconstriction in asthmatics but not in non-asthmatics (Cushly et al., 1984). Adenosine has been implicated as a preventative agent and in treatment of ventricular dysfunction following episodes of regional or global ischemia (Forman and Velasco, 1991) and in cerebral ischemia (Evans et al., 1987; Von Lubitz et al., 1988).

4.4.2 Receptor Agonists and Antagonists

Adenosine receptor agonists, antagonists and binding enhancers have been identified and implicated for usage in the treatment of physiological complications resulting from cardiovascular, pulmonary, renal and neurological disorders. Adenosine receptor agonists have been identified for use as vasodilators, antihypertensive agents (Taylor et al., 1988), and anti-psychotic agents (Heffner et al., 1989). Adenosine receptor agonists have been identified for use in improving renal function (Murray and Churchill, 1985). Adenosine receptor allosteric or binding enhancers have shown utility in the treatment of ischemia, seizures or hypoxia of the brain (Bruns et al., 1990; Janusz et al., 1991).

4.5 Asthma

In preferred embodiments of the present inventions, animals that have lung abnormalities resembling asthma in humans are provided. Characteristics of asthma are discussed below.

4.5.1 The Definition and Prevalence of Asthma

Asthma is a leading cause of morbidity among children in the United States and throughout the world (Gergen et al., 1988; Eggleston and Szefler, 1995), and an estimated 1% of United States health care cost are devoted to asthma treatment (Weiss et al., 1992). In addition, there is convincing evidence to suggest that its prevalence and morbidity are increasing (Evans et al., 1987; National Heart, Lung, and Blood Institute National Asthma Education Program, Expert Panel Report, 1991), despite a better definition of its pathogenesis and increased use of anti-asthma therapy. While the reasons for this increase are not fully understood and probably multifactorial, it has been suggested that environmental factors may play a role in these trends of asthma prevalence and morbidity (Eggleston and Szefler 1995).

Our understanding of the pathogenesis of asthma has changed during the past decades, with the recognition that inflammation underlies the clinical syndrome. Although the relationship between inflammation and clinical symptoms of asthma is not entirely clear, there is evidence that the degree of inflammatory changes within the lung is related to airway hyperresponsiveness (Colasurdo and Larsen, 1995; Barnes, 1995). Furthermore, stimuli capable of increasing airway responsiveness in normal and asthmatic subjects have the ability to produce inflammation within the airways. Because airway hyperresponsiveness is seen even in asymptomatic subjects with mild asthma (Colasurdo and Larsen, 1995), recent work has been aimed at determining if airway inflammation is present when the disease is quiescent. In this respect, analysis of endobronchial biopsies and bronchoalveolar lavages have revealed that subjects with mild asthma often have evidence of inflammation within their lungs (Laitinen et al., 1985; Wardlaw et al., 1988; Beasley et al., 1989; Azzawi et al., 1990). A review of these and other studies by the Expert Panel of the National Heart, Lung and Blood Institute National Education Program (1991) led to the conclusion that airway inflammation is present in virtually all patients with asthma. Superimposed on this chronic inflammatory state are acute inflammatory episodes triggered by several environmental factors which lead to worsening airway hyperresponsiveness and exacerbation of asthma symptoms (Barnes, 1995).

Characterizing asthma as an inflammatory disease has opened the door to extensive research directed at the identification of inflammatory pathways involving many pro-inflammatory molecules including cytokines, chemokines and other signaling molecules (Barnes 1989). Despite the identification of stimuli and the implication of pro-inflammatory signaling molecules, a clear understanding of the ontogeny and mechanisms of asthma is absent. The advances in defining cellular mechanisms involved in asthma and the development of new therapies have been slowed somewhat by the absence of genetic animal models that retain features of lung inflammation and damage seen in asthma patients. As described herein, the inventors have generated a genetic animal model for lung inflammation and damage, and propose methods of studying the role of the signaling molecule, adenosine, in normal lung development and in the predisposition of the lung to inflammation and damage postnatally. Moreover, the animal model of the present invention will allow the determination of how early life genetic and epigenetic factors influence lung inflammation and damage in association with perturbations in adenosine signaling and provide an excellent system for testing new and existing asthma therapies.

4.5.2 Childhood Asthma and Lung Development

There is increasing information to suggest that events that occur during fetal development and early infant growth play a major role in the manifestation of asthma later in life (Barker 1992). In addition, a large number of children suffer from wheezing disorders and asthma (Busse et al., 1995). Despite these observations, little is know about the mechanisms of lung injury during development and infancy. Nor is it known how genetic or epigenetic factors that influence normal lung development and establishment of the immune system, impinge on the development of asthma. This is due in part to the difficulty of studying the lungs of young children. Much could be learned by examining lung development in animal models that demonstrate features of lung inflammation and damage early in life. The present invention provides a mouse model that develops lung inflammation and damage early in life. Furthermore, these animals show signs of abnormal prenatal lung development. They therefore provide the opportunity to monitor changes in the fetal lung that will be associated with lung inflammation and damage during postnatal life.

Lung development in the mouse begins at gestational day 9.5 with the evagination of endodermal epithelial buds from the ventral foregut into the surrounding splanchnic mesoderm. This is followed by a period of rapid growth known as the pseudoglandular stage (gestational day 9.5–16). During this stage branching of the primitive lung epithelium occurs to form the conducting airways and the terminal acinar buds. During the canalicular (gestational days 16–17) and saccular (gestational days 17-term) stages, the terminal buds progressively dilate to form sac-like structures that will form the future alveoli. This is characterized by a thinning of the mesenchyme and a close apposition with blood capillaries (Ten Have-Opbroek, 1991). A number of markers are available for the analysis of various cell types and structures during lung development (Bellusci et al., 1997), which are useful in characterizing phenotypes in the lungs of mice during development.

4.5.3 Environmental Factors and Asthma

Environmental factors can lead to worsening airway hyperresponsiveness and exacerbation of asthma symptoms (Barnes, 1995; Colasurdo and Larsen 1995). In particular, clinical and laboratory observations have repeatedly suggested an association between viral infections and the development of airway dysfunction. Respiratory syncytial virus (RSV) is the most important respiratory pathogen in infants and young children worldwide (Glezen and Denny 1973; Hall, 1992, 94). In the United States, RSV produces yearly outbreaks that cause an estimated 100,000 hospitalizations and 4,500 deaths. Due to the frequency of its epidemics and an incomplete immune response, this agent infects virtually all children in their first year of life (Hall, 1992). Prominent among the clinical features produced by this agent is wheezing in infants as well as exacerbation of asthma in adults and especially children. While several genetic and environmental factors may determine the outcome of RSV infection on airway function (Martinez, 1995; Long, 1995), an association between RSV in early life and long-term pulmonary abnormalities has been suggested (Long, 1995; Burrows, et al., 1977; Welliver et al., 1981; Weiss et al., 1985; Sigurs et al., 1995).

Another important environmental stimulus associated with the development of airway dysfunction and inflammation is represented by allergen sensitization. The ability of allergen exposure to affect the respiratory tract in humans has been studied in terms of both the clinical sequelae in the host (airway obstruction and heightened responsiveness) and in terms of the effects on various lung cells (Platts-Mills et al., 1992; Platts-Mills et al., 1987). Part of the justification for this emphasis is in the observation of Burrows et al (1989) that suggests the prevalence of asthma is closely related to serum IgE standardized for age and sex. Even in children who have been without symptoms throughout their lives and have no history of atopic disease, airway hyperresponsiveness appears to be closely linked to an allergic diathesis, as reflected by the serum total IgE (Sears et al., 1991). While many inflammatory stimuli are associated with increases in responsiveness, allergen exposure is especially important in that the hyperresponsiveness can last for days or months (Colasurdo and Larsen, 1995). Various lung cells and cell products contribute to the clinical and pathological picture of asthma. However, certain cells are likely more central to the pathogenesis of airway inflammation induced by specific stimuli. In this respect, several clinical and laboratory investigations have suggested that complex interactions between T-cells and eosinophils lead to different involvement of cytokines in virus- and allergen-induced airway inflammation (Barnes, 1995).

4.5.4 Histopathology of Asthma in Humans

The most informative and definitive features of asthma are the histopathological findings in the lungs (Nadel and Holtzman 1984; Barnes 1989). Amongst the first histological findings observed in asthma is the infiltration of inflammatory cells into the lung. In particular, an intense inflammatory reaction is seen beneath the basement membrane, where several types of inflammatory cells are often identified, including eosinophils, neutrophils, lymphocytes and degranulating mast cells (Cochrane et al., 1996). Eosinophils and other inflammatory cells are present in sputum and bronchoalveolar lavage of asthmatic individuals (Wardlaw 1988), and blood eosinophilia is often evident (Horn et al., 1975). Other abnormalities found relatively early in asthma are edema of the airway wall, and shedding of airway epithelium (Cochrane et al., 1996). In addition, airways of chronic asthma patients are often obstructed with mucus secretions, cellular debris and inflammatory cells. There is often a thickening of the basement membrane underlying the degenerating airway epithelium accompanied by goblet cell hyperplasia, new vessel formation and vasodilatation, hyperplasia and/or hypertrophy of the airway smooth muscle, mucus gland hypertrophy, and ultimately the development of fibrosis (Cochrane et al., 1996).

4.5.5 Mechanisms of Asthma

Extensive research over the last several decades in the field of immunobiology has identified cells and cellular signals that play major roles in tissue inflammation and injury. A major characteristic of inflammation in asthma is an accumulation of eosinophils in the lung (Bousquet et al., 1990). Eosinophils are also abundant in the peripheral blood and in bronchoalveolar lavage fluid from asthma patients (Wardlaw, 1988; Horn et al., 1975). Other inflammatory cells are also involved, such as mast cells, macrophages, neutrophils and basophils (Barnes, 1989).

Eosinophils are stimulated to differentiate from progenitor cells in response to cytokines that are produced by activated T-helper type 2 cells (Th2 cells), monocytes, macrophages and mast cells. Amongst these cytokines are interleukin-5 (IL-5), IL-4 and granulocyte-macrophage colony-stimulating factor (GM-CSF) (Strek and Leff, 1997). These cytokines are also thought to promote the proliferation of eosinophils, promote chemotaxis and prime them for their response to exogenous stimuli. Once activated, eosinophils themselves release GM-CSF, IL-4 and IL-5 to further promote eosinophil differentiation and proliferation (Strek and Leff, 1997).

Recently, the identification of eosinophilic chemokines has provided new insight into mechanisms to explain the specific recruitment of eosinophils to target tissues such as the lung. These molecules include RANTES (Teran et al., 1996), and eotaxin (Mattoli et al., 1997), both of which have been shown to promote eosinophil chemotaxis in vivo and in vitro. Expression of these molecules are elevated in asthmatic lungs and correlate with an increase in eosinophils (Lilly et al., 1997; Rothenberg et al., 1997).

The transmigration of eosinophils and other inflammatory cells is dependent on interaction of these cells with endothelial matrix molecules such as ICAM-1 (Godding, et al., 1995). Eosinophils infiltrate the interstitial tissues and find their way to smooth muscle, nerves and airway epithelium where, when activated, they release factors such as histamines, degradative enzymes and leukotrienes that influence tissue alterations and damage (Strek and Leff, 1997). The release of histamines, leukotrienes and various cytokines from activated mast cells make them another major player in asthma. In response to IL4, released from activated Th2 cells, B cells produce large amounts of IgE that in turn activate mast cells to release cytokines such as IL-4 and IL-5 that can influence eosinophils (Cochrane et al., 1996, Strek and Leff, 1997). Also, adenosine signaling influences aspects of eosinophil (Kohno et al., 1996), macrophage Najar et al., 1990) and mast cell (Reeves et al., 1997) biology.

4.5.6 Animal Models and Aathma

Because of the limitations on the availability of human tissues, a number of animal models have been developed to better define the structural and functional consequences produced by environmental agents within the respiratory tract (Larsen and Colasurdo, 1997; Abraham and Baugh, 1995). While an ideal animal model should exhibit all the features of human asthma, there is general agreement that a single animal model does not exhibit all the functional and biological changes that would mimic the disease process seen in humans (Larsen and Colasurdo, 1997). Nevertheless, information obtained from these models have provided new insights into human diseases as well as normal mammalian biology.

The mouse model of antigen-driven airway dysfunction has become an important mammalian model for the study of allergen-induced alterations in airway responsiveness. As a result, this species has been the subject of extensive investigations in an attempt to understand the immunopathogenesis of airway inflammation and hyperresponsiveness (Larsen and Colasurdo, 1997). Mice are attractive for these studies because of the extensive knowledge of their immune system, the availability of reagents that allow assessment of the role played by inflammatory cells in the development of airway hyperresponsiveness, and the ability to conduct sophisticated genetic manipulations (see below). Within this species, responsiveness of the airways can be measured by using inhalation challenges or intravenous administrations of agonists such as methacholine followed by the assessment of changes in lung mechanics (Larsen and Colasurdo, 1997). In addition, in vitro studies performed on airway smooth muscle segments have been used to investigate changes in neural control mechanisms produced by allergen sensitization (Larsen and Colasurdo, 1997). Observations in antigen driven mouse models suggest that altered airway function in this model is dependent on CD4+ T-lymphocytes and that eosinophils are the effectors of this response. More recent work using this animal model has provided additional information on the role played by important cells and cell products in the development of inflammation and altered airway function (Zhang et al, 1997; Nakajima et al, 1992; Renz et al, 1992; Brusselle et al, 1994; Kung et al, 1995; Gonzalo et al, 1996; Schwarze et al., 1997). As a result, complex interactions between individual cytokines, eosinophilis and IgE appear to involved in the inflammatory responses within the lung.

Advances in molecular genetics have made it possible to experimentally alter the mammalian genome within the laboratory. Studies in genetically manipulated mice have and will continue to provide a useful means of genetically assessing the role of genes involved in lung development, inflammation and airway disease. Studies in IL-4 deficient mice have suggested that IL-4 is a central mediator of allergic inflammation by regulating antigen-induced eosinophil recruitment into the airways by a T cell dependent mechanisms (Brusselle et al, 1994). Further work by Tang et al (1996), has shown changes in airway physiology and lymphocytic inflammation after overexpression of IL-11 within the lung. And overexpression of signaling molecules in the developing lung have provided new information into the role of growth factors in lung development (Bellusci et al., 1997). Therefore, the use of transgenic and/or knock-out animals are of significant value in discerning the contribution of specific molecules in the development of lung inflammation, injury and remodeling. In an important embodiment of the present invention, the inventors have generated mice that provide the unique opportunity to study prenatal events in the lungs of mice that will develop severe lung eosinophilia and damage early in life.

4.6 Adenosine Signaling in Other Physiologic Systems

In preferred embodiments of the present inventions, ADA deficient transgenic mice are useful for studying adenosine signaling in physiologic systems other than asthma. Adenosine also exerts a marked influence on renal function. Intrarenal infusion of adenosine causes a transient fall in renal blood flow and an increase in renal vascular resistance. With continued infusion of adenosine, renal blood flow returns to control levels and renal vascular resistance is reduced. The initial renal vasoconstrictor responses to adenosine are not due to direct vasoconstrictor actions of the nucleotide, but involve an interaction between adenosine and the renin-angiotensin system.

Adenosine is widely regarded as the primary physiological mediator of reactive hyperemia and autoregulation of the coronary bed in response to myocardial ischemia. It has been reported that the coronary endothelium possesses adenosine $A_2$ receptors linked to adenylate cyclase, which are activated in parallel with increases in coronary flow and that cardiomyocyte receptors are predominantly of the adenosine $A_1$ subtype and associated with bradycardia. Accordingly, adenosine offers a unique mechanism of ischemic therapy. Cardiovascular responses to adenosine are short-lived due to the rapid uptake and metabolism of the endogenous nucleotide. In contrast, the adenosine analogs are more resistant to metabolic degradation and are reported to elicit sustained alterations in arterial pressure and heart rate.

Adenosine acts as a neuromodulator to inhibit neuromal firing and the release of neurotransmitters, as an inhibitor of platelet aggregation, as a cardiac depressant, and as a vasodilator, a vasoconstrictor, as in the renal afferent arterioles and in the skin, as an immunosuppressant, and in a variety of other systems. Most of the physiological effects of adenosine involve binding to discrete membrane-bound adenosine receptors of the A1 or $A_2$ subtypes.

Although adenosine can affect a variety of physiological functions, particular attention has been directed over the years toward actions which might lead to clinical applications. Preeminent has been the cardiovascular effects of adenosine which lead to vasodilation and hypotension but which also lead to cardiac depression. The antilipolytic, antithrombotic, and antispasmodic actions of adenosine have also received some attention. Adenosine stimulates steroidogenesis in adrenal cells, again probably via activation of adenylate cyclase. Adenosine has inhibitory effects on neurotransmission and on spontaneous activity of central neurons. Finally, the bronchoconstrictor action of adenosine and its antagonism by xanthines represents an important area of research.

4.6 Adenosine Deaminase Deficiency

Genetic defects in purine metabolism in humans result in serious metabolic disorders, often with pronounced tissue-specific phenotypes (Blaese, 1995a). A striking example of this is adenosine deaminase (ADA) deficiency, which results in impaired lymphoid development and a severe combined immunodeficiency disease (SCID) (Hershfield and Mitchell, 1995).

ADA deficient SCID was the first of the inherited immunodeficiencies for which the underlying molecular defect was identified (Giblett et al., 1972); however, despite over 20 years of subsequent research, a satisfactory explanation for the lymphoid specificity of this metabolic disease has not emerged. This is largely due to the inaccessibility of human tissue for detailed phenotypic and metabolic analysis and the absence of an animal model which retains features of ADA deficiency in humans.

Additional interest in ADA deficiency stems from recent attempts to use novel therapeutic strategies, including enzyme therapy (Hershfield et al., 1993) and gene therapy (Bordingon et al., 1995; Blaese et al., 1995), to treat the condition in humans. Although the results of these therapeutic approaches are encouraging, unexpected outcomes have raised numerous important questions regarding the efficacy of specific treatment protocols (Hershfield et al., 1993; Blaese, 1995b). The pace with which new enzyme and gene therapy protocols can be tested would be greatly increased by the availability of an animal model for ADA deficiency.

The availability of a genetic animal model for ADA deficiency would make possible a wide range of biochemical and immunological experiments that are not permissible with humans.

Attempts to generate ADA deficient mice were initially reported by two groups (Wakamiya et al., 1995; Migchielsen et al., 1995), resulting in animals with independent sites of Ada gene disruption. However, these attempts did not lead to the production of viable ADA deficient mice. In each case a similar phenotype was observed. ADA deficient fetuses died perinatally due to severe liver damage (Wakamiya et al., 1995; Migchielsen et al., 1995). This phenotype was accompanied by profound disturbances in purine metabolism, including marked increases in the ADA substrates adenosine and 2'-deoxyadenosine.

2'-Deoxyadenosine is a cytotoxic metabolite that can kill cells through mechanisms that include disturbances in deoxynucleotide metabolism (Ullmann et al., 1978; Cohen et al., 1978) and the inhibition of cellular transmethylation reactions (Hershfield, 1979; Hershfield et al., 1979). ADA deficient fetuses exhibited evidence for both of these mechanisms of 2'-deoxyadenosine cytotoxicity, in that levels of the 2'-deoxyadenosine metabolite, dATP, were markedly elevated, and the enzyme S-adenosylhomocysteine (AdoHcy) hydrolase was inhibited (Wakamiya et al., 1995; Migchielsen et al., 1995). These metabolic disturbances are thought to contribute to the liver damage and subsequent death of ADA deficient fetuses.

4.8 Pharmacuetical Compositions

In preferred embodiments of the present invention, compositions and methods for the reduction in systemic or local adenosine levels in an animal are provided. In preferred embodiments, the pharmaceutical compositions comprise an ADA polypeptide or an active fragment thereof. In a more preferred embodiment the ADA polypeptide is conjugated to polyethylene glycol (PEG). In other embodiments, the pharmaceutical compositions contain nucleic acids comprising an ADA gene. Of course, the composition may comprise one or more other compounds in place of or in addition to ADA that are capable of metabolizing adenosine or reducing the systemic level of adenosine in the subject. One such compound may be a bacterial nucleoside phosphorylase enzyme or its respective gene.

Methods for administering therapeutic polypeptide compositions to animals or asthma patients is provided by U.S. Pat. No. 5,730,983 and is incorporated herein in its entirety. U.S. Pat. No. 5,730,983 discloses methods of administering ICAM-1 molecules to asthma patients.

In providing a patient with polypeptides, or functional fragments thereof, capable of reducing systemic adenosine levels, the dosage of administered agent will vary depending upon such factors as the patient's age, weight, height, sex, general medical condition, previous medical history, etc. In general, it is desirable to provide the recipient with a dosage of agent which is in the range of from about 1 pg/kg to 10 mg/kg (body weight of patient), although a lower or higher dosage may be administered.

The anti-asthma agents of the present invention are intended to be provided to recipient subjects in an amount sufficient to lessen or attenuate the severity, extent or duration of the asthma symptoms. The ADA polypeptides of the invention, or functioanl equivalents thereof, may be administered either alone or in combination with one or more additional anti-asthma agents (such as methylxanthines (such as theophylline), beta-adrenergic agonists (such as catecholamines, resorcinols, saligenins, and ephedrine), glucocorticoids (such as hydrocortisone), chromones (such as cromolyn sodium) and anticholinergics (such as attopine), or any other asthma agent, in order to decrease the amount of such agents needed to treat the asthma symptoms. As used herein, one compound is said to be additionally administered with a second compound when the administration of the two compounds is in such proximity of time that both compounds can be detected at the same time in the patient's serum.

The administration of the agent(s) of the invention may be for either a "prophylactic" or "therapeutic" purpose. When provided prophylactically, the agent(s) are provided in advance of any asthma symptom. The prophylactic administration of the agent(s) serves to prevent or attenuate any subsequent asthmatic response. When provided therapeutically, the agent(s) are provided at (or shortly after) the onset of a symptom of asthma. The therapeutic administration of the compound(s) serves to attenuate any actual asthmatic episode. The agents of the present invention may, thus, be provided either prior to the onset of an anticipated asthmatic episode (so as to attenuate the anticipated severity, duration or extent of the episode) or after the initiation of the episode.

Additional pharmaceutical methods may be employed to control the duration of action. Control release preparations may be achieved through the use of polymers to complex or absorb ADA polypeptides, or their functional equivalents. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate ADA polypeptides, or functional equivalents, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gel amine-microcapsules and poly (methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980) and are disclosed in Section 4.5.2 herein.

4.8.1 Pharmaceutically Acceptable Carriers

Aqueous compositions of the present invention comprise an effective amount of the ADA polypeptide dissolved or dispersed in a pharmaceutically acceptable carrier or aqueous medium. Aqueous compositions of gene therapy vectors expressing an ADA polypeptide are also contemplated. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains an ADA polypeptide or ADA encoding gene composition as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. In a preferred embodiment, the ADA polypeptide is conjugated to PEG. Under ordinary conditions of storage and use, these preparations contain a preservative to prevent the growth of microorganisms.

An ADA polypeptide or ADA polypeptide encoding gene composition can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In terms of using peptide therapeutics as active ingredients, the technology of U.S. Pat. Nos. 4,608,251; 4,601,903; 4,599,231; 4,599,230; 4,596,792; and 4,578,770, each incorporated herein by reference, may be used.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

The active ADA polypeptides or agents may be formulated within a therapeutic mixture to comprise about 0.0001 to 1.0 milligrams, or about 0.001 to 0.1 milligrams, or about 0.1 to 1.0 or even about 10 milligrams per dose or so. In preferred embodiments, the active ADA polypeptides or agents are formulated within a therapeutic mixture to comprise about 0.001 to about 1 milligram. Multiple doses can also be administered In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5.

In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Additional formulations which are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids.

In general, for suppositories, traditional binders and carriers may include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

4.8.2 Liposomes and Nanocapsules

In certain embodiments, the inventors contemplate the use of liposomes and/or nanocapsules for the introduction of ADA compositions into host cells. ADA compositions may comprise active ADA polypeptides or ADA nucleic acid compositions encoding active ADA polypeptides. Such formulations may be preferred for the introduction of pharmaceutically-acceptable formulations of the polypeptides or pharmaceuticals disclosed herein. The formation and use of liposomes is generally known to those of skill in the art (see for example, Couvreur et al., 1977 which describes the use of liposomes and nanocapsules in the targeted antibiotic therapy of intracellular bacterial infections and diseases). More recently, liposomes were developed with improved serum stability and circulation half-times (Gabizon and Papahadjopoulos, 1988; Allen and Choun, 1987).

Liposomes are vesicular structures characterized by a phospholipid bilayer membrane and an inner aqueous medium. Multilamellar liposomes have multiple lipid layers separated by aqueous medium. The term "liposome" is intended to mean a composition arising spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 $\mu$m. Sonication of MLVs results in the formation of small unilamellar vesicles (SUVs) with diameters in the range of 200 to 500 Å, containing an aqueous solution in the core.

The following information may also be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way (Henry-Michelland et al., 1987). To avoid side effects due to intracellular polymeric overloading, such ultrafine particles (sized around 0.1 $\mu$m) should be designed using polymers able to be degraded in vivo. Biodegradable polyalkyl-cyano-acrylate nanoparticles that meet these requirements are contemplated for use in the present invention, and such particles may be are easily made, as described (Couvreur et al., 1977; 1988). Methods of preparing polyalkyl-cyano-acrylate nanoparticles containing biologically active substances and their use are described in U.S. Pat. Nos. 4,329,332, 4,489,055, and 4,913,908.

Pharmaceutical compositions containing nanocapsules for the oral delivery of active agents are described in U.S. Pat. Nos. 5,500,224 and 5,620,708. U.S. Pat. No. 5,500,224 describes a pharmaceutical composition in the form of a colloidal suspension of nanocapsules comprising an oily phase consisting essentially of an oil containing dissolved therein a surfactant and suspended therein a plurality of nanocapsules having a diameter of less than 500 nanometers. U.S. Pat. No. 5,620,708 describes compositions and methods for the oral administration of drugs and other active agents. The compositions comprise an active agent carrier particle attached to a binding moiety which binds specifically to a target molecule present on the surface of a mammalian enterocyte. The binding moiety binds to the target molecule with a binding affinity or avidity sufficient to initiate endocytosis or phagocytosis of the particulate active agent carrier so that the carrier will be absorbed by the enterocyte. The active agent will then be released from the carrier to the host's systemic circulation. In this way, degradation of degradation-sensitive drugs, such as polypeptides, in the intestines can be avoided while absorption of proteins and polypeptides form the intestinal tract is increased.

U.S. Pat. Nos. 5,641,515 and 5,698,515 describe the use of nanocapsules for the oral administration of a polypeptide, specifically, insulin and are incorporated herein by reference. U.S. Pat. No. 5,698,515 described insulin containing nanocapsules intended for oral administration of insulin which comprises a hydrophilic polymer modified with an inhibitor of proteolytic enzyme, insulin and water, wherein the inhibitor of proteolytic enzymes is ovomucoid isolated from duck or turkey egg whites. U.S. Pat. No. 5,556,617 describes the use of nanoparticles as pharmaceutical treatment of the upper epidermal layers by topical application on the skin.

Poly(alkyl cyanoacrylate) nanocapsules have been used as biodegradable polymeric drug carriers for subcutaneous and peroral delivery of octreotide, a long-acting somatostatin analogue. The nanocapsules, prepared by interfacial emulsion polymerization of isobutyl cyanoacrylate, were 216 nm in diameter and incorporated 60% of octreotide. Nanocapsules were administered subcutaneously and the octreotide-loaded nanocapsules (20 mg/kg) suppressed the insulinaemia peak induced by intravenous glucose overload and depressed insulin secretion over 48 h. When administered perorally to oestrogen-treated rats, octreotide loaded nanocapsules (200 and 100 mg/kg) significantly improved the reduction of prolactin secretion and slightly increased plasma octreotide levels (Damge et al, 1997).

The negative surface charge of nanocapsules makes them particularly susceptible to lysozyme (LZM), a positively-charged enzyme that is highly concentrated in mucosas. This interaction causes destabilization of the nanocapsule by LZM; however, it was observed that the destabilizing effects caused by the adsorption of LZM onto the nanocapsules can be prevented by previous adsorption of the cationic poly (amino acid) poly-L-lysine (Calvo et al., 1997).

Calvo et al., 1996 describe the use of poly-epsilon-caprolactone (PECL) microparticles for the ocular bioavailability of drugs. Their study showed that PECL nanoparticles and nanocapsules as well as submicron emulsions are shown to be novel corneal drug carriers, and represent a useful approach for increasing the ocular bioavailability of drugs.

An excellent review of nanoparticles and nanocapsular carriers is provided by Arshady (1996). Arshady notes that one of the major obstacles to the targeted delivery of colloidal carriers, or nanocapsules, is the body's own defense mechanism in capturing foreign particles by the reticuloendothelial system (RES). This means that following intravenous administration, practically all nanometer size particles are captured by the RES (mainly the liver). The review describes recent initiatives on the design of macromolecular homing devices which seem to disguise nanoparticles from the RES and, hence, are of potential interest to the targeted delivery of nanocapsular carriers. The idea is based on a graft copolymer model embodying a link site for attachment to the carrier, a floating pad for maintaining the particles afloat in the blood stream, an affinity ligand for site-specific delivery and a structural tune for balancing the overall structure of the homing device.

Yu and Chang, 1996 describe the use of nanocapsules containing hemoglobin as potential blood substitutes. They use different polymers including polylactic acid and polyisobutyl-cyanoacrylate and modify the surface of the nanocapsules with polyethylene glycol (PEG) or with PEG 2000 PE. The surface modified nanocapsules containing hemoglobin survive longer in the circulation.

U.S. Pat. No. 5,451,410 describes the use of modified amino acid for the encapsulation of active agents. Modified amino acids and methods for the preparation and used as oral delivery systems for pharmaceutical agents are described. The modified amino acids are preparable by reacting single amino acids or mixtures of two or more kinds of amino acids with an amino modifying agent such as benzene sulfonyl chloride, benzoyl chloride, and hippuryl chloride. The modified amino acids form encapsulating microspheres in the presence of the active agent under sphere-forming conditions. Alternatively, the modified amino acids may be used as a carrier by simply mixing the amino acids with the active agent. The modified amino acids are particularly useful in delivering peptides, e.g., insulin or calmodulin, or other agents which are sensitive to the denaturing conditions of the gastrointestinal tract.

4.8.3 Kits

Therapeutic kits of the present invention are kits comprising a ADA protein, polypeptide, gene, vector or other adenosine effector. Such kits will generally contain, in suitable container means, a pharmaceutically acceptable formulation of a ADA protein, polypeptide, domain, or a gene or vector expressing any of the foregoing in a pharmaceutically acceptable formulation. The kit may have a single container means, or it may have distinct container means for each compound.

When the components of the kit are provided in one or more liquid solutions, the liquid solution is an aqueous solution, with a sterile aqueous solution being particularly preferred. The ADA compositions may also be formulated into a syringeable composition. In which case, the container means may itself be a syringe, pipette, or other such like apparatus, from which the formulation may be applied to an infected area of the body, injected into an animal, or even applied to and mixed with the other components of the kit.

The components of the kit may be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the ADA polypeptide, gene or adenosine inhibitory formulation are placed, preferably, suitably allocated. The kits may also comprise a second container means for containing a sterile, pharmaceutically acceptable buffer or other diluent.

The kits of the present invention will also typically include a means for containing the vials in close confinement for commercial sale, such as, e.g., injection or blow-molded plastic containers into which the desired vials are retained.

Irrespective of the number or type of containers, the kits of the invention may also comprise, or be packaged with, an instrument for assisting with the injection/administration or placement of the ultimate ADA polypeptide or gene composition within the body of an animal. Such an instrument may be a syringe, pipette, forceps, or any such medically approved delivery vehicle.

4.9 ADA Nucleic Acids
4.9.1 Genes and DNA Segments

Important aspects of the present invention concern isolated DNA segments and recombinant vectors encoding one or more ADA polypeptides, and the creation and use of recombinant host cells through the application of DNA technology, that express one or more ADA polypeptides, using the sequences of mouse (GenBank accession number M10319; SEQ ID NO:1) or human (GenBank accession number M13792; Wiginton et al., 1986; SEQ ID NO:3) ADA genes, or functional equivalents thereof.

The present invention concerns DNA segments, isolatable from mammalian and human cells, that are free from total genomic DNA and are capable of conferring adenosine deaminase activity to a recombinant host cell when incorporated into the recombinant host cell. As used herein, the term adenosine deaminase activity indicates the ability to catabolize adenosine or deoxyadenosine to inosine or deoxyinosine, respectively.

As used herein, the term "DNA segment" refers to a DNA molecule that has been isolated free of total genomic DNA of a particular species. Therefore, a DNA segment encoding ADA refers to a DNA segment that contains coding sequences of ADA, yet is isolated away from, or purified free from, total mammalian or human genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified Ada gene refers to a DNA segment including any of the Ada gene coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and smaller engineered gene segments that express, or may be adapted to express, proteins, polypeptides, domains, peptides or fusion proteins.

"Isolated substantially away from other coding sequences" means that the gene of interest, in this case any Ada gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode an ADA polypeptide that includes within its amino acid sequence a contiguous amino acid sequence of the mouse (GenPept accession number 309091; SEQ ID NO:2) or human (GenPept accession number 178077; SEQ ID NO:4) ADA polypeptides, or functional equivalents thereof.

Naturally, where the DNA segment or vector encodes an ADA polypeptide, or is intended for use in expressing the ADA polypeptide, the most preferred sequences are those that are essentially as set forth in the contiguous sequence of SEQ ID NO:1 or SEQ ID NO:3, and that encode a protein that retains adenosine deaminase activity, e.g., as may be determined by the an adenosine deaminase assay (Winston et al, 1992).

Sequence of an ADA polypeptide will substantially correspond to a contiguous portion of that shown in SEQ ID NO:2 or SEQ ID NO:4, and have relatively few amino acids that are not identical to, or a biologically functional equivalent of, the amino acids shown in SEQ ID NO:2 or SEQ ID NO:4. The term "biologically functional equivalent" is well understood in the art and is further defined in detail herein.

Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:2 or SEQ ID NO:4 will be sequences that are "essentially as set forth in SEQ ID NO:2 or SEQ ID NO:4.

In certain other embodiments, the invention concerns isolated DNA segments and recombinant vectors that include within their sequence a contiguous nucleic acid sequence from that shown in SEQ ID NO:1 or SEQ ID NO:3. This definition is used in the same sense as described above and means that the nucleic acid sequence substantially corresponds to a contiguous portion of that shown in SEQ ID NO:1 or SEQ ID NO:3 and has relatively few codons that are not identical, or functionally equivalent, to the codons of SEQ ID NO:1 or SEQ ID NO:3. Again, DNA segments that encode proteins exhibiting adenosine deaminase activity will be most preferred. The term "functionally equivalent codon" is used herein to refer to codons that encode the same amino acid, such as the six codons for arginine or serine, and also refers to codons that encode biologically equivalent amino acids. See Table 1 below, which lists the codons preferred for use in humans, with the codons listed in decreasing order of preference from left to right in the table (Wada et al., 1990). Codon preferences for other organisms are also well known to those of skill in the art (Wada et al., 1990, included herein in its entirety by reference).

TABLE 1

Preferred Human DNA Codons

| Amino Acids | | | Codons |
|---|---|---|---|
| Alanine | Ala | A | GCC GCT GCA GCG |
| Cysteine | Cys | C | TGC TGT |
| Aspartic acid | Asp | D | GAC GAT |
| Glutamic acid | Glu | E | GAG GAA |
| Phenylalanine | Phe | F | TTC TTT |
| Glycine | Gly | G | GGC GGG GGA GGT |
| Histidine | His | H | CAC CAT |
| Isoleucine | Ile | I | ATC ATT ATA |
| Lysine | Lys | K | AAG AAA |
| Leucine | Leu | L | CTG CTC TTG CTT CTA TTA |
| Methionine | Met | M | ATG |
| Asparagine | Asn | N | AAC AAT |
| Proline | Pro | P | CCC CCT CCA CCG |
| Glutamine | Gln | Q | CAG CAA |
| Arginine | Arg | R | CGC AGG CGG AGA CGA CGT |
| Serine | Ser | S | AGC TCC TCT AGT TCA TCG |
| Threonine | Thr | T | ACC ACA ACT ACG |
| Valine | Val | V | GTG GTC GTT GTA |
| Tryptophan | Trp | W | TGG |
| Tyrosine | Tyr | Y | TAC TAT |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have between about 70% and about 79%; or more preferably, between about 80% and about 89%; or even more preferably, between about 90% and about 99% of nucleotides that are identical to the nucleotides shown in the sequences of SEQ ID NO:1 or SEQ ID NO:3 will be sequences that are "essentially as set forth in SEQ ID NO:1 or SEQ ID NO:3". Sequences that are essentially the same as those set forth in SEQ ID NO:1 or SEQ ID NO:3 may also be functionally defined as sequences that are capable of hybridizing to a nucleic acid segment containing the complement of SEQ ID NO:1 or SEQ ID NO:3 under relatively stringent conditions. Suitable relatively stringent hybridization conditions will be well known to those of skill in the art.

Naturally, the present invention also encompasses DNA segments that are complementary, or essentially complementary, to the sequence set forth in SEQ ID NO:1 or SEQ ID NO:3. Nucleic acid sequences that are "comple-mentary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 or SEQ ID NO:3 under relatively stringent conditions.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch identical to or complementary to the sequence shown in SEQ ID NO:1 or SEQ ID NO:3, such as about 14 nucleotides, and that are up to about 10,000 or about 5,000 base pairs in length, with segments of about 3,000 being preferred in certain cases. DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

The various probes and primers designed around the nucleotide sequences of the present invention may be of any length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

It will also be understood that this invention is not limited to the particular nucleic acid and amino acid sequences of SEQ ID NO:1, SEQ ID NO:2, SEQ ID NO:3, or SEQ ID NO:4. Recombinant vectors and isolated DNA segments may therefore variously include the ADA coding regions themselves, coding regions bearing selected alterations or modifications in the basic coding region, or they may encode larger polypeptides that nevertheless include ADA-coding regions or may encode biologically functional equivalent proteins or peptides that have variant amino acids sequences.

The DNA segments of the present invention encompass biologically functional equivalent ADA proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test ADA mutants in order to examine adenosine deaminase activity at the molecular level.

If desired, one may also prepare fusion proteins and peptides, e.g., where the ADA coding regions are aligned within the same expression unit with other proteins or peptides having desired functions, such as for purification or immunodetection purposes (e.g., proteins that may be purified by affinity chromatography and enzyme label coding regions, respectively).

Encompassed by certain embodiments of the present invention are DNA segments encoding relatively small peptides, such as, for example, peptides of from about 15 to about 50 amino acids in length, and more preferably, of from about 15 to about 30 amino acids in length; and also larger polypeptides up to and including proteins corresponding to the fill-length sequences set forth in SEQ ID NO:2 or SEQ ID NO:4.

4.9.2 Nucleic Acid Detection

In addition to their use in directing the expression of the ADA proteins, the nucleic acid sequences disclosed herein also have a variety of other uses. For example, they may be used as probes or primers to detect the presence of an Ada gene in a sample.

4.9.2.1 Hybridization

The use of a hybridization probe of between 17 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of nucleotides by site-directed mutagenesis, it is appreciated that lower stringency conditions are required. Under these conditions, hybridization may occur even though the sequences of probe and target stand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

4.9.2.2 Amplification and PCR™

Nucleic acids used as a template for amplification are isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to Ada are contacted with the isolated nucleic acid under conditions that permit selective hybridization. The term "primer", as defined herein, is meant to encompass any nucleic acid that is capable of priming the synthesis of a nascent nucleic acid in a template-dependent process.

Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and each incorporated herein by reference in entirety.

Briefly, in PCR™, two or more primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., PCT Application WO 88/10315, incorporated herein by reference. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al, PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: *PCR Protocols: A Guide To Methods And Applications,* Academic Press, N.Y., 1990 incorporated by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al, 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose or nylon, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

4.9.3 Recombinant Vectors, Host Cells and Expression

Recombinant vectors form important further aspects of the present invention. The term "expression vector or construct" means any type of genetic construct containing a nucleic acid coding for a gene product in which part or all of the nucleic acid encoding sequence is capable of being transcribed and subsequently translated.

Particularly useful vectors are contemplated to be those vectors in which the coding portion of the DNA segment, whether encoding a full length protein or smaller peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control", "operably linked to" or "under transcriptional control" means that the promoter is in the correct location and orientation in relation to the nucleic acid to control RNA polymerase initiation and expression of the gene.

The promoter may be in the form of the promoter that is naturally associated with any of the Ada genes, as may be obtained by isolating the 5' non-coding sequences located upstream of the coding segment or exon, for example, using recombinant cloning and/or PCR technology, in connection with the compositions disclosed herein (PCR technology is disclosed in U.S. Pat. Nos. 4,683,202 and 4,683,195, each incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with an Ada gene in its natural environment. Such promoters may include promoters normally associated with other genes, and/or promoters isolated from any other bacterial, viral, eukaryotic, or mammalian cell.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989), incorporated herein by reference. The promoters employed may be constitutive, or inducible, and can be used under the appropriate conditions to direct high level expression of the introduced DNA segment, such as is advantageous in the large-scale production of recombinant proteins or peptides.

At least one module in a promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Preferred promoters include those derived from HSV, including the HNF1α promoter. Another preferred embodiment is a tetracycline controlled promoter.

Of course, to limit expression of an Ada gene to the placenta, one would want to use a promoter that is expressed in the placenta but not in the tissues of the fetus or neonatal mouse. In preferred embodiments, such a promoter comprises a trophoblast regulatory element (Shi et al., 1997).

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. Tables 2 and 3 below list several enhancers, promoters and inducible elements which may be employed, in the context of the present invention, to regulate the expression of any of the Ada constructs. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which serves as a binding region for one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 2

Promoter and Enhancer Elements

| Promoter/Enhancer | References |
| --- | --- |
| Immunoglobulin Heavy Chain | Banerji et al., 1983; Gilles et al., 1983; Grosschedl and Baltimore, 1985; Atchinson and Perry, 1986, 1987; Imler et al., 1987; Weinberger et al., 1984; Kiledjian et al., 1988; Porton et al.; 1990 |
| Immunoglobulin Light Chain | Queen and Baltimore, 1983; Picard and Schaffner, 1984 |
| T-Cell Receptor | Luria et al., 1987; Winoto and Baltimore, 1989; Redondo et al.; 1990 |
| HLA DQ a and DQ β | Sullivan and Peterlin, 1987 |
| β-Interferon | Goodbourn et al., 1986; Fujita et al., 1987; Goodbourn and Maniatis, 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Shennan et al., 1989 |
| β-Actin | Kawamoto et al., 1988; Ng et al.; 1989 |
| Muscle Creatine Kinase | Jaynes et al., 1988; Horlick and Benfield, 1989; Johnson et al., 1989 |
| Prealbumin (Transthyretin) | Costa et al., 1988 |
| Elastase I | Ornitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987; Tronche et al., 1989, 1990 |
| α-Fetoprotein | Godbout et al., 1988; Campere and Tilghman, 1989 |

TABLE 2-continued

Promoter and Enhancer Elements

| Promoter/Enhancer | References |
|---|---|
| t-Globin | Bodine and Ley, 1987; Perez-Stable and Constantini, 1990 |
| β-Globin | Trudel and Constantini, 1987 |

TABLE 2

Promoter and Enhancer Elements

| Promoter/Enhancer | References |
|---|---|
| e-fos | Cohen et al., 1987 |
| c-HA-ras | Triesman, 1985; Deschamps et al., 1985 |
| Insulin | Edlund et al., 1985 |
| Neural Cell Adhesion Molecule (NCAM) | Hirsh et al., 1990 |
| α$_1$-Antitrypain | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987; Schaffner et al., 1988 |

TABLE 2-continued

Promoter and Enhancer Elements

| Promoter/Enhancer | References |
|---|---|
| Polyoma | Swartzendruber and Lehman, 1975; Vasseur et al., 1980; Katinka et al., 1980, 1981; Tyndall et al., 1981; Dandolo et al., 1983; de Villiers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Choi et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987; Stephens and Hentschel, 1987; Gius et al, 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rosen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukernia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Ponta et al., 1985; Sakai et al., 1988 |
| β-Interferon | poly(rI)x poly(rc) | Tavernier et al., 1983 |
| Adenovirus 5 E2 | Ela | Imperiale and Nevins, 1984 |
| Collagenase | Phorbol Ester (TPA) | Angel et al., 1987a |
| Stromelysin | Phorbol Bster (TPA) | Angel et al., 1987b |
| SV40 | Phorbol Ester (TPA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | Ela, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone a Gene | Thyroid Hormone | Chatterjee et al., 1989 |

Turning to the expression of ADA polypeptides, once a suitable clone or clones have been obtained, whether they be cDNA based or genomic, one may proceed to prepare an expression system. The engineering of DNA segment(s) for expression in a prokaryotic or eukaryotic system may be performed by techniques generally known to those of skill in recombinant expression. It is believed that virtually any expression system may be employed in the expression of the proteins of the present invention.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

In expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. It is known that the primary sequence surrounding the ATG initiation codon GCC($^A_G$)CCATGG is the optimal context for initiation of translation in higher eukaryotes (Kozak 1991). Thus mutagenesis of the sequence surrounding the ATG codon may be mutated, as described in detail herein, is contemplated by the inventors as a mechanism to improve the efficiency of translation of the Ada constructs of the present invention.

As used herein, the terms "engineered" and "recombinant" cells are intended to refer to a cell into which an exogenous DNA segment or gene, such as a cDNA or gene encoding an ADA polypeptide has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant ADA protein, whether mutant or wild-type, in accordance with the present invention one would prepare an expression vector that comprises a ADA-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis;* and other enterobacteriaceae such as *Salmonella typhimurium, Serratia marcescens,* and various Pseudomonas species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy means for identifying transformed cells. The pBR322 derived plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

The following details concerning recombinant protein production in bacterial cells, such as *E. coli,* are provided by way of exemplary information on recombinant protein production in general, the adaptation of which to a particular recombinant expression system will be known to those of skill in the art.

Bacterial cells, for example, *E. coli,* containing the expression vector are grown in any of a number of suitable media, for example, LB. The expression of the recombinant protein may be induced, e.g., by adding IPTG to the media or by switching incubation to a higher temperature, depending on the particular promoter construct employed. After culturing the bacteria for a further period, generally of between 2 and 24 hours, the cells are collected by centrifugation and washed to remove residual media.

The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g 8M) or chaotropic agents such as guanidine hydrochloride in the presence of reducing agents, such as β-mercaptoethanol or DTT (dithiothreitol).

Under some circumstances, it may be advantageous to incubate the protein for several hours under conditions suitable for the protein to undergo a refolding process into a conformation which more closely resembles that of the native protein. Such conditions generally include low protein concentrations, less than 500 mg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE, or with antibodies specific for the native molecule (which can be obtained from animals vaccinated with the native molecule or smaller quantities of recombinant protein). Following refolding, the protein can then be purified further and separated from the refolding mixture by chromatography on any of several supports including ion exchange resins, gel permeation resins or on a variety of affinity columns.

For expression in Saccharomyces, the plasmid YRp7, for example, is commonly used. This plasmid already contains the trp1 gene which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase-2, isocytochrome-C, acid phosphatase, degradative enzymes associated with nitrogen metabolism, and the aforementioned glyceraldehyde-3-phosphate dehydrogenase, and enzymes responsible for maltose and galactose utilization, such as the well known GAL1-10 promoter.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more ADA protein coding sequences.

In a useful insect system, *Autograph californica* nuclear polyhedrosis virus (AcNPV) is used as a vector to express foreign genes. The virus grows in *Spodoptera frugiperda* cells. The ADA coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g. U.S. Pat. No. 4,215,051, Smith, incorporated herein by reference).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein.

Expression vectors for use in mammalian such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired Ada gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing any of the ADA protein isoforms in infected hosts.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant ADA polypeptides, stable expression is preferred. For example, cell lines that stably express constructs encoding ADA may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited to the herpes simplex virus thymidine kinase (tk), hypoxanthine-guanine phosphoribosyltransferase (hgprt) and adenine phosphoribosyltransferase (aprt) genes, in tk-, hgprt- or aprt- cells, respectively. Also, antimetabolite resistance can be used as the basis of selection for dihydrofolate reductase (dhfr), that confers resistance to methotrexate; gpt, that confers resistance to mycophenolic acid; neo, that confers resistance to the aminoglycoside G-418; and hygro, that confers resistance to hygromycin.

It is contemplated that the ADA polypeptides may be "overexpressed", i.e., expressed in increased levels relative to its natural expression in cells. Such overexpression may be assessed by a variety of methods, including radiolabeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural cells is indicative of overexpression, as is a relative abundance of the specific protein in relation to the other proteins produced by the host cell and, e.g., visible on a gel.

4.9.4 Use of Cells in Bioreactors

In an important embodiment of the present invention, ADA polypeptides are administered to an animal with asthma and this administration alleviates the condition in these animals. Therefore, the ability to produce biologically active ADA polypeptides is important to the present invention.

Over the last decade, advances in biotechnology have led to the production of important proteins and factors from bacteria, yeast, insect cells and from mammalian cell culture. Mammalian cultures have advantages over cultures derived from the less advanced lifeforms in their ability to post-translationally process complex protein structures such as disulfide-dependent folding and glycosylation. Indeed, mammalian cell culture is now the preferred source of a number of important proteins for use in human and animal medicine, especially those which are relatively large, complex or glycosylated.

Development of mammalian cell culture for production of pharmaceuticals has been greatly aided by the development in molecular biology of techniques for design and construction of vector systems highly efficient in mammalian cell cultures, a battery of useful selection markers, gene amplification schemes and a more comprehensive understanding of the biochemical and cellular mechanisms involved in procuring the final biologically-active molecule from the introduced vector.

However, the traditional selection of cell types for expressing heterologous proteins has generally been limited to the more "common" cell types such as CHO cells, BHK cells, C127 cells and myeloma cells. In many cases, these cell types were selected because there was a great deal of preexisting literature on the cell type or the cell was simply being carried in the laboratory at the time the effort was made to express a peptide product. Frequently, factors which affect the downstream (e.g., beyond the T-75 flask) side of manufacturing scale-up were not considered before selecting the cell line as the host for the expression system.

Aspects of the present invention take advantage of the biochemical and cellular capacities of mammalian cells as well as of recently available bioreactor technology. Growing cells according to the present invention in a bioreactor allows for large scale production and secretion of complex, fully biologically-active polypeptides into the growth media. In particular embodiments, by designing a defined media with low contents of complex proteins and using a scheme of timed-stimulation of the secretion into the media for increased titer, the purification strategy can be greatly simplified, thus lowering production cost.

4.9.4.1 Anchorage-Dependent and Non-Anchorage-Dependent Cultures

Animal and human cells can be propagated in vitro in two modes: as non-anchorage dependent cells growing freely in suspension throughout the bulk of the culture; or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. Large scale suspension culture based on microbial (bacterial and yeast) fermentation technology has clear advantages for the manufacturing of mammalian cell products. The processes are relatively straightforward to operate and scale up. Homogeneous conditions can be provided in the reactor which allows for precise monitoring and control of temperature, dissolved oxygen, and pH, and ensure that representative samples of the culture can be taken.

However, suspension cultured cells cannot always be used in the production of biologicals. Suspension cultures are still considered to have tumorigenic potential and thus their use as substrates for production put limits on the use of the resulting products in human and veterinary applications (Petricciani, 1985; Larsson and Litwin, 1987). Viruses propagated in suspension cultures as opposed to anchorage-dependent cultures can sometimes cause rapid changes in viral markers, leading to reduced immunogenicity (Bahnemann, 1980). Finally, sometimes even recombinant cell lines can secrete considerably higher amounts of products when propagated as anchorage-dependent cultures as compared with the same cell line in suspension (Nilsson and Mosbach, 1987). For these reasons, different types of anchorage-dependent cells are used extensively in the production of different biological products.

The current invention includes cells which are anchorage-dependent of nature. Anchorage-dependent cells, when grown in suspension, will attach to each other and grow in clumps, eventually suffocating cells in the inner core of each clump as they reach a size that leaves the core cells unsustainable by the culture conditions. Therefore, an efficient means of large-scale culture of anchorage-dependent cells is also provided in order to effectively take advantage of the cells' capacity to secrete heterologous proteins.

4.9.4.2 Reactors and Processes for Suspension

Large scale suspension culture of mammalian cultures in stirred tanks is contemplated. The instrumentation and controls for bioreactors have been adapted, along with the design of the fermentors, from related microbial applications. However, acknowledging the increased demand for contamination control in the slower growing mammalian cultures, improved aseptic designs have been implemented, improving dependability of these reactors. Instrumentation and controls include agitation, temperature, dissolved oxygen, and pH controls. More advanced probes and autoanalyzers for on-line and off-line measurements of turbidity (a function of particles present), capacitance (a function of viable cells present), glucose/lactate, carbonate/bicarbonate and carbon dioxide are also available. Maximum cell densities obtainable in suspension cultures are relatively low at about $2-4 \times 10^6$ cells/ml of medium (which is less than 1 mg dry cell weight per ml), well below the numbers achieved in microbial fermentation.

Two suspension culture reactor designs are most widely used in the industry due to their simplicity and robustness of operation—the stirred reactor and the airlift reactor. The stirred reactor design has successfully been used on a scale of 8000 liter capacity for the production of interferon (Phillips et al., 1985; Mizrahi, 1983). Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively readily, has good mass transfer of gasses and generates relatively low shear forces.

Most large-scale suspension cultures are operated as batch or fed-batch processes because they are the most straightforward to operate and scale up. However, continuous processes based on chemostat or perfusion principles are available.

A batch process is a closed system in which a typical growth profile is seen. A lag phase is followed by exponential, stationary and decline phases. In such a system, the environment is continuously changing as nutrients are depleted and metabolites accumulate. This makes analysis of factors influencing cell growth and productivity, and hence optimization of the process, a complex task. Productivity of a batch process may be increased by controlled feeding of key nutrients to prolong the growth cycle. Such a fed-batch process is still a closed system because cells, products and waste products are not removed.

In what is still a closed system, perfusion of fresh medium through the culture can be achieved by retaining the cells with a fine mesh spin filter and spinning to prevent clogging. Spin filter cultures can produce cell densities of approximately $5 \times 10^7$ cells/ml. A true open system and the most basic perfusion process is the chemostat in which there is an inflow of medium and an outflow of cells and products. Culture medium is fed to the reactor at a predetermined and constant rate which maintains the dilution rate of the culture at a value less than the maximum specific growth rate of the cells (to prevent washout of the cell mass from the reactor). Culture fluid containing cells, cell products and byproducts is removed at the same rate. These perfused systems are not in commercial use for production from mammalian cell culture.

4.9.4.3 Non-Perfused Attachment Systems.

Traditionally, anchorage-dependent cell cultures are propagated on the bottom of small glass or plastic vessels. The restricted surface-to-volume ratio offered by classical and traditional techniques, suitable for the laboratory scale, has created a bottleneck in the production of cells and cell products on a large scale. To provide systems that offer large accessible surfaces for cell growth in small culture volume, a number of techniques have been proposed: the roller bottle system, the stack plates propagator, the spiral film bottles, the hollow fiber system, the packed bed, the plate exchanger system, and the membrane tubing reel. Since these systems are non-homogeneous in their nature, and are sometimes based on multiple processes, they can sometimes have limited potential for scale-up, difficulties in taking cell samples, limited potential for measuring and controlling the system and difficulty in maintaining homogeneous environmental conditions throughout the culture.

A commonly used process of these systems is the roller bottle. Being little more than a large, differently shaped T-flask, simplicity of the system makes it very dependable and, hence, attractive. Fully automated robots are available that can handle thousands of roller bottles per day, thus eliminating the risk of contamination and inconsistency associated with the otherwise required intense human handling. With frequent media changes, roller bottle cultures can achieve cell densities of close to $0.5 \times 10^6$ cells/cm$^2$ (corresponding to $10^9$ cells/bottle or $10^7$ cells/ml of culture media).

4.9.4.4 Cultures on Microcarriers van Wezel (1967) developed the concept of the microcarrier culturing systems. In this system, cells are propagated on the surface of small solid particles suspended in the growth medium by slow agitation. Cells attach to the microcarriers and grow gradually to confluency of the microcarrier surface. In fact, this large scale culture system upgrades the attachment dependent culture from a single disc process to a unit process in which both monolayer and suspension culture have been brought together. Thus, combining the necessary surface for the cells to grow with the advantages of the homogeneous suspension culture increases production.

The advantages of microcarrier cultures over most other anchorage-dependent, large-scale cultivation methods are several fold. First, microcarrier cultures offer a high surface-to-volume ratio (variable by changing the carrier concentration) which leads to high cell density yields and a potential for obtaining highly concentrated cell products. Cell yields are up to $1-2\times10^7$ cells/ml when cultures are propagated in a perfused reactor mode. Second, cells can be propagated in one unit process vessels instead of using many small low-productivity vessels (ie., flasks or dishes). This results in far better utilization and a considerable saving of culture medium. Moreover, propagation in a single reactor leads to reduction in need for facility space and in the number of handling steps required per cell, thus reducing labor cost and risk of contamination.

Third, the well-mixed and homogeneous microcarrier suspension culture makes it possible to monitor and control environmental conditions (e.g., pH, $pO_2$, and concentration of medium components), thus leading to more reproducible cell propagation and product recovery. Fourth, it is possible to take a representative sample for microscopic observation, chemical testing, or enumeration. Fifth, since microcarriers settle out of suspension easily, use of a fed-batch process or harvesting of cells can be done relatively easily. Sixth, the mode of the anchorage-dependent culture propagation on the microcarriers makes it possible to use this system for other cellular manipulations, such as cell transfer without the use of proteolytic enzymes, cocultivation of cells, transplantation into animals, and perfusion of the culture using decanters, columns, fluidized beds, or hollow fibers for microcarrier retainment. Seventh, microcarrier cultures are relatively easily scaled up using conventional equipment used for cultivation of microbial and animal cells in suspension.

4.9.4.5 Microencapsulation of Mammalian Cells

One method which has shown to be particularly useful for culturing mammalian cells is microencapsulation. The mammalian cells are retained inside a semipermeable hydrogel membrane. A porous membrane is formed around the cells permitting the exchange of nutrients, gases, and metabolic products with the bulk medium surrounding the capsule. Several methods have been developed that are gentle, rapid and non-toxic and where the resulting membrane is sufficiently porous and strong to sustain the growing cell mass throughout the term of the culture. These methods are all based on soluble alginate gelled by droplet contact with a calcium-containing solution. One method describes cells concentrated in an approximately 1% solution of sodium alginate which are forced through a small orifice, forming droplets, and breaking free into an approximately 1% calcium chloride solution. The droplets are then cast in a layer of polyamino acid that ionically bonds to the surface alginate. Finally the alginate is reliquefied by treating the droplet in a chelating agent to remove the calcium ions. Other methods use cells in a calcium solution to be dropped into a alginate solution, thus creating a hollow alginate sphere. A similar approach involves cells in a chitosan solution dropped into alginate, also creating hollow spheres.

Microencapsulated cells are easily propagated in stirred tank reactors and, with beads sizes in the range of 150–1500 mm in diameter, are easily retained in a perfused reactor using a fine-meshed screen. The ratio of capsule volume to total media volume can kept from as dense as 1:2 to 1:10. With intracapsular cell densities of up to $10^8$, the effective cell density in the culture is $1-5\times10^7$.

The advantages of microencapsulation over other processes include the protection from the deleterious effects of shear stresses which occur from sparging and agitation, the ability to easily retain beads for the purpose of using perfused systems, scale up is relatively straightforward and the ability to use the beads for implantation.

4.9.4.6 Perfused Attachment Systems

Perfusion refers to continuous flow at a steady rate, through or over a population of cells (of a physiological nutrient solution). It implies the retention of the cells within the culture unit as opposed to continuous-flow culture which washes the cells out with the withdrawn media (e.g., chemostat). The idea of perfusion has been known since the beginning of the century, and has been applied to keep small pieces of tissue viable for extended microscopic observation. The technique was initiated to mimic the cells milieu in vivo where cells are continuously supplied with blood, lymph, or other body fluids. Without perfusion, cells in culture go through alternating phases of being fed and starved, thus limiting full expression of their growth and metabolic potential. The current use of perfused culture is to grow cells at high densities (i.e., $0.1-5\times10^8$ cells/ml). In order to increase densities beyond $2-4\times10^6$ cells/ml (or $2\times10^5$ cells/cm$^2$), the medium has to be constantly replaced with a fresh supply in order to make up for nutritional deficiencies and to remove toxic products. Perfusion allows for a far better control of the culture environment (pH, $pO_2$, nutrient levels, etc.) and is a means of significantly increasing the utilization of the surface area within a culture for cell attachment.

Microcarrier and microencapsulated cultures are readily adapted to perfused reactors but, as noted above, these culture methods lack the capacity to meet the demand for cell densities above $10^8$ cells/ml. Such densities will provide for the advantage of high product titer in the medium (facilitating downstream processing), a smaller culture system (lowering facility needs), and a better medium utilization (yielding savings in serum and other expensive additives). Supporting cells at high density requires efficient perfusion techniques to prevent the development of non-homogeneity.

The cells of the present invention may, irrespective of the culture method chosen, be used in protein production and as cells for in vitro cellular assays and screens as part of drug development protocols.

4.10 Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the position being mutated. Typically, a primer of about 17 to about 75 nucleotides in length is preferred, with about 10 to about 25 or more residues on both sides of the position being altered, while primers of about 17 to about 25 nucleotides in length being more preferred, with about 5 to 10 residues on both sides of the position being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

A genetic selection scheme was devised by Kunkel et al. (1987) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990) and Upender et al. (1995) provide two examples of such protocols. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected gene using site-directed mutagenesis is provided as a means of producing potentially usefull species and is not meant to be limiting, as there are other ways in which sequence variants of genes may be obtained. For example, recombinant vectors encoding the desired gene may be treated with mutagenic agents, such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

4.11 ADA Proteins and Polypeptides

The present invention utilizes purified, and in preferred embodiments, substantially purified, ADA proteins and peptides. The term "purified ADA protein or peptide" as used herein, is intended to refer to a proteinaceous composition comprising any ADA polypeptide, isolatable from mammalian cells or recombinant host cells, wherein the ADA protein or polypeptide is purified to any degree relative to its naturally-obtainable state, i.e., relative to its purity within a cellular extract. A purified ADA protein or polypeptide therefore also refers to an ADA protein or peptide free from the environment in which it naturally occurs.

ADA proteins may be full length proteins, or less then full length proteins, such as individual domains or regions. Where less than full length ADA proteins are concerned the most preferred will be those containing predicted functional domains.

Generally, "purified" will refer to an ADA protein or polypeptide composition that has been subjected to fractionation to remove various non-ADA protein or polypeptide components, and which composition substantially retains its adenosine deaminase activity, as may be assessed by an adenosine deaminase assay (Winston et al., 1992).

Where the term "substantially purified" is used, this will refer to a composition in which the ADA protein or peptide forms the major component of the composition, such as constituting about 50% of the proteins in the composition or more. In preferred embodiments, a substantially purified protein will constitute more than 60%, 70%, 80%, 90%, 95%, 99% or even more of the proteins in the composition.

A polypeptide or protein that is "purified to homogeneity," as applied to the present invention, means that the polypeptide or protein has a level of purity where the polypeptide or protein is substantially free from other proteins and biological components. For example, a purified polypeptide or protein will often be sufficiently free of other protein components so that degradative sequencing may be performed successfully.

Various methods for quantifying the degree of purification of ADA proteins or polypeptides will be known to those of skill in the art in light of the present disclosure. These include, for example, determining the specific adenosine deaminase activity of a fraction, or assessing the number of polypeptides within a fraction by gel electrophoresis. Assessing the number of polypeptides within a fraction by SDS/PAGE analysis.

A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

To purify an ADA protein or polypeptide a natural or recombinant composition comprising at least some ADA proteins or polypeptides will be subjected to fractionation to remove various non-ADA components from the composition. Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps, isoelectric focusing, gel electrophoresis, and combinations of such and other techniques. As is generally known in the art, it is believed that the order of conducting the various purification steps may be changed, or that certain steps may be omitted, and still result in a suitable method for the preparation of a substantially purified protein or peptide.

Although preferred for use in certain embodiments, there is no general requirement that the ADA protein or peptide always be provided in their most purified state. Indeed, it is contemplated that less substantially purified ADA proteins or peptides, which are nonetheless enriched in ADA protein compositions, relative to the natural state, will have utility in certain embodiments. These include, for example, antibody generation where subsequent screening assays using purified ADA proteins are conducted.

Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system.

Methods exhibiting a lower degree of relative purification may have advantages in total recovery of protein product, or in maintaining the activity of an expressed protein. Inactive products also have utility in certain embodiments, such as, e.g., in antibody generation.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography.

4.12 Biological Functional Equivalents

As modifications and changes may be made in the structure of ADA genes and proteins of the present invention, and still obtain molecules having like or otherwise desirable characteristics, such biologically functional equivalents are also encompassed within the present invention.

For example, certain amino acids may be substituted for other amino acids in a protein structure without appreciable loss of interactive binding capacity with structures such as, for example, antigen-binding regions of antibodies, binding sites on substrate molecules or receptors, DNA binding sites, or such like. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. It is thus contemplated by the inventors that various changes may be made in the sequence of ADA proteins or polypeptides, or underlying DNA, without appreciable loss of their biological utility or activity.

In terms of functional equivalents, it is well understood by the skilled artisan that, inherent in the definition of a "biologically functional equivalent protein or peptide or gene", is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted.

In particular, where shorter length peptides are concerned, it is contemplated that fewer amino acid substitutions should be made within the given peptide. Longer domains may have an intermediate number of changes. The full length protein will have the most tolerance for a larger number of changes. Of course, a plurality of distinct proteins/peptides with different substitutions may easily be made and used in accordance with the invention.

It is also well understood that where certain residues are shown to be particularly important to the biological or structural properties of a protein or peptide, e.g., residues in binding regions or active sites, such residues may not generally be exchanged. This is an important consideration in the present invention, where changes in the ADA active site should be carefully considered and subsequently tested to ensure maintenance of biological function, where maintenance of biological function is desired. In this manner, functional equivalents are defined herein as those peptides which maintain a substantial amount of their native biological activity.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and antigenicity, ie. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein for use in such embodiments, as well as for other uses, such as in the design of probes and primers and the like.

In addition to the ADA peptidyl compounds described herein, the inventors also contemplate that other sterically similar compounds may be formulated to mimic the key portions of the peptide structure or to interact specifically with, for example, substrates or receptor compounds. Such compounds, which may be termed peptidomimetics, may be used in the same manner as the peptides of the invention and hence are also functional equivalents.

Certain mimetics that mimic elements of protein secondary structure are described in Johnson et al. (1993). The underlying rationale behind the use of peptide mimetics is that the peptide backbone of proteins exists chiefly to orientate amino acid side chains in such a way as to facilitate molecular interactions, such as those of antibody and antigen. A peptide mimetic is thus designed to permit molecular interactions similar to the natural molecule.

4.13 Gene Therapy

The general approach to the aspects of the present invention concerning asthma therapeutics is to provide an animal with an ADA protein, thereby permitting the proper regulatory activity of the proteins to take effect. While in preferred embodiments the protein may be delivered directly, other embodiments involve providing a nucleic acid encoding a ADA protein to the animal. Such approaches are herein encompassed within the term "gene therapy". Following this provision, the polypeptide is synthesized by the transcriptional and translational machinery of the cell, as well as any that may be provided by the expression construct.

In certain embodiments of the invention, the nucleic acid encoding the gene may be stably integrated into the genome of the cell. In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

4.13.1 DNA Delivery Using Viral Vectors

The ability of certain viruses to infect cells or enter cells via receptor-mediated endocytosis, and to integrate into host cell genome and express viral genes stably and efficiently have made them attractive candidates for the transfer of foreign genes into mammalian cells. Preferred gene therapy vectors of the present invention will generally be viral vectors.

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

4.13.1.1 Adenoviral Vectors

A particular method for delivery of the expression constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue-specific transforming construct that has been cloned therein.

The expression vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (E1A and E1B; Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1991; Rich et al, 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993). Recombinant adenovirus and adeno-associated virus (see below) can both infect and transduce non-dividing human primary cells.

4.13.1.2 AAV Vectors

Adeno-associated virus (AAV) is an attractive vector system for use in the cell transduction of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin, et al., 1984; Laughlin, et al., 1986; Lebkowski, et al., 1988; McLaughlin, et al., 1988). Details concerning the generation and use of rAAV vectors are described in U.S. Pat. Nos. 5,139,941 and 4,797,368, each incorporated herein by reference.

Studies demonstrating the use of AAV in gene delivery include LaFace et al. (1988); Zhou et al (1993); Flotte et al. (1993); and Walsh et al. (1994). Recombinant AAV vectors have been used successfully for in vitro and in vivo transduction of marker genes (Kaplitt, et al., 1994; Lebkowski, et al., 1988; Samulski, et al., 1989; Yoder, et al., 1994; Zhou, et al., 1994; Hermonat and Muzyczka, 1984; Tratschin, et al., 1985; McLaughlin, et al., 1988) and genes involved in human diseases (Flotte, et al., 1992; Luo, et al., 1994; Ohi, et al., 1990; Walsh, et al., 1994; Wei, et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski, et al., 1989; McLaughlin, et al., 1988; Kotin, et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

4.13.1.3 Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines.

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Gene delivery using second generation retroviral vectors has been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO)

receptor. This was achieved by inserting a portion of the EPO sequence into an envelope protein to create a chimeric protein with a new binding specificity.

4.13.1.4 Other Viral Vectors

Other viral vectors may be employed as expression constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In certain further embodiments, the gene therapy vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and can be grown to high titers. Thus, delivery is less of a problem, both in terms of volumes needed to attain sufficient MOI and in a lessened need for repeat dosings.

4.13.1.5 Modified Viruses

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

4.13.2 Other Methods of DNA Delivery

In various embodiments of the invention, DNA is delivered to an animal as an expression construct. In order to effect expression of a gene construct, the expression construct must be delivered into a cell. As described herein, the preferred mechanism for DNA delivery is via viral infection, where the expression construct is encapsidated in an infectious viral particle. However, several non-viral methods for the transfer of expression constructs into cells also are contemplated by the present invention. In one embodiment of the present invention, the expression construct may consist only of naked recombinant DNA or plasmids. Transfer of the construct may be performed by any of the methods mentioned which physically or chemically permeabilize the cell membrane. Some of these techniques may be successfully adapted for in vivo or ex vivo use, as discussed below.

4.13.2.1 Liposome-Mediated Transfection

In a further embodiment of the invention, the expression construct may be entrapped in a liposome. Liposomes are vesicular structures characterized by a phospholipid bilayer membrane and an inner aqueous medium and are discussed in section 4.5.2. Also contemplated is an expression construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

4.13.2.2 Electroporation

In certain embodiments of the present invention, the expression construct is introduced into the cell via electroporation. Electroporation involves the exposure of a suspension of cells and DNA to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

4.13.2.3 Calcium Phosphate Precipitation or DEAE-Dextran Treatment

In other embodiments of the present invention, the expression construct is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and erythroleukemia cells (Gopal, 1985).

4.13.2.4 Particle Bombardment

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

4.13.2.5 Direct Microinjection or Sonication Loading

Further embodiments of the present invention include the introduction of the expression construct by direct microinjection or sonication loading. Direct microinjection has been used to introduce nucleic acid constructs into Xenopus oocytes (Harland and Weintraub, 1985), and LTK⁻ fibroblasts have been transfected with the thymidine kinase gene by sonication loading (Fechheimer et al., 1987).

4.13.2.6 Adenoviral Assisted Transfection

In certain embodiments of the present invention, the expression construct is introduced into the cell using adenovirus assisted transfection. Increased transfection efficiencies have been reported in cell systems using adenovirus coupled systems (Kelleher and Vos, 1994; Cotten et al., 1992; Curiel, 1994).

4.13.2.7 Receptor Mediated Transfection

Still further expression constructs that may be employed to deliver the tissue-specific promoter and transforming construct to the target cells are receptor-mediated delivery vehicles. These take advantage of the selective uptake of macromolecules by receptor-mediated endocytosis that will be occurring in the target cells. In view of the cell type-specific distribution of various receptors, this delivery method adds another degree of specificity to the present invention. Specific delivery in the context of another mammalian cell type is described by Wu and Wu (1993; incorporated herein by reference).

Certain receptor-mediated gene targeting vehicles comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. In the context of the present invention, the ligand will be chosen to correspond to a receptor specifically expressed on the neuroendocrine target cell population.

In other embodiments, the DNA delivery vehicle component of a cell-specific gene targeting vehicle may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the targeted delivery vehicles may be a liposome itself, which will preferably comprise one or more lipids or glycoproteins that direct cell-specific binding. For example, Nicolau et al. (1987) employed lactosyl-ceramide, a galactose-terminal asialganglioside, incorporated into liposomes and observed an increase in the uptake of the insulin gene by hepatocytes. It is contemplated that the tissue-specific transforming constructs of the present invention can be specifically delivered into the target cells in a similar manner.

4.13.3 Marker Genes

In certain aspects of the present invention, specific cells are tagged with specific genetic markers to provide information about the fate of the tagged cells. Therefore, the present invention also provides recombinant candidate screening and selection methods which are based upon whole cell assays and which, preferably, employ a reporter gene that confers on its recombinant hosts a readily detectable phenotype that emerges only under conditions where a general DNA promoter positioned upstream of the reporter gene is functional. Generally, reporter genes encode a polypeptide (marker protein) not otherwise produced by the host cell which is detectable by analysis of the cell culture, e.g., by fluorometric, radioisotopic or spectrophotometric analysis of the cell culture.

In other aspects of the present invention, a genetic marker is provided which is detectable by standard genetic analysis techniques, such as DNA amplification by PCR™ or hybridization using fluorometric, radioisotopic or spectrophotometric probes.

4.13.3.1 Screening

Exemplary enzymes include esterases, phosphatases, proteases (tissue plasminogen activator or urokinase) and other enzymes capable of being detected by their activity, as will be known to those skilled in the art. Contemplated for use in the present invention is green fluorescent protein (GFP) as a marker for transgene expression (Chalfie et al., 1994). The use of GFP does not need exogenously added substrates, only irradiation by near UV or blue light, and thus has significant potential for use in monitoring gene expression in living cells.

Other particular examples are the enzyme chloramphenicol acetyltransferase (CAT) which may be employed with a radiolabelled substrate, firefly and bacterial luciferase, and the bacterial enzymes β-galactosidase and β-glucuronidase. Other marker genes within this class are well known to those of skill in the art, and are suitable for use in the present invention.

4.13.3.2 Selection

Another class of reporter genes which confer detectable characteristics on a host cell are those which encode polypeptides, generally enzymes, which render their transformants resistant against toxins. Examples of this class of reporter genes are the neo gene (Colberre-Garapin et al., 1981) which protects host cells against toxic levels of the antibiotic G418, the gene conferring streptomycin resistance (U. S. Pat. No. 4,430,434), the gene conferring hygromycin B resistance (Santerre et al., 1984; U.S. Pat. Nos. 4,727,028, 4,960,704 and 4,559,302), a gene encoding dihydrofolate reductase, which confers resistance to methotrexate (Alt et al., 1978), the enzyme HPRT, along with many others well known in the art (Kaufman, 1990).

4.14 Screening for Treatment of Asthma and Adenosine Signaling

The inventors contemplate that the animals of the present invention may be used in the screening of compounds for their ability to alleviate asthma and/or effect adenosine signaling in other systems, including cardiac and cardiovascular, neurologic, immunologic, renal, gastrointestinal, vascular, bone and reproductive systems.

The ability of the present inventors to create transgenic animals which mimic these diseases provides an ideal setting in which to test various compounds for therapeutic activity. Particularly preferred compounds will be those useful in lowering systemic adenosine levels and preventing or reversing asthma, however, the animals are useful as a model system for testing existing and new therapies of asthma that do not target adenosine concentrations. In the screening assays of the present invention, the candidate substance may first be screened for basic biochemical activity—e.g., binding to a target molecule—and then tested for its ability to alleviate asthma or adenosine signaling, at the whole animal level.

In certain embodiments, the present invention is directed to a method for determining the ability of a candidate substance to alleviate asthma, generally including the steps of:

(a) providing an animal having asthmatic symptoms;
(b) administering a candidate therapeutic compound to said animal; and
(c) monitoring said animal for a lessening of asthmatic symptoms as compared to a similar animal not treated with said candidate inhibitor.

In other embodiments, the present invention is directed to a method for determining the ability of a candidate substance to effect adenosine signaling or systemic adenosine levels, generally including the steps of:

(a) providing an animal having elevated systemic adenosine levels;
(b) administering a candidate therapeutic compound to said animal; and
(c) monitoring said animal for a lowering of systemic adenosine levels as compared to a similar animal not treated with said candidate inhibitor.

Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply.

To identify a candidate substance as being capable of alleviates symptoms associated with asthma in the assay above, one would measure or determine various characteristics of the animal, for example, inflammation of the lungs particularly the level of eosinophils, occlusion of the airways, or other pulmonary disorders and the like in the absence of the added candidate substance. In a preferred embodiments, the number of eosinophils in the lungs are compared between animals receiving the therapeutic compound and those that not receiving the compound. This may be done by bronchoalveolar lavage followed by differential staining of the cells and manually counting the number of eosinophils or by automated technologies such as FACS. One would then administer the candidate substance to the animal and determine the response in the presence of the candidate substance. A candidate substance which decreases the asthma associated characteristic in comparison to its absence, is indicative of a candidate substance with therapeutic capability. In the screening assays of the present invention, the compound is administered to the animals, over period of time and in various dosages, and pulmonary condition is measured.

To identify a candidate substance as being capable of lowering systemic adenosine levels or effecting adenosine signaling in the assay above, one would measure or determine various characteristics of the animal, for example, systemic levels of adenosine or abnormalities in physiologic systems, including cardiac and cardiovascular, neurologic, immunologic, renal, gastrointestinal, vascular, bone and reproductive systems and the like in the absence of the added candidate substance. One would then administer the candidate substance to the animal and determine the response in the presence of the candidate substance. A candidate substance which decreases systemic adenosine levels or effects the abnormal physiologic characteristic in comparison to its absence, is indicative of a candidate substance with therapeutic capability. In the screening assays of the present invention, the compound is administered to the animals, over period of time and in various dosages, and physiologic conditions associated with elevated adenosine levels are measured.

As used herein the term "candidate substance" refers to any molecule that may potentially alleviate the symptoms of asthma. The candidate substance may be a protein or fragment thereof, a small molecule inhibitor, or even a nucleic acid molecule. It may prove to be the case that the most useful pharmacological compounds will be compounds that are structurally related to other known modulators of adenosine levels in an animal, such as ADA. Such an endeavor often is know as "rational drug design," and includes not only comparisons with know enzymes, but predictions relating to the structure of target molecules.

The goal of rational drug design is to produce structural analogs of biologically active polypeptides or target compounds. By creating such analogs, it is possible to fashion drugs which are more active or stable than the natural molecules, which have different susceptibility to alteration or which may affect the function of various other molecules. In one approach, one would generate a three-dimensional structure for a molecule like ADA, or a fragment thereof. This could be accomplished by x-ray crystallography, computer modeling or by a combination of both approaches.

It also is possible to use antibodies to ascertain the structure of a target compound. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known adenosine binding or converting compounds.

"Effective amounts" in certain circumstances are those amounts effective to reproducibly decrease asthma in the animal in comparison to untreated animals. Compounds that achieve significant appropriate changes in activity will be used.

Significant changes in symptoms of asthma, e.g., as measured airway function such as respiratory resistance, are represented by a decrease in resistance of at least about 20% to about 50%, with higher values of course being possible.

It will, of course, be understood that all the screening methods of the present invention are useful in themselves notwithstanding the fact that effective candidates may not be found. The invention provides methods for screening for such candidates, not solely methods of finding them.

4.15 Polyethylene Glycol Modified Adenosine Deaminase

In a preferred embodiment, ADA polypeptides are conjugated to polyethylene glycol (PEG). As used herein, PEGADA refers to ADA polypeptides or functional equivalents thereof conjugated to PEG. PEG is made up of chains of repeating subunits that may be of variable lengths. Because of the variable nature of PEG, it may be produced or is commercially available at different molecular weights. Commercially available PEG is generally identified by the average molecular weight of the PEG. Molecular weights of PEG commercially available include, but are not limited to, 200, 300, 400, 550, 600, 900, 1000, 1,450, 1,500, 2,000, 3,350, 3,400, 4.600, 8,000, and 10,000. PEG compounds also are available that are created by joining internally two moles of polyethylene glycol (molecular weight 7,000–9,000) to yield a compound of molecular weight of 15,000 to 20,000.

Also available commercially are different grades of PEG based on the percentage of impurities and PEG derivatives including methoxypolyethylene glycol and derivatives, polyoxyethylene (functionalized derivatives), and ether derivatives (polyethylene ethers; surfactants).

Of course, because the PEGADA of the present invention is for in vivo purposes, one would want to be sure that the PEG is of appropriate grade and purity to be administered to an animal. PEGADA may be obtained from (ENZON, Inc.; Piscataway, N.J.).

4.16 Pegada Treatments

In important embodiments of the present invention, animals with asthma-like lung disorders are treated with compounds comprising polypeptides capable of catabolizing adenosine. In preferred embodiments, the compounds are PEGADA compounds.

The inventors contemplate that PEGADA treatments may be chronic or acute. In preferred chromic treatments a constant level of PEGADA is maintained in the mouse at concentrations of 150 to 300 U/Kg. In preferred acute treatments, a single dose of PEGADA (300 U/Kg) is given.

For chronic treatment of the mice of the present invention, litters are given an intramuscular injection of PEGADA at four days of postnatal file. The initial dose of PEGADA given is approximately 300 U/Kg body weight, where U (unit) is defined as 1 μmole adenosine converted to inosine per minute. this dose is within an order of magnitude of that given to treat ADA deficient humans. Mice were treated every four days with a dose of 150 to 300 U/Kg. This treatment protocol is sufficient to rescue ADA deficient mice that, without treatment, die by three weeks of age.

For acute treatment of the mice of the present invention, mice are injected intramuscularly once on postnatal day 18 with 300 U/kg PEGADA.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Adenosine Deaminase Deficient Mice Generated Using a Two Stage Genetic Engineering Strategy Exhibit a Combined Immunodeficiency The perinatal death of ADA deficient fetuses precluded the inventors' ability to assess the consequences of ADA deficiency in postnatal animals. In this example, the inventors describe the use of a transgenic strategy to rescue ADA deficient fetuses from perinatal lethality by restoring Ada expression to trophoblast cells. This procedure led to the development of postnatal animals that were completely ADA deficient. These ADA deficient mice retain many features seen in ADA deficient humans, in particular a severe lymphopenia and combined immunodeficiency. In addition, ADA deficient mice develop severe pulmonary insufficiency, and bone and kidney abnormalities were detected. The ability to examine metabolic disturbances in a variety of tissues of ADA deficient mice revealed a widespread accumulation of adenosine, while 2'-deoxyadenosine accumulated in a predominantly lymphoid-specific manner. AdoHcy hydrolase inhibition and dATP accumulation were greatest in the thymus and spleen of ADA deficient mice. These genetically engineered ADA deficient mice have thus provided novel in vivo information into the metabolic basis for the immune phenotype associated with ADA deficiency.

5.1.1 Materials and Methods 5.1.1.1 Generation and Characterization of Mice

An ADA minigene (Blackburn et al., 1995) was fused to a 2.0 kb BamHI to EagI genomic fragment in the 5' flanking region of the murine Ada gene that contained a 770 bp trophoblast regulatory element (Shi et al., 1997). This construct was purified and used to generate transgenic mice (Blackburn et al., 1995). Genomic DNA was isolated from tails at postnatal day 15 to 22, digested with BamHI, and hybridized with an internal 3.5 kb BamHI fragment of the ADA minigene as a probe (Wakamiya et al., 1995; Blackburn et al., 1995). ADA transcript levels in placentas and fetuses were monitored by RNase protection, ADA enzymatic activity and zymogram analysis was conducted as described previously (Blackburn et al., 1995; Blackburn et al., 1996). ADA deficient mice were generated and genotyped as described previously (Blackburn et al., 1998).

Control mice were either wild type mice or mice heterozygous for the null Ada allele. There was no phenotype seen in heterozygous animals (Blackburn et al., 1998). All mice were housed in cages equipped with microisolator lids and maintained under strict containment protocols. Infection was monitored by examining lung sections stained with giemsa silver stain and periodic acid Schiff (PAS). No evidence of bacterial, parasitic or fungal infection was found. In addition, serologies were negative for 12 of the most common murine viruses.

5.1.1.2 Histological Analysis

Tissues of interest were dissected from control and ADA deficient mice on postnatal day 15. Tissues were rinsed in ice-cold PBS and then fixed overnight in 4% paraformaldehyde in PBS at 4° C. Tissues were then dehydrated, cleared and embedded in paraffin according to established procedures. Sections 7 $\mu$M in thickness were collected on positively charged microscope slides and stained with hematoxylin and eosin using a Rapid Chrome staining kit (Shandon; Pittsburgh, Pa.). Photographs of sections were generated using an Olympus BX60 microscope with bright field illumination. Analysis of bone using alyzerin red and azure blue was conducted according to stablished protocols.

5.1.1.3 Immunology

Determination of lymphoid cell counts in thymuses and spleens were conducted as previously described (Blackburn et al., 1996). For examination of peripheral lymphocytes, 200 $\mu$l blood was collected from the tail vein of mice directly into EDTA coated microfuge tubes. Complete blood counts were determined using an H1-analyzer (Technicon Instruments Corporation; Houston, Tex.). For determination of serum immunoglobulins, whole blood was collected by cardiac puncture, allowed to set on ice for 15 min and then centrifuged for 10 min at 2000×g at 4° C. Serum was removed and stored at −70° C. until analyzed. Serum immunoglobulin levels were determined using a single radioimmuno diffusion assay (Charles River Laboratories; Wilmington, Mass.). Direct two color analysis with antibodies against the cell surface antigens CD3, CD4, CD8, TCR $\alpha/\beta$, IgM and B220 was performed according to established methods (Blackburn et al., 1996).

5.1.1.4 Nucleoside and Nucleotide Analysis and Determination of S-Adenosylhomocysteine Hydrolase Enzymatic Activity Tissues were quickly removed from control or ADA deficient mice, frozen in liquid nitrogen, and nucleosides and nucleotides were extracted and analyzed according to established procedures (Blackburn et al., 1995; Knudsen et al., 1992; Gao et al., 1994). AdoHcy hydrolase enzymatic activity was determined in freshly prepared tissue extracts according to established procedures (Blackburn et al., 1996).

5.1.2 Results 5.1.2.1 Generation of ADA Deficient Mice Using a Two Stage Genetic Engineering Strategy Previous studies suggest that Ada expression in trophoblast cells of the placenta is critical for fetal development in the mouse (Knudsen et al., 1991; Blackburn et al., 1995). Thus, to generate completely ADA deficient postnatal mice, an ADA minigene that targeted expression specifically to the trophoblast lineage was introduced onto the ADA deficient background. The murine ADA minigene consisted of the murine ADA cDNA, endogenous polyadenylation sequences, including endogenous intron 11 and about 2 kb of 3' flank from the murine ADA gene. Driving expression of the minigene is the endogenous ADA promoter (containing a 36 bp deletion in the 5' untranslated region to help distinguish the transgene from the endogenous ADA gene) and a 770 bp trophoblast regulatory element (TE). Endogenous Ada and ADA minigene transcript levels in fetuses and placentas of normal mice and transgenic mice were compared. RNase protection assays were carried out using total cellular RNA from fetuses (F) and placentas (P) on 13.5 days post coitum. Transgenic (Tg) placentas showed expression from the ADA minigene locus to be ~10% that of the native Ada gene.

Mice carrying the trophoblast-specific ADA minigene (Tg) were then intercrossed with mice heterozygous for the null Ada allele (ml/+). Subsequent intercrosses yielded litters that contained mice harboring the ADA minigene (Tg) that were also homozygous for the null Ada allele (ml/ml). Southern blot analysis was used to follow the Ada locus and ADA minigene locus from an intercrossing between animals hemizygous for the ADA minigene locus and heterozygous for the null Ada allele. Hybridization fragments of 4.7 kb (Wt or +), 6.3 kb (Mt or ml) and 3.5 kb (Tg) in size were used to confirm genotypes including wild-type mice with the ADA minigene locus (Tg-+/+), mice heterozygous for the null Ada allele with (Tg-ml/+) and without (ml/+) the ADA minigene locus, and mice homozygous for the null Ada allele and containing the ADA minigene locus (Tg, ml/ml).

Given that the regulatory elements used targeted Ada expression only to trophoblasts, once born, and with the loss of the placenta, Tg-ml/ml mice should lack ADA enzymatic activity. To monitor Ada expression in rescued mice, control and Tg-ml/ml mice were sacrificed on postnatal day 15 and ADA enzymatic activity determined in various tissue extracts. ADA enzymatic activity was measured in crude extracts of tissues from Tg-ml/+, n=3 and Tg-ml/ml, n=3 mice on postnatal day 17. Mean specific activities for Tg-ml/+ (reported as nmoles substrate converted per min per mg protein) were determined for the following tissues; tongue (1430), forestomach (730), hindstomach (12), small intestine (130), large intestine (15), thymus (90), spleen (10), liver (5), kidney (5), lung (5), brain (5), heart (5), and blood. No activity was detected in tissues from Tg-ml/ml mice at a minimal detection limit of 2 nmoles/min/mg. ADA zymogram analysis was performed on 1 $\mu$g of protein from each tissue except for blood which contained 10 to 20 $\mu$g. Purine nucleoside phosphorylase (PNP) zymogram analysis was used as a positive control and 2 $\mu$g of protein from each tissue was used except for blood which contained 10 to 20 $\mu$g. Therefore, expression in trophoblast cells alone was sufficient to rescue ADA deficient fetuses from perinatal lethality, and provide postnatal mice that were ADA deficient.

5.1.2.2 ADA Deficient Mice Develop Severe Lymphopenia and Combined Immunodeficiency ADA deficient humans fail to thrive and die within the first few months of life if not properly diagnosed and treated (Hershfield and Mitchell, 1995). ADA deficient mice generated by trophoblast rescue also fail to thrive and die by approximately 3 weeks of age. Nevertheless, these mice provided us the opportunity to directly assess the effect of ADA deficiency on the thymus and spleen, critical immune organs that are not accessible for analysis in ADA deficient humans. The status of the immune system in ADA deficient mice was assessed between postnatal days 15 and 17 prior to a severe decline in health to minimize the influence of physiologic stress on the immune phenotype. Gross examination of the thymus and spleen in ADA deficient mice revealed a substantial decrease in organ size that corresponded with a greater than 50% reduction in organ-to-body weights. Histological analysis of hematoxylin and eosin stained sections revealed a decrease in the size of the thymus and spleen of ADA deficient mice as compared to control mice. Examination at a higher magnification of ADA deficient mice showed that there was a decrease in cortical-medullary demarcation in ADA deficient thymuses, and Hassel's corpuscles were not found. Examination of spleens from ADA deficient mice revealed a decrease in the number of red blood cells found in the red pulp, and few megakayocytes were observed. Consistent with the decrease in organ size, lymphoid cell counts were substantially reduced in the ADA deficient thymus (8-fold) and spleen (3-fold) (FIG. 1A). Lymphopenia was also seen in the peripheral circulation where ADA deficient mice contained ⅓ the number of peripheral lymphoid cells seen in control mice (FIG. 1B). Serum immunoglobulin levels were measured to determine if the humoral branch of the immune system was affected by ADA deficiency. Total serum immunoglobulin levels were reduced 3-fold in ADA deficient mice (FIG. 1C), suggesting an immunodeficiency. Because mice were analyzed prior to weaning, it is likely that maternal IgG accounts for most and possibly all of the serum immunoglobulins (Malanchere et al., 1997). Therefore, the ability of ADA deficient mice to produce immunoglobulins is likely to be severely reduced. These data demonstrate that ADA deficient mice exhibit a combined T and B cell lymphopenia and immunodeficiency.

It has not been possible to assess the distribution of lymphocyte populations in the immune organs of ADA deficient humans. To determine whether genetic ADA deficiency leads to alterations in thymic cell populations, flow cytometry was performed on cellular populations from the thymuses of ADA deficient mice. There were substantial differences in the distribution of thymocytes bearing cell surface antigens specific for different stages of T lymphocyte development. In ADA deficient thymuses, there was a significant increase in the percentage of $CD4^-CD8^-$ double-negative immature thymocytes, whereas there was a decrease in the percentage of $CD4^+CD8^+$ double-positive thymocytes and $CD4^+$ and $CD8^+$ single-positive thymocytes (FIG. 2A). These data suggest that developing thymocytes at the transition from the double-negative to double-positive stage are sensitive to the consequences of ADA deficiency.

Lymphoid cells from ADA deficient spleens were examined to determine whether there were alterations in mature lymphoid populations. There was a substantial decrease in the percentage of mature $CD4^+$ and $CD8^+$ T lymphocytes in ADA deficient spleens (FIG. 2B). An increase in granulocytes and macrophages, eosinophilia and anemia were also noted in ADA deficient mice (data not shown), whereas, there was not a significant difference in the distribution of splenic cells harboring the B lymphocyte markers IgM or B220 (FIG. 2B). The decrease in the percentages of $CD4^+$ and $CD8^+$ T lymphocytes, together with the general T and B cell lymphopenia and hypogammaglobulinemia, suggest that ADA deficient mice exhibit a combined immunodeficiency.

5.1.2.3 ADA Deficient Mice Exhibit Severe Disturbances in the Levels of the ADA Substrates Adenosine and 2'-Deoxyadenosine Metabolic disturbances associated with ADA deficiency in humans have only been monitored in fluid and cellular components that are accessible, such as plasma, serum and urine (Hershfield and Mitchell, 1995; Morgan et al., 1987; Donofrio et al., 1978). The levels of adenosine and 2'-deoxyadenosine are readily detected in these samples; however, little to nothing is known with regard to the metabolic disturbances in tissues of ADA deficient individuals. Monitoring metabolic disturbances in the tissues of ADA deficient mice, in particular immunologic tissues, would provide important information into the mechanism of the immunodeficiency associated with ADA deficiency. To monitor metabolic disturbances in tissues of ADA deficient mice, animals were sacrificed on postnatal day 15 and various tissues were rapidly collected and processed for nucleoside analysis. Consistent with observations made in ADA deficient humans, there was a marked accumulation of adenosine (FIG. 3A) and 2'-deoxyadenosine (FIG. 3C) in the serum of ADA deficient mice. Upon examination of various tissues, adenosine levels were found to be elevated in all tissues examined with the greatest accumulation occurring in the liver, kidney and lung (FIG. 3B). 2'-Deoxyadenosine was also detected in all ADA deficient tissues examined with the greatest accumulation occurring in the lymphoid organs (FIG. 3D). 2'-Deoxyadenosine was elevated more than 500-fold in the thymus to levels greater than 200 times that found in the serum of ADA deficient mice (FIG. 3C). These studies demonstrate that there are severe metabolic disturbances in tissues of ADA deficient mice.

5.1.2.4 ADA Deficient Mice Demonstrate Elevated Levels of dATP and Inhibition of S-Adenosylhomocysteine Hydrolase The inhibition of AdoHcy hydrolase and the accumulation of dATP are common features monitored in red blood cells of ADA deficient individuals (Hershfield and Mitchell, 1995; Hershfield et al., 1979; Kaminska and Fox, 1980). Disturbances in these pathways have been noted in mice treated with the ADA inhibitor 2'-deoxycoformycin (Ratech et al., 1981); however, nothing is known with regard to the involvement of these toxic pathways in tissues of ADA deficient individuals. To determine if these metabolic endpoints were effected in tissues of ADA deficient mice, AdoHcy hydrolase enzymatic activity and dATP levels were monitored in various tissues (FIG. 4). In red blood cells it was found that, as in humans, AdoHcy hydrolase activity was inhibited (FIG. 4A) and dATP accumulated to very high levels (FIG. 4C). AdoHcy hydrolase enzymatic activity was inhibited in all tissues examined with the greatest degree of inhibition seen in the thymus (85%) and spleen (90%) (FIG. 4B). dATP levels were increased in all tissues examined (FIG. 4D). The greatest accumulation of dATP was in red blood cells (FIG. 4C); however, amongst other tissues examined, the greatest accumulation (50-fold) was seen in the thymus (FIG. 4D). Therefore, ADA deficient mice retain metabolic disturbances associated with ADA deficiency in humans. Moreover, of numerous tissues examined, the most severe metabolic disturbances occur in lymphoid tissues.

5.1.2.5 Lung, Bone and Kidney Abnormalities are Observed in ADA Deficient Mice

In addition to a combined immunodeficiency, ADA deficient humans exhibit pathologic findings including, liver, kidney, adrenal, and bone abnormalities (Bollinger et al., 1996; Ratech et al., 1985, Cederbaum et al., 1976). To determine if there were pathological alterations in nonlymphoid tissues of ADA deficient mice, tissues were harvested on postnatal day 15 and examined histologically. Severe histological observations were found in the lung of ADA deficient mice. There was a large increase in the number of inflammatory cells in the lung, together with massive thickening and shedding of airway epithelium and occlusions of the airways with cellular debris and mucus. Consistent with these histological observations, mice began to show signs of tachypnea as early as postnatal day 12, and this labored breathing became increasingly severe up to the death of the animals between days 18 and 22. This severe pulmonary insufficiency is speculated to lead to the death of ADA deficient mice, and the basis for the lung inflammation is under investigation. Bone abnormalities of the rib cage were also noted in ADA deficient mice. There was an enlargement of the costochondral junctions, as well as a severe rib curvature. Abnormal pathogenesis was also seen in the kidneys of ADA deficient mice. Kidneys appeared normal in size but were dark red in comparison to control kidneys that were pink. Histological examination revealed a normal organization in the ADA deficient kidney; however, there was a substantial increase in red blood cells found in glomeruli and convoluted tubules of ADA deficient kidneys. These results suggest that ADA deficient mice exhibit many of the nonlymphoid phenotypes observed in ADA deficient humans.

5.1.3 Discussion

This example discusses a transgenic approach to genetically restore ADA specifically to trophoblasts of otherwise ADA deficient fetuses. Expression of Ada in trophoblasts was sufficient to rescue ADA deficient fetuses from perinatal lethality, and with loss of the placenta at birth, rescued mice were found to be completely ADA deficient. These ADA deficient mice provided for the first time the opportunity to examine the phenotypic and tissue-specific metabolic disturbances associated with ADA deficiency in postnatal mice.

Amongst the most striking observations made in ADA deficient mice was a profound T and B cell lymphopenia. Furthermore, levels of serum immunoglobulins were greatly diminished suggesting these animals suffer from a combined T and B cell deficiency. These features are consistent with the immune phenotype observed in ADA deficient humans (Hershfield and Mitchell, 1995). The ability to analyze tissues from ADA deficient mice, that are not easily attainable in ADA deficient humans, allowed the inventors to make additional observations regarding the immune phenotype associated with ADA deficiency. In the thymus of ADA deficient mice, the percentage of $CD4^-CD8^-$ double-negative immature thymocytes increased while the percentage of $CD4^+CD8^+$ double-positive thymocytes and $CD4^+$ and $CD8^+$ single-positive thymocytes decreased accordingly (FIG. 2A). This suggests that developing thymocytes are sensitive to the metabolic consequences of ADA deficiency at the transition from the double-negative to double-positive stage. This observation is consistent with those seen in mice treated with the ADA inhibitor 2'-deoxycoformycin (Doherty et al., 1991; Ratter et al., 1996). However, the severe reduction in lymphoid cell number in the thymus suggests that there is a general lymphotoxicity associated with ADA deficiency, possibly a block at a prethymic stage of T cell development.

The ability to analyze individual tissues also provided novel information into potential metabolic mechanisms that lead to the combined immunodeficiency associated with ADA deficiency. There was a widespread accumulation of adenosine in all tissues examined in ADA deficient mice, whereas 2'-deoxyadenosine accumulated predominantly in the thymus and spleen (FIG. 3). This suggests that 2'-deoxyadenosine cytotoxicity may be involved in the immunodeficiency observed. 2'-Deoxyadenosine can be cytotoxic to cells by directly inhibiting the enzyme AdoHcy hydrolase (Hershfield, 1979; Hershfield et al., 1979). This inhibition can lead to the accumulation of AdoHcy that in turn functions as an inhibitor of transmethylation reactions that utilize S-adenosylmethionine (AdoMet) as a methyl donor (Hershfield and Mitchell, 1995; Hershfield et al., 1979). AdoHcy has also been shown to modulate Apo-1 mediated apoptosis (Ullman et al., 1989). AdoHcy hydrolase enzymatic activity was inhibited in all tissues examined in ADA deficient mice with the greatest degree of inhibition occurring in the thymus and spleen (FIG. 4A). Therefore, disruption of critical transmethylation reactions or induction of apoptosis following AdoHcy hydrolase inhibition, may play a key role in the immune phenotype observed. Little is known regarding transmethylation reactions that may be affected; however, ADA deficient mice will serve as a tool to uncover potential transmethylation targets.

Accumulation of dATP in red blood cells of ADA deficient patients has long been used as a benchmark for the severity of this metabolic disorder (Hershfield and Mitchell, 1995; Cohen et al., 1978; Coleman et al., 1978). dATP is not only elevated in red blood cells of ADA deficient mice, but in all tissues examined (FIG. 4B). Levels of dATP in ADA deficient thymuses and spleens were amongst the highest measured, suggesting that the phosphorylation of 2'-deoxyadenosine to dATP may play a role in the ensuing immune phenotype. Elevated dATP can interfere with deoxynucleotide metabolism by acting as an allosteric inhibitor of ribonucleotide reductase, an essential enzyme in the production of deoxynucleotides utilized in DNA synthesis and repair (Ullman et al., 1978; Cohen et al., 1978; Ullman et al., 1989; Seto et al., 1985). The existence of an ADA deficient mouse will allow for further genetic manipulation and biochemical analysis to assess the role of these mechanisms in the immune phenotype associated with ADA deficiency.

The fact that ADA deficient murine fetuses die perinatally (Wakamiya et al., 1995; Migchielsen et al., 1995), whereas ADA deficient humans do not (Hersfield and Mitchell, 1995), suggests that there is a significant difference in the requirement for ADA during prenatal stages of murine and human development. This difference is manifested in the high levels of ADA that are found in the murine placenta (Knudsen et al., 1991) that do not appear to be present in the human placenta (Dooley et al., 1987). Despite this prenatal difference, results from this study show that once ADA deficient fetuses have been rescued from perinatal lethality, the postnatal phenotypes observed are similar to those seen in ADA deficient children. This similarity extends beyond the combined immunodeficiency to include a pulmonary insufficiency, bone abnormalities, and kidney findings. Many of these observations in humans were made during patient autopsy (Ratech et al., 1985; Cederbaum et al., 1976), making it difficult to establish whether these phenotypes are a primary effect of ADA deficiency or secondary to the immunodeficiency. The metabolic disturbances seen in effected organs suggests that these phenotypes may be a primary consequence of ADA deficiency related to perturbations in adenosine signaling. Though the mechanisms by which the metabolic disturbances lead to tissue damage are still not understood, it is clear that these mice provide a model system to learn more about pathways involved in the ontogeny of these phenotypes in ADA deficient mice and humans. In addition, these genetically engineered mice make possible a wide range of biochemical and immunological observations that are not permissible in humans, which will be directed at understanding the mechanism and treatment of ADA deficiency. In particular, ADA deficient mice aid the advancement of enzyme and gene therapy to treat this and related disorders in humans.

5.2 Example 2

ADA Deficient Mice Rescued by Placental Expression Develop Significant Lung Eosinophilia and Lung Damage at an Early Age 5.2.1 Materials and Methods 5.2.1.1 Histological Analysis and Immunofluorescence At the appropriate age, animals were sacrificed and the lungs infused with 0.25 to 0.5 ml of fixative (4% paraformaldehyde in PBS). Infused lungs were then placed in fixative overnight at 4 degrees C., rinsed in PBS, dehydrated and embedded in paraffin according to standard techniques. 5 micron sections were collected on microscope slides and stained with H&E (Shandon-Lipshaw) or PAS (EM Science) according to manufacturers instructions. Immunofluorescence of lungs for the expression of mMPB-1 was performed according to established procedures (Lee et al., 1997). Sections were reacted with antiserum from a rabbit immunized with purified mMBP-1, followed by detection using FITC-conjugated anti-rabbit IgG. Slides were viewed and photographed using an Olympus BX60 microscope equipped with a Spot digital camera (Diagnostics Instruments) interfaced to a computer where images were manipulated using Adobe Photoshop 5.0.

5.2.1.2 Bronchial Alveolar Lavages

Mice were anesthetized with avertin and the trachea exposed using blunt dissection. After securing a blunted 21-gauge needle into the trachea, the lungs were lavaged 5 times with 0.25 ml PBS. Lavages from individual animals were pooled and on average 0.95 to 1 ml of lavage fluid was recovered. Samples were centrifuged at 2,500 rpm for 5 min to recover cells. Supernatant from these spins were collected and stored at −70 degrees C. for the analysis of cytokines. Cells were resuspended in 200 microliter PBS, an aliquot counted using a hemocytometer and another aliquot cytospun onto microscope slides where cells were stained with Diff-Quick (Dade) for cellular differentials. 400 cells per sample were identified and counted under oil immersion.

5.2.1.3 Elisa Assays

IFNg, IL-4 and IL-5 levels in BALF were determined using specific murine OptiEA ELISA kits from Pharmagen according to manufactures instructions. For the analysis of IgE levels, blood was collected from the heart of anesthetized mice and the serum separated by centrifugation of samples at 3,000 rpm for 10 min a 4 degrees C. A murine OptiEA ELISA kit from Pharmagen was utilized to quantitate serum IgE levels. Values were read and quantitated at linearity using a MRX II plate reader equipped with Revelation software (Dynex Technologies).

5.2.2 Results

The expression of ADA in the placenta of ADA deficient fetuses rescues them from perinatal lethality by preventing the accumulation of ADA substrates that are harmful to the developing liver and lung (Blackburn et al., 1996). With the loss of the placenta at birth, these mice are completely ADA deficient. ADA deficient mice begin to show signs of respiratory disease as early as postnatal day 12. This distress was characterized by rapid and labored breathing that became increasingly severe and the mice became cyanotic and died between postnatal day 19 and 22 (Blackburn et al., 1998). The penetrance of this phenotype was 100% among ADA deficient mice, suggesting that the respiratory distress seen was likely a direct effect of the absence of ADA enzymatic activity. This was supported further by our inability to detect respiratory infection in these mice. To begin to assess the nature of the respiratory distress, inflammatory changes were examined in ADA deficient lungs. The lungs of control and ADA deficient mice were lightly stained with hemotoxylin and eosin. An increase in inflammatory cells was seen throughout ADA deficient lungs. Control airways were relatively free of inflammatory cells, whereas large numbers of eosinophils were found in the airways of interstitium of ADA deficient mice. In particular, there was a diffuse increase in alveolar macrophages in the alveolar spaces, and these macrophages appeared enlarged and foamy, indicative of giant cell formation. Closer examination of cells collected from bronchial alveolar lavage fluid (BALF) showed alveolar macrophages engulfing eosinophils and forming multinucleated giant cells. Histological analysis also suggested that there was a pronounced infiltration of eosinophils into the lungs of ADA deficient mice. Lung sections were reacted with a polyclonal antibody against murine eosinophil granule major basic protein-1 (mMBP-1) (Lee et al., 1997), to confirm that the granulocytes identified by H&E staining were eosinophils. Results from these studies confirm the accumulation of eosinophils in ADA deficient lungs. Eosinophils were found in both the interstitiary and lumenal spaces throughout the lung with high concentrations accumulating around bronchioles and pulmonary blood vessels. In addition, there was a large increase in eosinophils found in BALF (FIG. 5A). Notable increases in lymphocytes and neutrophils in BALF were not seen (FIG. 5A). A 3-fold increase in circulating eosinophils was also noted, however, inflammation was not seen in other tissues that were examined, including the gastrointestinal tract, thymus, spleen, liver and kidney. These results demonstrate that ADA deficient mice develop pronounced pulmonary inflammation characterized by the accumulation of activated alveolar macrophages and eosinophils.

In addition to the extensive pulmonary inflammation, lung tissue alterations were also noted in ADA deficient mice. At the earliest stages of respiratory distress (postnatal days 12 to 17) a thickening of the smooth muscle surrounding the medium sized airways was observed. By day 19, there was severe damage in the airways of ADA deficient mice. This included a thickening and shedding of the airway epithelium, extensive mucus secretion, and occlusion of the airways with cellular debris and mucus. In addition to airway damage, general parenchymal inflammation was noted at later stages of the disease. The inflammation and damage seen in ADA deficient lungs was inconsistent with infection, and experimental efforts to detect infection were negative. Rather, the inflammation and damage seen in ADA deficient lungs was reminiscent of those seen in humans suffering asthma exacerbations (Cochrane et al., 1996; Gleich, 1990), and idiopathic eosinophilic pneumonia (Shijubo et al., 1994).

Allergic diseases such as asthma are often but not always associated with increases in serum IgE levels, and with a specific profile of cytokine production known as a type 2 cytokine response (Vogel, 1997; Gleich, 1990; Strek and Leff, 1997). This response includes increased production of interleukin (IL)-4 and IL-5, but not interferon gama (IFN-g). We analyzed serum IgE and cytokine levels in BALF of 18 day old ADA deficient mice (FIG. 6), in order to investigate whether or not the lung inflammation seen in ADA deficient mice was associated with increases in serum IgE or a type 2 cytokine profile. Serum IgE levels were somewhat elevated in the serum of ADA deficient mice (FIG. 6A). There was not a significant difference in the levels of IFNg or IL-4 in ADA deficient BALF, and only a slight increase in the levels of IL-5 (FIG. 6B). These results suggest that a robust type 2 cytokine response is not evident in ADA deficient BALF.

ADA deficient mice exhibited an increase in serum IgE levels, but not a robust type 2 cytokine response that is often seen in association with lung eosinophilia (Vogel, 1997; Gleich, 1990; Strek and Leff, 1997). ADA deficient mice exhibit a combined immunodeficiency (Blackburn et al., 1998); however, the severity of the immunodeficiency is not as complete as that commonly seen in ADA deficient humans (Hershfield and Mitchell, 1995). The lack of a type 2 response may therefore be due to the diminished immune system of these mice. Interestingly, there is evidence to suggest that humans with late- or adult-onset ADA deficiency exhibit increased levels of IgE, eosinophilia, and may develop asthma at a higher rate than the general population (Hirschhorn, 1999). These observations, together with our findings in ADA deficient mice raise the possibility that metabolic disturbances associated with ADA deficiency, namely the accumulation of adenosine, may play a direct role in mediating eosinophilia.

5.3 Example 3

The Eosinophilia and Lung Damage Seen in ADA Deficient Mice is Reversible and Dependent on the Levels of Adenosine in the Lung

5.3.1 Materials and Methods

5.3.1.1 ADA Enzyme Therapy and Zymogram Analysis of ADA Enzyme Activity

PEGADA, also known as ADAGEN, was obtained through collaboration with Enzon Inc. (Piscataway, N.J.). Control or ADA deficient mice were lightly anesthetized and injected intramuscularly with 10 microlitetrs of PEGADA corresponding to approximately 2.5 Units of ADA. Injections were given either chronically every 4 days starting at postnatal day 4, or acutely, as one injection on postnatal day 18. Levels of ADA enzyme activity in tissues was measured using zymogram analysis according to established procedures (Blackburn et al., 1998). This procedure visualizes enzyme activity on non-denaturing agarose gels (Blackburn et al., 1998).

5.3.1.2 Quantification of Adenosine

Mice were anesthetized with avertin, the thoracic cavity exposed, and the lungs were removed and frozen rapidly in liquid nitrogen to prevent metabolism of adenine nucleotides and nucleosides. Adenine nucleosides were extracted from frozen lungs using 0.4 N perchloric acid as described (Knudsen et al., 1992), and adenosine was separated and quantitated using reversed phase HPLC according to established procedures (Knudsen et al., 1992). Adenosine levels were normalized to protein content and values are given as nanomoles of adenosine per milligram protein.

5.3.2 Results

The lung eosinophilia and damage seen in ADA deficient mice may be the result of perturbed adenosine signaling. An important step in determining that the eosinophilia and damage seen in the lung is associated with elevations in lung adenosine levels is to modulate adenosine levels in the lungs of ADA deficient mice and correlate changes with altered phenotype. The inventors have taken a biochemical approach to manipulate adenosine levels in ADA deficient mice.

Polyethylene glycol modified ADA (PEGADA) enzyme therapy is a lifesaving strategy used to treat ADA deficient humans (Hershfield et al., 1993). A weekly intramuscular injection of PEGADA prevents the accumulation of ADA substrates in ADA deficient humans allowing them to survive. The inventors treated ADA deficient mice with intramuscular injections of PEGADA (ENZON, Inc.; Piscataway, N.J.) in an attempt to modulate the respiratory distress seen. Mice were treated intramuscularly with 300 units of PEGADA. They found that mice maintained on weekly injections of PEGADA from birth never develop pulmonary problems and survive as long as the animals are maintained on PEGADA. Even more striking was the observation that PEGADA could reverse the phenotype of an ADA deficient animal after its onset. ADA deficient animals were allowed to develop severe lung inflammation and damage (day 17), and were then treated with PEGADA. Within 24 to 48 hours their respiratory status was noticeably improved, and these animals recovered and survived as long as they were maintained on PEGADA. If however, PEGADA therapy was stopped, animals rapidly showed signs of pulmonary insufficiency and died within a week.

Cell populations were monitored in BALF collected from ADA deficient mice 72 hours following treatment with PEGADA (FIG. 5A), in order to determine what effect PEGADA treatment had on lung inflammation. The number of eosinophils in BALF of ADA deficient mice treated with PEGADA was greatly reduced. Interestingly, alveolar macrophages remained elevated. PEGADA enzyme therapy had no effect on the levels of serum IgE or BALF cytokines. These studies demonstrate that PEGADA enzyme therapy leads to a reduction in lung eosinophilia and rescues ADA deficient mice from terminal respiratory distress.

The rapid reversal of respiratory distress and lung eosinophilia following PEGADA enzyme therapy prompted the inventors to examine the levels of adenosine in the lungs of ADA deficient mice treated with PEGADA (FIG. 5B). The levels of adenosine in control lungs at day 18 were less than 0.2 nmoles per mg protein, whereas those measured in ADA deficient lungs were elevated greater than 20-fold (6.3 nmoles/mg protein). Strikingly, 72 hrs following treatment with PEGADA, adenosine levels were lowered to near control levels in ADA deficient lungs. These studies demonstrate that PEGADA enzyme therapy can efficiently remove adenosine from the lungs of ADA deficient mice, and suggest that adenosine may play a role in regulating lung eosinophilia.

5.4 Example 4

Genetically Preventing Adenosine Accumulation in ADA Deficient Lungs Prevents Inflammation and Lung Damage The inventors have used a genetic strategy that prevented adenosine accumulation in the lungs of ADA deficient mice. Transgenic mice were generated that expressed an ADA minigene in trophoblast cells prenatally and in the forestomach postnatally. This was accomplished by making mice that utilized a trophoblast specific regulatory element together with forestomach specific gene regulatory elements to drive expression of a murine ADA cDNA (Blackburn et al., 1995). This transgene was then mated onto a background heterozygous for the null Ada allele, generating animals that were transgenic for the trophoblast/forestomach specific ADA minigene and heterozygous for the null Ada allele. Subsequent matings generated ADA deficient mice that were rescued from perinatal lethality due to expression in trophoblasts, and postnatally, contained ADA only in the gastrointestinal track, predominantly the forestomach (Blackburn et al., 1996). These animals did not show any signs of respiratory distress and live a normal lifespan.

The phenotypic and biochemical effect of expressing ADA only in the forestomach of ADA deficient mice was examined. Control mice, mice completely ADA deficient, and mice expressing ADA only in the forestomach were sacraficed on postnatal day 15 and lung tissue examined histologically and for levels of adenosine. The severe lung inflammation and damage seen in ADA deficient mice is prevented by forestomach expression of ADA. The levels of adenosine in control lungs are detectable (<0.3 nmoles per mg protein), but are relatively low in comparison to levels measured in the lungs of ADA deficient mice (7.4 nmoles per mg protein). In mice only expressing ADA in the forestomach, adenosine levels in the lungs were greatly reduced (1.0 nmole per mg protein). While low levels of ADA are normally found in the lung, it is not necessary to restore ADA to the lung to prevent adenosine accumulation in the lung or to prevent lung inflammation and damage.

This demonstrates that adenosine accumulation and subsequent phenotypes are a systemic process and that it is not necessary to place ADA back in the lung itself to lower adenosine levels.

The inventors have generated another line that expresses low levels of ADA only in the gastrointestinal tract. These mice develop severe lung inflammation and damage, but at a later stage. Instead of dying at 3 weeks like fully ADA deficient mice, this new line of mice do not develop respiratory problems until 5 weeks and die between 5 and 9 weeks. This is associated with the expression of ADA in the gut keeping adenosine levels below threshold levels which extend the lifespan of the animals. Thus, by adjusting the level of ADA in an animal, one may vary the degree of respiratory disorder in the animal.

5.5 Example 5
Assesment of Airway Function

Initial studies performed in BALB/c mice revealed an increased airway response to methacholine (Mch) after RSV infection and ovalbumin sensitization and challenge (FIG. 7A) (Colasurdo et al., 1995). The average Mch-dose airway response relationships revealed constrictor responses in RSV-infected and ovalbumin challenged animals at various concentrations of Mch. Assessment of airway function was also performed in mice heterozygous for the null Ada allele (129/SV-FVB/N hybrids) due to limited information on pulmonary physiology in the mouse strain used in the generation of ADA deficient mice. Studies performed in two control (heterozygotes) animals revealed similar Mch dose-response relationships when compared to control BALB/c mice in terms of baseline Rrs, ED50 and MR values (FIG. 7B). Taken together, these observations demonstrate that lung physiology in normal, ADA deficient and PEG-ADA animals can be accurately assessed.

5.6 Example 6
Correlation of Placental ADA Expression and the Lack of Adenosine in the Lungs of ADA Deficient Mice The inventors have shown that expression of ADA in the placenta of ADA deficient fetuses rescues them from perinatal lethality (Blackburn et al., 1995). It was proposed that the accumulation of ADA substrates in ADA fetuses were harmful to the liver and lung, and that placental ADA prevented the accumulation of these substrates and thus prevented damage (Blackburn et al., 1996, 98). The lungs, however, were not examined closely in these studies. The inventors have developed several different lines of transgenic mice that express various levels of ADA in the placenta. Each of these lines is likely to show different amounts of lung adenosine accumulation and damage. One may use the techniques of Examples 1 through 5 to access the status of the lungs in these different lines and the effect of the biochemical and genetic treatments on these varying degrees of lung disorder.

A transgenic line rescued with higher levels of placental ADA than the line shown in Example 1, develop pulmonary insufficiency two weeks later than a line expressing lower levels in the placenta. By measuring adenosine levels in prenatal and neonatal mice from this line, as well as others, one may correlate the levels of adenosine the neonatal lung encounters with the onset and severity of the lung eosinophilia and damage seen later.

5.7 Example 7
Role of Adenosine Receptors in Asthma

By mating ADA deficient mice with mice deficient in various adenosine receptors, one may assess the role of these receptors in lung development and predisposition to childhood asthma. To date, the targeted disruption of only one adenosine receptor subtype (A2a), has been described (Ledent et al., 1997). In the Ledent study, there was no mention of respiratory problems or an inflammation phenotype; however, these animals have not been challenged with elevated adenosine levels such as those found in ADA deficient mice. In addition, other laboratories have disrupted the A1 and A3 adenosine receptors. Another receptor that may be knocked out is the A2b adenosine receptor. These various receptor knockouts may be mated onto the ADA deficient background and assess their role in lung development and the development of asthma. This will identify the key adenosine signaling components involved in the lung phenotype seen in ADA deficient fetuses, guide future studies designed at understanding specific signal transduction mechanisms involved, and facilitate the design of new therapies for asthma treatment.

Eosinophils and macrophages both play critical roles in asthma and both are influenced by the engagement of adenosine receptors. High levels of the A3 adenosine receptor are expressed on human eosinophils that accumulate in the lungs of asthmatics (Walker et al., 1997). Engagement of this receptor on eosinophils is thought to mediate the release of $Ca^{+2}$ from intracellular stores (Kohno et al., 1996), and can inhibit eosinophil chemotaxis which may serve pro- or anti-inflammatory roles (Walker et al., 1997; Knight et al., 1997). Whether or not the A3 receptor is expressed in murine eosinophils and in the lungs of ADA deficient mice is currently under investigation. However, the large increase in lung eosinophils in ADA deficient mice, and the ability to rapidly reverse this eosinophilia by lowering adenosine concentrations, suggest adenosine signaling may be mediating the lung eosinophilia. In addition to an increase in eosinophils, the number and activation of alveolar macrophages was greatly increased in the lungs of ADA deficient mice. Engagement of adenosine receptors on macrophages elicits both pro- and anti-inflammatory events including the inhibition of tumor necrosis factor-a expression (Hasko et al., 1996; Sajjadi et al., 1996) and nitric oxide production (Hasko et al., 1996), increased production of IL-10 (Hasko et al., 1996), increased differentiation of monocytes into macrophages (Najar et al., 1990; Eppell et al., 1989), and, depending on the receptor utylized, increased or decreased rates of phagocytosis (Salmon et al., 1993; Eppell et al., 1989). It is possible that the increased number and activity of alveolar macrophages in ADA deficient mice results from aberrant adenosine signaling brought about by persistent elevations in lung adenosine levels.

5.8 Example 8
Assessment of Airway Function

In vivo and in vitro assessment of airway functions are excellent means of determining the physiological status of the lungs in humans and in animal models (Larsen and Colasurdo 1997). ADA deficient mice that have been rescued by placental ADA expression develop lung eosinophilia and damage (Blackburn et al., 1998; Example 2). Furthermore, the inventors have generated several different lines of mice that exhibit varying degrees of respiratory disease based on the amount of ADA expressed in the placenta prenatally or in the gastrointestinal (GI) tract postnatally (Example 4). The most severe phenotype is seen in mice rescued by low levels of expression in the placenta and no postnatal expression of ADA (Blackburn et al., 1998). These animals die from respiratory distress by day 21. Another line does not develop pulmonary distress until 8 weeks of age, dies by 9 weeks, and expresses moderate levels of ADA in the placenta and low levels in the GI tract postnatally. A third line does not develop respiratory symptoms, and lives a normal life span. This line is characterized by high levels of ADA in the placenta, and high levels only in the GI tract postnatally (Example 4). Additional lines of mice may be generated that will express various levels of ADA. The variation in phenotype between these mice is due to varying levels of adenosine. The levels of adenosine in the prenatal and postnatal lungs of these mice may be determined. In vivo airway function may be determined on these mice by the methods of Larsen and Colasurdo (1997). After baseline respiratory resistance is determined on anesthetized mice using a body plethysmograph, dose response curves to methacholine may be performed. Data is then collected following increasing doses of methacholine delivered intravenously. In this manner one may obtain functional assessments of airway responsiveness in the various lines of ADA deficient mice. Baseline data for heterozygous mice that will serve as controls have been obtained and are shown in Example 5, FIG. 7B.

5.9 Example 9
Environmental Factors and Asthma

Environmental factors can lead to worsening airway hyperresponsiveness and exacerbation of asthma symptoms (Barnes, 1995). These environmental factors include viral infections, allergens and other environmental factors (Vogel 1997; Cochrane et al., 1996; Colasurdo and Larsen 1995). In particular, clinical and laboratory observations have repeatedly suggested an association between viral infections and allergen sensitization and the development of airway dysfunction. Due to differences in the mechanisms of injury and remodeling in response to allergens and viruses, both viral infections and antigen sensitization may be used as environmental triggers of airway dysfunction. In this way the involvement of adenosine signaling in these two distinct mechanisms of injury may be assessed. This may be done by exposing various lines of ADA deficient mice to RSV or ovalbumin and then assess in vivo and in vitro changes of airway function. Since susceptibility of various mouse strains is variable (Prince et al., 1979), other pathogens (influenza, parainfluenza, adenovirus, mycoplasma) may be used if necessary. Because some lines of ADA deficient mice die at such an early age, one would not be able to perform these studies on these line. However, one may prolong the life of these animals by maintaining them on PEGADA for 5 weeks, then stop treatment and perform the assessments.

Polyethylene glycol modified ADA (PEGADA) enzyme therapy is a lifesaving strategy used to treat ADA deficient humans (Hershfield et al., 1993). This treatment serves to prevent the accumulation of ADA substrates in the circulatory system. Treatment of ADA deficient mice with PEGADA prevents the accumulation of adenosine in the lung within 48 hours (FIG. 5B). This is associated with a decrease in the number of eosinophils found in the BALs of these mice (FIG. 5A). These data indicate that PEGADA can rapidly remove lung adenosine levels and correct lung damage. PEGADA therapy may be used to assess whether the increased airway responsiveness seen in various lines of ADA deficient mice, or the same mice treated with RSV and ovalbumin, is dependent on adenosine levels. Mice are given intramuscular injections of PEGADA 48 hours before the measurement of lung mechanics. This is done with control mice, various ADA deficient mice, or ADA deficient mice exposed to RSV or ovalbumin appropriately. One may administer PEGADA intranasally to more selectively remove adenosine. Treatment with PEGADA will lower adenosine levels in the lung (FIG. 5B), and an improvement in airway function in both ADA deficient mice and ADA deficient mice exposed to RSV or ovalbumin will be seen.

Various strains of mice respond differently to RSV and ovalbumin challenges (Prince et al., 1979; Zhang et al., 1997). The reason for this is not entirely clear and probably multifactorial. To assess the possibility that the levels of adenosine may influence various responses amongst different strains, one may measure the levels of adenosine and ADA in the lungs of commonly used mouse strains following RSV or ovalbumin challenges. Through these methods one may determine that the effects of environmental factors on the lungs of ADA deficient mice are dependent on elevated adenosine levels.

5.10 Example 10
Methods for RSV Infection and Ovalbumin Sensitization

All animal procedures employed in these studies are approved by the Animal Care and Use Committee of the University of Texas Health Science Center and conformed to the National Institutes of Health guidelines. The human respiratory syncytial virus (HRSV), strain $A_2$, is used in all experiments utilizing RSV. Stocks of this virus are prepared in Hep-2 cells as previously described (Colasurdo, AJP 1995), and were obtained from the American Type Culture Collection, Rockville, Md. Mice (control, ADA deficient and PEG-ADA) are infected at various ages. Under light anesthesia, mice are infected intranasally with $5 \times 10^6$ plaque-forming units (pfu) of virus. Previous studies have shown that under these conditions the inoculum uniformly reached the lungs (Prince 1976). Control animals are given uninfected cell culture medium or non-replicative RSV in a similar manner.

In vivo and in vitro studies of airway function are performed 6 days post-infection when the peak of the pathological changes within lung tissue is obtained. As noted above, additional studies are be performed at various time points post infection. Lung tissues are homogenized in 10 parts (wt/vol) of Hanks balanced salt solution supplemented with 0.218 M sucrose, 4.4 mM glutamate, and 3.8 mM $KH_2HPO_4$ and stored at $-70°$ C. until assayed. The virus titer was determined by a plaque assay on Hep-2 cell monolayers as previously described (Colasurdo et al., 1995) with results expressed in plaque-forming units per gram of tissue.

For ovalbumin sensitization, mice are immunized with an intraperitoneal injection of 50 $\mu$l of PBS containing 4 $\mu$g of OVA (Sigma Chemical Co., St Louis, Mo.) adsorbed to 4 mg of aluminum hydroxide (Sigma) on protocol days 0 and 14. On days 14, 25, 26, 27 and 28, mice are challenged intranasally with 40 $\mu$l of PBS containing 4 $\mu$g of ovalbumin (Zhang et al., 1997). In vivo and in vitro studies of airway function are performed at various time points after the last intranasal exposure to antigen. Mice are anesthetized by an intraperitoneal (ip) injection of ketamine, xylazine and acepromazine. After insertion of a butterfly needle into a tail vein, a polyethylene catheter (3.0 cm in length, 0.81 mm in diameter) is inserted into the trachea through a cervical incision. Each mouse is placed in supine position inside a 0.37-liter Plexiglass pressure-sensitive body plethysmograph for measurement of changes in lung volume (V/t). The tracheal cannula is connected through the plethysmograph wall to a mechanical ventilator (Harvard Apparatus 687). The ventilator provides a quasi-sinusoidal inspiratory flow and allows a passive, quasi-exponential expiratory flow. Muscle paralysis is induced with pancuronium bromide (0.03 mg, ip). The ventilatory setting consists of supplemental oxygen, a tidal volume of $13.0 \pm 1.0$ ml.$Kg^{-1}$ (mean $\pm$SD), respiratory rate of 120 $min^{-1}$, and positive end-expiratory pressure (PEEP) of 5 $cmH_2O$.

The tracheal pressure [Ptr(t)] is measured via a side tap in the tracheal cannula with a calibrated piezoresistive pressure transducer (Fujikura, FMP-02-PG, Lexington, Mass.). A similar transducer is used to measure changes inside the body plethysmograph [Pbox(t)]. All signal are amplified, anti-alias filtered at 10 Hz (8-pole Bessel 902LPF, Frequency Devices, Haverhill, Mass.), digitized with a 12-bit analog-to-digital converter (DT-2801-A, Data Translation, Malborough, Mass.), sampled at 100 Hz, and stored on a computer (Dell, 5133). The software package ANADAT-LABDAT (RHT-Infodat, Montreal, Quebec) is used for acquisition and analysis of the data.

After animals achieve stable peak Ptr values on mechanical ventilation, data are first collected during an intravenous (iv) bolus of 10 $\mu$l of PBS. Data are then sampled during iv injections of methacholine chloride (Mch, Sigma Chemical Co., St. Louis, Mo.), with doses ranging from 25 $\mu$g.kg$^{-1}$ up to 1600 $\mu$g.kg$^{-1}$. A standard volume history is performed approximately 30 seconds before starting data sampling by occluding the outlet of the respirator for 3 consecutive respiratory cycles and inflating the lungs. During data collection, animals are ventilated without PEEP.

The respiratory resistance (Rrs) and dynamic elastance (Edyn, rs) return to baseline values before the increasing concentrations of Mch used. After completion of the Mch challenge, the step response of the plethysmograph is measured with the paralyzed animal in situ and the biexponential decay in Pbox as a function of time is used to convert Pbox data into changes in lung volume (Bates et al., 1989). Flow (v/t) is obtained by numerical differentiation of the volume signal. The pulmonary physiology studies last approximately 45 minutes, during which the average fluid volume injected into each animal is approximately 1.2 ml.

The values for Rsr and Edynrs as a function of time are estimated by applying a recursive least-square algorithm (Lauzon et al., 1991) off-line to the equation of motion of the single-compartment linear model of the respiratory system: Ptr(t)=Rrs' V(t)+Edyn,rs' V(t)+K, where K is a constant to account for any airway pressure at the end of expiration. The coefficient of determination of the multiple linear regression analysis is >0.98 in all instances. The resistance and elastance of the measuring equipment is estimated and their values subtracted from Rrs' and Edyn.rs', respectively, to give the intrinsic values for the respiratory system resistance (Rrs) and dynamic elastance (Edyn, rs). Methacholine dose-response curves are constructed using Rrs as an index of airway caliber. The maximal constrictor response (MR) and ED50 values (dose of Mch that produces 50% of the maximal contractile response) are obtained as mean ±SE.

In the dose-response curve, a plateau or MR is considered to be present when, for 3 consecutive increasing doses of Mch, Rrs either increases by less than 15% or decreases after attaining a maximum value. In selected experiments, in vitro study of airway function may be performed on airway smooth muscle (ASM) segments obtained from animals after the various treatments detailed under Research Design. In these studies, assessments of neurally-mediated contractile and relaxant responses of TSM are performed to evaluate the effects of RSV infection on pre- and post-junctional mechanisms that are involved in the regulation of ASM function (Colasurdo et al., 1995; Colasurdo et al., 1994; Colasurdo et al., 1998).

5.11 Example 11
Methods for Screening for Compounds for Treatment of Skeletal System Dysfunctions Associated with Elevated Adenosine To identify a candidate substance as being capable of effecting dysfunctions in the skeletal system associated with elevated adenosine levels, one would measure or determine various characteristics of the skeletal system of the ADA deficient animal, in the absence of the added candidate substance. One would then administer the candidate substance to the animal and determine the response in the presence of the candidate substance. A candidate substance which effects the dysfunction in the skeletal system or decreases systemic adenosine levels in comparison to its absence, is indicative of a candidate substance with therapeutic capability.

ADA deficient humans have been shown to have abnormalities associated with their skeletal system (Ratech et al., 1985). These abnormalities include severe curvature of the rib cage, thickening of the costochondral junctions, and abnormal growth plates in the long bones and vertebrae. Similarly, the ADA deficient mice generated by this invention exhibit severe bony abnormalities, including severe rib curvature and thickening of costochondral junctions (Blackburn, et al., 1998). It is likely that the bony abnormalities result from the severe metabolic disturbances associated with ADA deficiency. The invention will be useful in defining the signaling mechanisms involved in this phenotype as well as testing compounds that might be useful in the treatment of bony abnormalities. These can be assessed in the mice by examining the skeletal system histologically or macroscopically using staining procedures such as alyzarin red and azure blue (Blackburn et al., 1998).

5.12 Example 12
Methods for Screening for Compounds for Treatment of Renal System Dysfunctions Associated with Elevated Adenosine To identify a candidate substance as being capable of effecting dysfunctions in the renal system associated with elevated adenosine levels, one would measure or determine various characteristics of the renal system of the ADA deficient animal, in the absence of the added candidate substance. One would then administer the candidate substance to the animal and determine the response in the presence of the candidate substance. A candidate substance which effects the dysfunction in the renal system or decreases systemic adenosine levels in comparison to its absence, is indicative of a candidate substance with therapeutic capability.

Kidney abnormalities have also noted in ADA deficient humans (Ratech et al., 1985). The most common observation is mesengeal sclerosis; however, this phenotype has not been well characterized. ADA deficient mice possess kidney abnormalities as well (Blackburn et al., 1998). Kidneys are normal in size and structure but demonstrate a large increase in red blood cells in the glomeruli and convoluted tubules. It is likely that the kidney abnormalities seen are a consequence of the accumulation of adenosine in the kidney of these mice (Blackburn et al., 1998). There is substantial evidence to suggest that adenosine signaling plays an important role in kidney function (Jackson, 1997). The adenosine A1 and A2a receptors have been described at relatively high concentrations in the kidney and their engagement by adenosine is thought to play an important role in glomerular filtration rate by mediating tubuloglomerular feedback, renin release and tubular transport, and erythropoietin production. All of these components are important for normal kidney function. Abnormal adenosine signaling may effect these kidney functions and lead to acute renal failure or acute tubular necrosis. The invention described here will be useful for studying the role of adenosine signaling in the kidney as well as testing compounds such as adenosine receptor agonists and antagonists for their ability to correct renal dysfunction in these mice.

5.13 Example 13
Methods for Screening for Compounds for Treatment of Immune System Dysfunctions Associated with Elevated Adenosine To identify a candidate substance as being capable of effecting dysfunctions in the immune system associated with elevated adenosine levels, one would measure or determine various characteristics of the immune system of the ADA deficient animal, in the absence of the added candidate substance. One would then administer the candidate substance to the animal and determine the response in the presence of the candidate substance. A candidate substance which effects the dysfunction in the immune system or decreases systemic adenosine levels in comparison to its absence, is indicative of a candidate substance with therapeutic capability.

ADA deficient humans (Hershfield and Mitchell, 1995) and mice (Blackburn et al, 1998) develop a combined immunodeficiency. This is characterized by depletion in the levels of lymphoid cells. The mechanism of lymphoid toxicity is still unknown, but is likely related to the accumulation of the ADA substrates adenosine and deoxyadenosine. Much attention has been given to deoxyadenosine as the cytotoxic metabolite, however, disturbances in adenosine signaling may also be involved (Hershfield and Mitchell, 1995). Adenosine levels are greatly elevated in the thymus and spleen of ADA deficient mice (Blackburn et al., 1998), and the thymus and spleen both show relatively high levels of adenosine receptor expression. It is likely that the elevated levels of adenosine are perturbing normal adenosine signaling in these primary immune organs and in so doing contribute the resulting immunodeficiency. ADA deficient mice will serve as valuble models for studying the mechanisms of adenosine signaling in the immune system as well as serve as an ideal in vivo testing ground for immunotherapy directed at adenosine signaling. This would include the use of specific and nonspecific adenosine receptor agonists and antagonists, followed by assessment of immune status. This includes flow cytometry for the expression of specific lymphoid cell markers, as well as in vivo and in vitro test to assess the function of the immune system.

5.14 Example 14
Methods for Screening for Compounds for Treatment of Cardiovascular and Vascular System Dysfunctions Associated with Elevated Adenosine To identify a candidate substance as being capable of effecting dysfunctions in the cardiovascular and vascular system associated with elevated adenosine levels, one would measure or determine various characteristics of the cardiovascular and vascular system of the ADA deficient animal, in the absence of the added candidate substance. One would then administer the candidate substance to the animal and determine the response in the presence of the candidate substance. A candidate substance which effects the dysfunction in the cardiovascular and vascular system or decreases systemic adenosine levels in comparison to its absence, is indicative of a candidate substance with therapeutic capability.

It is not know whether or not ADA deficient humans or mice exhibit abnormal cardiovascular or vascular pathology or function. However, adenosine signaling is known to play many important roles in these systems (Jacobson and Jarvis, 1997). Furthermore, given the extremely high levels of systemic adenosine that are found in ADA deficient mice (Blackburn et al., 1998), it is likely that perturbations in adenosine signaling are occurring and that these animals will serve as useful models for understanding the role of adenosine signaling in the vascular and cardiovascular system as well as to test the therapeutic efficacy of compounds to treat disorders of these systems that are related to adenosine signaling. The best-characterized function of adenosine signaling in the cardiovascular system is the cardioprotective roles of this signaling pathway, where adenosine signaling leads to cellular changes that collectively serve to increase oxygen supply to tissues. This mechanism becomes important in cases of oxygen depravation that can result from ischemia due to infarction or reprofussion. Adenosine signaling also has an antiarrhythmic effect of cardiac sinus rhythm, and is used in the treatment of ventricular tachycardias. Studies can be performed of ADA deficient mice to determine if there are any vascular and cardiovascular and may then be used to assess the action of various adenosine receptor agonists and antagonists.

5.15 Example 15
Methods for Screening for Compounds for Treatment of Nervous System Dysfunctions Associated with Elevated Adenosine To identify a candidate substance as being capable of effecting dysfunctions in the nervous system associated with elevated adenosine levels, one would measure or determine various characteristics of the nervous system of the ADA deficient animal, in the absence of the added candidate substance. One would then administer the candidate substance to the animal and determine the response in the presence of the candidate substance. A candidate substance which effects the dysfunction in the nervous system or decreases systemic adenosine levels in comparison to its absence, is indicative of a candidate substance with therapeutic capability.

The neurological effects of ADA deficiency in humans and mice is not well characterized. However, ADA deficient children have been described as lethargic, and it has been suggested that this may result from adverse effects of the accumulation of adenosine and subsequent disturbances in adenosine signaling (Hershfield and Mitchell, 1995). Preliminary data from our laboratory suggests that there is a severe reduction in size of the hippocampus region of the brain in ADA deficient mice, suggesting perturbed adenosine signaling may be causing a neurological phenotype in these mice. The two areas that have received the most attention regarding adenosine signaling in the nervous system are adenosine's ability to modulate the release of neurotransmitters from neurons, and its role as a cytoprotective signaling molecule (Dunwiddie and Fredholm, 1997). Given the high levels of adenosine accumulation in ADA deficient mice, these animals will serve as important models for studying the function of adenosine signaling in the nervous system as well as testing the therapeutic efficacy of adenosine receptor agonists and antagonists in the nervous system. This would include studying the cardioprotective effects of adenosine as it pertains to conditions such as sleep apnea, analgesia and stroke.

5.16 Example 16
Methods for Screening for Compounds for Treatment of Reproductive System Dysfunctions Associated with Elevated Adenosine To identify a candidate substance as being capable of effecting dysfunction in the reproductive system associated with elevated adenosine levels, one would measure or determine various characteristics of the reproductive system of the ADA deficient animal, in the absence of the added candidate substance. One would then administer the candidate substance to the animal and determine the response in the presence of the candidate substance. A candidate substance which effects the dysfunction in the reproductive system or decreases systemic adenosine levels in comparison to its absence, is indicative of a candidate substance with therapeutic capability.

ADA deficient children die before reaching reproductive age, so it is not know whether or not reproductive phenotypes occur. In mice, ADA is found a very high levels of the maternal-fetal interface throughout development (Blackburn and Kellems, 1996) where it is thought to play an important role in regulating the levels of ADA substrates. Absence of ADA at the maternal-fetal interface of mice results in early embryo lethality (Blackburn et al., 1997) in association with elevated adenosine and deoxyadenosine levels. In addition, unpublished results in our lab have shown that there are high levels of adenosine receptors expressed at the maternal-fetal interface during early embryonic stages. This suggests that adenosine signaling may be playing a role in early embryonic events. ADA deficient mice will be useful in deciphering the role of adenosine signaling at the maternal interface as well as in testing the use of adenosine receptor agonists and antagonists as agents to improve reproductive status. This would include using adenosine receptor agonists and/or antagonists as potential anti-abortive drugs.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,329,332, issued May 11, 1982.
U.S. Pat. No. 4,489,055, issued Dec. 18, 1984.
U.S. Pat. No. 4,913,908, issued Apr. 3, 1990.
U.S. Pat. No. 5,451,410, issued Sep. 19, 1995.
U.S. Pat. No. 5,500,224, issued Mar. 19, 1996.
U.S. Pat. No. 5,556,617, issued Sep. 17, 1996.
U.S. Pat. No. 5,620,708, issued Apr. 15, 1997.
U.S. Pat. No. 5,641,515, issued Jun. 24, 1997.
U.S. Pat. No. 5,698,515, issued Dec. 16, 1997.
U.S. Pat. No. 4,215,051
U.S. Pat. No. 4,237,224
U.S. Pat. No. 4,430,434
U.S. Pat. No. 4,554,101
U.S. Pat. No. 4,559,302
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,683,195
U.S. Pat. No. 4,683,202
U.S. Pat. No. 4,727,028
U.S. Pat. No. 4,797,368
U.S. Pat. No. 4,800,159
U.S. Pat. No. 4,873,191
U.S. Pat. No. 4,883,750
U.S. Pat. No. 4,959,317
U.S. Pat. No. 4,960,704
U.S. Pat. No. 5,139,941
U.S. Pat. No. 5,175,384
U.S. Pat. No. 5,175,385
U.S. Pat. No. 5,279,721
U.S. Pat. No. 5,530,179
U.S. Pat. No. 5,565,186
U.S. Pat. No. 5,612,486
U.S. Pat. No. 5,616,491
U.S. Pat. No. 5,625,125
U.S. Pat. No. 5,639,457
U.S. Pat. No. 5,730,983
EPA No. 329 822
EPO 0273085
GB Application No. 2 202 328
PCT/US87/00880
PCT/US89/01025
WO 89/06700
WO 88/10315
WO 90/07641
Abraham, Baugh, Busse and Holgate, "Animal models of asthma," In: *Asthma and Rhinitis,* Blackwell Ed., Inc, Boston, 961–977, 1995
Abremski and Hoess, *Protein Eng.,* 5(1): 87–91, 1992.
Abremski et al., *J. Mol. Biol.,* 202:59–66, 1988.
Abuin and Bradley, *Mol. Cell. Biol.,* 16:1851–1856, 1996.
Allen and Choun, "Large unilamellar liposomes with low uptake into the reticuloendothelial system," *FEBS Lett.,* 223:42–46, 1987.
Alt et al., *J. Biol. Chem.,* 253:1357, 1978.
Andrews et al., *Cell,* 40:795–803, 1985.
Angel et al., *Cell,* 49:729, 1987b.
Angel et al., *Mol. Cell. Biol.,* 7:2256, 1987a.
Arch and Newsholme, "The control of the metabolism and the hormonal role of adenosine," *Essays in Biochem* 14:82–103, 1978.
Asrhady, *J Mol Recognit.,* 9(5–6): 536–542, 1996.
Atchison and Perry, *Cell,* 46:253, 1986.
Atchison and Perry, *Cell,* 48:121, 1987.
Austin et al., *Cell,* 25:729–736, 1981.
Azzawi, Bradley, Jeffrey, "Identification of activated T lymphocytes and eosinophils in bronchial biopsies in stable atopic asthma," *Am. Rev. Respir. Dis.* 142:1407–1413, 1990.
Bahnemann et al., *Abs. Pap. ACS,* 180:5, 1980.
Baichwal and Sugden, In: *Gene transfer,* Kucherlapati R, ed., New York: Plenum Press, 117–148, 1986.
Banerji et al., *Cell,* 27:299, 1981.
Banerji et al., *Cell,* 35:729, 1983.
Barker, Fetal and infant origin of adult disease. *B. M. J.,* 1992.
Barnes, "Current Therapies for Asthma: Promise and Limitations," *Chest* 111:17S–26S, 1997.
Barnes, "A new approach to the treatment of asthma," *N. Engl. J. Med.* 321:1517–1527, 1989.
Barnes, "Pathophysioogy of asthma," *Br. J. Pharmacol.* 42, 3–10, 1995.
Bates, "Correcting for the thermodynamic characteristics of a body plethysnograph," *Ann. Biomed. Eng.* 17:647–655, 1989.

Beasley, Roche, Roberts, Holgate, "Cellular events in the bronchi in mild asthma and after bronchial provocation," *Am. Rev. Respir. Dis.* 139:806–817, 1989.

Bellusci, Furuta, Rush, Henderson, and Winnier, "Involvement of sonic hedgehog (shh) in mouse embryonic lung growth and morphogenesis," *Development* 124:53–63, 1997.

Berkhout et al., *Cell,* 59:273, 1989.

Blackburn, and Kellems, "Regulation and function of adenosine deaminase in mice," in *Progress in Nucleic Acid Research and Molecular Biology,* W. E. Cohn and K. Moldave, eds., Academic Press, New York. Vol. 55, pp 195–226, 1996.

Blackburn, Datta, and Kellems, "A two stage genetic engineering strategy yields adenosine deaminase deficient mice with combined immunodeficiency," *J. Biol. Chem.,* 273:5093–5100, 1998.

Blackburn, Datta, Wakamiya, Vartabedian, and Kellems, "Metabolic and immunological consequences of partial adenosine deaminase deficiency in mice," *J. Biol. Chem.,* 271:15203–15210, 1996.

Blackburn, Gao, Airhart, Skalko, Thompson and Knudsen, "Adenosine levels in the postimplantation mouse uterus: Quantitation by HPLC-fluorometric detection and spatiotemporal regulation by 5' nucleotidase and adenosine deaminase," *Dev. Dynam.,* 194:155–168, 1992.

Blackburn, Knudsen and Kellems, "Genetically engineered mice demonstrate that adenosine deaminase is essential for early postimplantation development" *Development* 124:3089–3097, 1997.

Blackburn, Wakamiya, Caskey and Kellems, "Tissue-specific rescue suggests that placental adenosine deaminase is important for fetal development in mice," *J. Biol. Chem.,* 270:23891–23894, 1995.

Blaese, In: *The Metabolic and Molecular Basis of Inherited Disease.* (Scriver, C. R., Beaudet, A. L., Sly, W. S., and Valle, D., eds) Vol. 3, pp. 3895–3909, McGraw-Hill, Inc., New York, 1995a.

Blaese, *Pediatr. Res.* 33:S49–S55, 1995b.

Blanar et al., *EMBO J.,* 8:1139, 1989.

Bodine and Ley, *EMBO J.,* 6:2997, 1987.

Bollinger, Arredondo-Vega, Santisteban, Schwarz, Hershfield and Lederman, *N. Engl. J. Med.* 334:1367–1371, 1996.

Bordingon, Notarangelo, Nobili, Ferrari, Casorati, Panina, Mazzolari, Maggioni, Rossi, Servida, Ugazio and Mavilia, *Science* 270:470–480, 1995.

Boshart et al., *Cell,* 41:521, 1985.

Bosze et al., *EMBO J.,* 5:1615, 1986.

Bousquet, Chanez and Lacoste, "Eosinophilic inflammation in asthma," *N. Engl. J. Med.* 323:1033–1039, 1990.

Braddock et al., *Cell,* 58:269, 1989.

Bradley et al., *Current Topics in Devel. Biol.,* 20:357–371, 1986.

Brinster et al., Proc. Nat'l Acad. Sci. USA, 82:4438–4442, 1985.

Bruns et al., Proc. Natl. Acad. Sci. U.S.A., 80:2077–2080, 1983.

Bruns, Lu, Pugsley, *Mol. Pharmacol.,* 29:331–346, 1986.

Bruns et al., *Mol. Pharmacol.,* 38:939–949, 1990.

Brusselle, Kips, Joos, Buethman and Pawels, "Allergen-induced inflammation and bronchial responsiveness in wild-type and interleukin-4-deficient mice," *Am. J. Respir. Cell Mol. Biol.* 12:254–259, 1995.

Bulla and Siddiqui, *J. Virol.,* 62:1437, 1986.

Burrows, Fernando, Martinez, Halonen, Barbee and Cline, "Relationship between airway responsiveness and serum IgE in children with asthma and in apparently normal children," *N. Engl. J. Med.* 325:1067–1071, 1989.

Burrows, Knudson and Lebowitz, "The relationship of childhood respiratory illness to adult obstructive airway disease," *Am. Rev. Respir. Dis.* 115:751–760, 1977.

Busse, Banks-Schlegel and Larsen, "Childhood-versus adult-onset asthma. NHLBI Workshop Summary," *Am. J. Respir. Crit. Care Med.* 151:1635–1639, 1995.

Calvo, Vila-Jato and Alonso, "Effect of lysozyme on the stability of polyester nanocapsules and nanoparticles: stabilization approaches," *Biomaterials,* 18(19):1305–1310, 1997.

Calvo, Vila-Jato and Alonso, "Improved ocular bioavailability of indomethacin by novel ocular drug carriers," *J. Pharm. Pharmacol.,* 48(11):1147–1152, 1996.

Campbell and Villarreal, *Mol. Cell. Biol.,* 8:1993, 1988.

Campere and Tilghman, *Genes and Dev.,* 3:537, 1989.

Campo et al., *Nature,* 303:77, 1983.

Capaldi et al., *Biochem. Biophys. Res. Comm.,* 76:425, 1977.

Cederbaum, Kaitila, Rimoin and Stiehm, *J. Pediatr.* 89:737–742, 1976.

Celander and Haseltine, *J. Virology,* 61:269, 1987.

Celander et al., *J. Virology,* 62:1314, 1988.

Chalfie et al., *Science,* 263:802–805, 1994.

Chandler et al., *Cell,* 33:489, 1983.

Chang et al., *Hepatology,* 14:134A, 1991.

Chang et al., *Mol. Cell. Biol.,* 9:2153, 1989.

Chatterjee et al., *Proc. Natl. Acad. Sci. USA.,* 86:9114, 1989.

Chen and Okayama, *Mol. Cell. Biol.,* 7:2745–2752, 1987.

Choi et al., *Cell,* 53:519, 1988.

Clark et al., *Human Gene Therapy,* 6:1329–1341, 1995.

Cochrane, Jackson and Rees, *Asthma: Current Perspectives,* Mosby-Wolf, London, 1996.

Coffin, In: *Virology,* Fields et al. (eds.), New York: Raven Press, pp. 1437–1500, 1990.

Cohen et al., *J. Cell. Physiol.,* 5:75, 1987.

Cohen, Hirschhorn, Horowitz, Rubinstein, Polmar, Hong. and Martin, Jr., *Proc. Natl. Acad. Sci. USA* 75:472–476, 1978.

Colasurdo, Larsen, Busse and Holgate, "Airway hyperresponsiveness," In: *Asthma and Rhinitis,* Blackwell Scientific Publications, Inc, Boston, 1044–1056, 1995.

Colasurdo, Hemming, Prince, Gelfand, Loader and Larsen, "Human respiratory syncytial virus produces long-lasting alterations of airway function in developing ferrets," *Am. J. Respir. Crit. Care Med.,* In press, 1998.

Colasurdo, Hemming, Prince, Loader, Graves and Laresn, "Human respiratory syncytila virus affects nonadrenergic noncholinergic inhibition in cotton rat airways," *Am. J. Physiol.* 268:L1006–L1011, 1995.

Colasurdo, Loader, Graves and Larsen, "Maturation of the nonadrenergic noncholinergic inhibitory system in normal and allergen-sensitized rabbits," *Am. J. Physiol.* 267:L739–L744, 1995.

Colberre-Garapin et al., *J. Mol. Biol.,* 150:1, 1981.

Coleman, Donofrio, Hutton, Hahn, Daoud, Lampkin, and Dyminski, *J. Biol Chem.* 253:1619–1626, 1978.

Costa et al., *Mol. Cell. Biol.,* 8:81, 1988.

Cotten et al., *Proc. Natl. Acad. Sci. USA,* 89:6094–6098, 1992.

Couch et al., *Am. Rev. Resp. Dis.,* 88:394–403, 1963.

Coupar et al., *Gene,* 68:1–10, 1988.

Couvreur et al., "Nanocapsules, a new lysosomotropic carrier," *FEBS Lett.,* 84:323–326, 1977.

Couvreur, "Polyallyleyanoacrylates as colloidal drug carriers," *Crit. Rev. Ther. Drug Carrier Syst.,* 5:1–20, 1988, 1978.

Cripe et al., *EMBO J.,* 6:3745, 1987.
Culotta and Hamer, *Mol. Cell. Biol.,* 9:1376, 1989.
Cumo and Oettinger, *Nucl. Acids Res.,* 22(10):1810–1814, 1994.
Curiel, In: *Viruses in Human Gene Therapy,* J.-M. H. Vos (Ed.), Carolina Academic Press, Durham, N.C., 179–212, 1994.
Cushley, Tattersfield and Holgate, "Inhaled adenosine a guanosine on airway resistance in normal and asthmatic subjects," *Br. J. Clin. Pharmacol.* 15:161–167, 1983.
Cushly et al., *Am. Rev. Respir. Dis.,* 129:380–384, 1984.
Dale and Ow, *Proc. Natl. Acad. Sci. USA,* 88:10558–10562, 1991.
Damge, Vonderscher, Marback, Pinget, "Poly(alkyl cyanoacrylate) nanocapsules as a delivery system in the rate for octreotide, a long-acting somatostatin analogue," *J. Pharm. Pharmacol.,* 49(10):949–954, 1997.
Dandolo et al., *J. Virology,* 47:55, 1983.
De Villiers et al., *Nature,* 312:242, 1984.
Deschamps et al., *Science,* 230:1174, 1985.
Di Marco et al., *J. Am. Col. Cardiol.,* 6:417–425, 1985.
Dixon, Gubita, Sirinathsinghji, Richardson, and Freeman, "Tissue distribution of adenosine receptor mRNAs in the rat," *Brit J.Pharm.* 118:1461–1468, 1996.
Doherty, Pan, Mulloy, Thompson, Thorner, Barankiewiecz, Roifman and Cohen, *Scand. J. Immunol.* 33:405–410, 1991.
Donofrio, Coleman and Hutton, *J. Clin. Invest.* 62:884–887, 1978.
Dooley, Fairbanks, Simmonds, Rodeck, Nicolaides, Soothil, Stewart, Morgan and Levinsky, *Prenat. Diagn.* 7:561–565, 1987.
Driver, Kukoly, Ali and Mustafa, "Adenosine in bronchoalveolar lavage fluid in asthma," *Am. Rev. Respir. Dis.* 148:91–97, 1993.
Dunwiddie, Fredholm, "Adenosine Neuromodulation," In: *Purinergic Approches in Experimental Therapeutics,* Eds., Jacobson, K. A. and Jarvis, Wiley-Liss Inc., New York. Pp. 359–382, 1997.
Edbrooke et al., *Mol. Cell. Biol.,* 9:1908, 1989.
Edlund et al., *Science,* 230:912, 1985.
Eggleston, Szefler, Busse and Holgate, "Asthma in children," In: *Asthma and Rhinitis,* Blackwell Ed., 1380–1393, 1995.
Evans et al., *Neurosci. Lett.,* 83:287, 1987.
Evans III, Mullally, Wilson, "National trends in morbidity and mortality of asthma in the US: prevalence, hospitalization rate and death from asthma over two decades (1965–1984)," *Chest* 91:65S–74S, 1989.
Fechheimer et al., *Proc. Natl. Acad. Sci. USA,* 84:8463–8467, 1987
Feng and Holland, *Nature,* 334:6178, 1988.
Feokistov and Biaggioni, "Adenosine $A_{2b}$ Receptors Evoke Interleukin-8 Secretion in Human Mast Cells An Enproflyline-sensitive Mechanism with Implications for Asthma," *J. Clin. Invest.* 96:1979–1986, 1995.
Fink, Weaver, Rivkees, Peterfreund, Pollack, Adler and Reppert, "Molecular cloning of the rat A2 adenosine receptor: selective co-expression with D2 dopamine receptors in rat striatum", *Mol. Brain Res.* 14:186–195, 1992.
Firak and Subramanian, *Mol. Cell. Biol.,* 6:3667, 1986.
Flotte et at., *Am. J. Respir. Cell Mol. Biol.,* 7:349–356, 1992.
Flotte et al., *Gene Therapy,* 2:29–37, 1995.
Flotte et al., *Proc. Natl. Acad. Sci. USA,* 90:10613–10617, 1993.
Foecking and Hofstetter, *Gene,* 45:101, 1986.

Forman, Velasco, *Cardiovasc. Drugs and Therapy,* 5:901–908, 1991.
Fraley and Fornari Kaplan, *Proc. Nat'l. Acad. Sci. USA,* 76:3348–3352, 1979
Friedmann, *Science,* 244:1275–1281, 1989.
Frohman, In: *PCR Protocols: A Guide To Methods And Applications, Academic Press,* N.Y., 1990.
Fujita et al., *Cell,* 49:357, 1987.
Fung-Leung et al., *Cell,* 65:443449, 1991a.
Fung-Leung et al., *J. Exp. Med.,* 174:1425–1429, 1991b.
Gabizon and Papahadjopoulos, "Liposomes formulations with prolonged circulation time in blood and enhanced uptake by tumors," *Proc. Natl. Acad. Sci. USA,* 85:6949–6953, 1988.
Gao, Blackburn and Knudsen, *Teratology* 49:1–12, 1994.
Gergen, Mullally and Evans, "National survey of prevalence of asthma among children in the United States (1976–1980)," *Pediatrics* 81:1–7, 1988.
Ghosh-Choudhury et al., *EMBO J.,* 6:1733–1739, 1987.
Ghosh and Bachhawat, *Targeting of liposomes to hepatocytes,* In: Wu G, Wu C ed. Liver diseases, targeted diagnosis and therapy using specific receptors and ligands, New York: Marcel Dekker, pp. 87–104, 1991.
Giblett, Anderson, Cohen, Pollara and Meuwissen, *Lancet* 2:1067–1069, 1972.
Gilles et al., *Cell,* 33:717, 1983.
Gius et al., *J. Virology,* 62:665, 1988.
Gleich, "The eosinophil and bronchial asthma: current understanding," *J. Allergy Clin. Immunol.,* 85:422–436, 1990.
Glezen and Denny, "Epidemiology of acute lower respiratory disease in children," *N. Engl. J. Med.* 288:498–505, 1973.
Gloss et al., *EMBO J.,* 6:3735, 1987.
Godbout et al., *Mol. Cell. Biol.,* 8:1169, 1988.
Godding, Stark., Sedgwick and Busse, "Adhesion of activated eosinophils to respiratory epithelial cells is enhanced by tumor necrosis factor and interleukin-1," *Am. J. Respir. Cell. Mol. Biol.* 13:555–562, 1995.
Gomez-Foix et al., *J. Biol Chem.,* 267:25129–25134, 1992.
Gonzalo, Jia, Aguirre, Friend, Coyle, Jenkins, Lin, Katz, Lichtman, Copeland, Kopf and Guitierrez-Ramos, "Mouse eotaxin expression parallels eosinophils accumulation during allergec inflammation but it is not restricted to a Th2-type response," *Immunity.* 4:1–14, 1996.
Goodbourn and Maniatis, *Proc. Natl. Acad. Sci. USA,* 85:1447, 1988.
Goodbourn et al., *Cell,* 45:601, 1986.
Gopal, *Mol. Cell. Biol.,* 5:1188–1190, 1985.
Graham and Prevec, *Biotechnology,* 20:363–390, 1992.
Graham and Prevec, In: *Gene Transfer and Expression Protocols,* Murray, E. J., ed., Humana, N. J., 7:109–128, 1991.
Graham and Van Der Eb, *Virology,* 52:456–467, 1973.
Graham et al., *J. Gen. Virol.,* 36:59–72, 1977.
Greene et al., *Immunology Today,* 10:272, 1989.
Grosschedl and Baltimore, *Cell,* 41:885, 1985.
Grunhaus and Horwitz, *Seminar in Virology,* 3:237–252, 1992.
Hall, *Respiratory Syncytial Virus.* In: *Textbook of Pediatric Infectious Disease,* R D Feigin and J D Cherry, Saunders Ed., 1633–1656, 1992.
Hall, "Prospects for respiratory syncytial virus vaccine," *Science* 265:1393–1394, 1994.
Harland and Weintraub, *J. Cell Biol.* 101:1094–1099, 1985.
Haslinger and Karin, *Proc. Natl. Acad. Sci. USA.,* 82:8572, 1985.

Hauber and Cullen, *J. Virology*, 62:673, 1988.
Heffner et al., *Psychopharmacology*, 98:31–38, 1989
Hen et al., *Nature*, 321:249, 1986.
Henry-Michelland et al., "Attachment of antibiotics to nanoparticles; Preparation, drug-release and antimicrobial activity in vitro," *Int. J. Pharm.*, 35:121–127, 1987.
Hensel et al., *Lymphokine Res.*, 8:347, 1989.
Hermonat and Muzyczka, *Proc. Nat'l. Acad. Sci. USA*, 81:6466–6470, 1984.
Herr and Clarke, *Cell*, 45:461, 1986.
Hersdorffer et al., *DNA Cell Biol.*, 9:713–723, 1990.
Hershfield.and Mitchell, "Immunodeficiency diseases caused by adenosine deaminase deficiency and purine nucleoside phosphorylase deficiency," In: *The Metabolic and Molecular Basis of Inherited Disease.* (McGraw-Hill, Inc., New York) 1:1725–1768, 1995.
Hershfield,. *J. Biol. Chem.* 254:22–25, 1979.
Hershfield and Mitchell, *The Metabolic and Molecular Basis of Inherited Disease.* (Scriver, C. R., Beaudet, A. L., Sly, W. S., and Valle, D., eds) Vol 1, pp. 1725–1768, McGraw-Hill, Inc., New York, 1995.
Hershfield, Chaffee and Sorensen, "Enzyme replacement therapy with PEG-ADA in adenosine deaminase deficiency: Overview and case reports of three patients, including two now receiving gene therapy," *Pediatr. Res.* 33:S35–S41, 1993.
Hershfield, Kredich, Ownby, Ownby and Buckley, *J. Clin. Invest.* 63:807–811, 1979.
Herz and Gerard, *Proc. Nat'l. Acad. Sci. USA*, 90:2812–2816, 1993.
Hirochika et al., *J. Virol.*, 61:2599, 1987.
Hirsch et al., *Mol. Cell. Biol.*, 10:1959, 1990.
Hirschhorn, "Immunodeficiency disease due to deficiency of adenosine deaminase," In: *Primary Immunodeficiency Diseases: A Molecular and Genetic Approach*, Oxford University Press, New York, 121–139, 1999.
Hoess et al., *Proc. Natl. Acad. Sci. USA*, 79:3398–3402, 1982.
Hogan et al., *Manipulating the Mouse Embryo*, Cold Spring Harbor Laboratory, Cold Spring Harbor, N.Y., 1986.
Holbrook et al., *Virology*, 157:211, 1987.
Horlick and Benfield, *Mol. Cell. Biol.*, 9:2396, 1989.
Horn, Robin, Theodore and Van Kessel, "Total eosinophil counts in the management of bronchial asthma," *N. Engl. J. Med.* 292:1152–1155, 1975.
Horwich et al. *J. Virol.*, 64:642–650, 1990.
Huang et al., *Cell*, 27:245, 1981.
Hwang et al., *Mol. Cell Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
In: *Manipulating the Mouse Embryo; A Laboratory Manual*, 2nd edition, Hogan, Beddington, Costantimi and Long, eds., Cold Spring Harbor Laboratory Press, 1994.
Inouye et al., *Nucleic Acids Res.*, 13:3101–3109, 1985.
Jackson, "Renal action of purines," In: *Purinergic Approches in Experimental Therapeutics*, Eds., Jacobson, K. A. and Jarvis, M. F. Wiley-Liss Inc., New York, pp. 217–250, 1997.
Jacobson, Jarvis, *Purinergic Approches in Experimental Therapeutics*, Wiley-Liss Inc., New York, 1997.
Jacobson et al., *Med. Chem.*, 32:1043–1051, 1989.
Jakobovits et al., *Mol. Cell. Biol.*, 8:2555, 1988.
Jameel and Siddiqui, *Mol. Cell. Biol.*, 6:710, 1986.
Janusz et al., *Brain Research*, 567:181–187, 1991.
Jarvis et al., *J. Pharma. Exp. Therap.*, 251:888–893, 1989.
Jaynes et al., *Mol. Cell. Biol.*, 8:62, 1988.
Johnson et al., *Mol. Cell. Biol.*, 9:3393, 1989.
Johnson et al., In: *Biotechnology and Pharmacy*, Pezzuto et al., eds., Chapman and Hall, New York, 1993.
Jones and Shenk, *Cell*, 13:181–188, 1978.
Kadesch and Berg, *Mol. Cell. Biol.*, 6:2593, 1986.
Kaminska and Fox, *J. Lab. Clin. Med.* 96:141–147, 1980.
Kaneda et al., *Science*, 243:375–378, 1989.
Kaplitt et al., *Nature Genetics*, 8:148–154, 1994.
Karin et al., *Mol. Cell. Biol.*, 7:606, 1987.
Karlsson et al., *EMBO J.*, 5:2377–2385, 1986.
Kasahara et al., *Science*, 266:1373–1376, 1994.
Katinka et al., *Cell*, 20:393, 1980.
Katinka et al., *Nature*, 290:720, 1981.
Kato et al., *J. Biol. Chem.*, 266:3361–3364, 1991.
Kaufman, *Methods in Enzymology*, 185:537–566, 1990.
Kawamoto et al., *Mol. Cell. Biol.*, 8:267, 1988.
Kelleher and Vos, *Biotechniques*, 17(6):1110–1117, 1994.
Kiledjian et al., *Mol. Cell. Biol.*, 8:145, 1988.
Klamut et al., *Mol. Cell Biol.*, 10:193, 1990.
Klein et al., *Nature*, 327:70–73, 1987.
Knudsen, Blackburn, Chinskey, Airhart and Kellems, *Biol. Reprod.* 44:171–184, 1991.
Knudsen, Winters, Otey, Blackburn, Airhart and Kellems, *Teratology* 45:91–103, 1992.
Koch et al., Mol. Cell. Biol., 9:303, 1989.
Kohno, Ji, Mawhorter, Koshiba and Jacobson, "Activation of A3 adenosine receptors on human eosinophils elevates intercellular calcium," *Blood* 88:3569–3574, 1996.
Kotin et al., *Proc. Natl. Acad. Sci. USA*, 87:2211–2215, 1990.
Kozak, *J. Biol. Chem.*, 266:19867–19870, 1991.
Kriegler and Botchan, In: *Eukaryotic Viral Vectors*, Y. Gluzman, ed., Cold Spring Harbor: Cold Spring Harbor Laboratory, N.Y., 1982.
Kriegler and Botchan, *Mol. Cell. Biol.*, 3:325, 1983.
Kriegler et al., *Cell*, 38:483, 1984a.
Kriegler et al., *Cell*, 53:45, 1988.
Kriegler et al., In: *Cancer Cells 2/Oncogenes and Viral Genes,* Van de Woude et al. eds, Cold Spring Harbor, Cold Spring Harbor Laboratory, 1984b.
Kriegler et al., In: *Gene Expression*, D. Hamer and M. Rosenberg, eds., New York: Alan R. Liss, 1983.
Kuhl et al., *Cell*, 50:1057, 1987.
Kung, Stelts, Zurcher, Jones, Umland, Kretner, Egan and Chapman, "Mast cells modulate allergic pulmonary eosinophilia in mice," *Am. J. Respir. Cell Mol. Biol.* 12:404–409, 1995.
Kunkel et al., *Methods Enzymol.*, 154:367–382, 1987.
Kunz et al., *Nucl. Acids Res.*, 17:1121, 1989.
Kyte and Doolittle, *J. Mol. Biol.*, 157(1):105–132, 1982.
LaFace et al., *Viology*, 162:483–486, 1988.
Laitinen, Heino, Laitinen, Kava and Haahtela, "Damage of the airway epithelium and bronchial reactivity in patients with asthma," *Am. Rev. Respir. Dis.* 131:599–606, 1985.
Lakso et al., *Proc. Nat. Acad. Sci. USA*, 93:5860–5865, 1996.
Larsen et al., *Proc. Natl. Acad. Sci. USA*, 83:8283, 1986.
Larsen and Colasurdo, *Animal Models of Asthma: The Lung Scientific Foundation.* Second Edition. R G Crystal, J B West, E R Weibel, P J Barnes. Raven Press, New York, 1315–1331, 1997.
Larsson and Litwin, *Dev. Biol. Standard.*, 66:385–390, 1987.
Laspia et al., *Cell*, 59:283, 1989.
Latimer et al., *Mol. Cell. Biol.*, 10:760, 1990.
Laughlin et al., *J. Virol.*, 60:515–524, 1986.

Lauzon and Bates, "Estimation of tyme-varying respiratory mechanical parameters by recursive least squares," *J. Appl. Physiol.* 71:1159–1165, 1991.

Le Gal La Salle et al., *Science,* 259:988–990, 1993.

Lebkowski et al., *Mol. Cell. Biol.,* 8:3988–3996, 1988.

Ledent, Vaugeois, Schiffmann, Pedrazzini, Yacoubi, Vanderhaeghen, Costentin, Heath, Vassart and Parmentier, "Aggressiveness, hypoalgesia and high blood pressure in mice lacking the adenosine $A_{2a}$ receptor, " *Nature* 388:674–678, 1997.

Lee et al., *Nature,* 294:228, 1981.

Lee et al., "Interleukin-5 expression in the lung epithelium of transgenic mice leads to pulmonary changes pathognomonic of asthma," *J. Exp. Med.,* 185:2143–2156, 1997.

Levinson et al., *Nature,* 295:79, 1982.

Levrero et al., *Gene,* 101:195–202, 1991.

Libert, Parmentier, Lefort, Dinsart, VanSande, Maenhaut, Simons, Dumont and Vassart, "Selective amplification and cloning of four new members of the G protein-coupled receptor family," *Science* 244:569–572, 1989.

Lilly, Nakamura, Kesselman, Nagler-Anderson, Asano, Garcia-Zepeda, Rothenberg, Drazen and Luster, "Expression of eotaxin by human lung epithelial cells: induction by cytokines and inhibition by glucocorticoids," *J. Clin. Invest.* 99:1767–1773, 1997.

Lin et al., *Mol. Cell. Biol.,* 10:850, 1990.

Linden, "Structure and function of A1 adenosine receptors," *FASEB* 5:2668–2676, 1991.

Long, Mcbride, Hall, "Sequelae of respiratory syncytial virus infections," *Am. J. Reespir. Crit. Care Med.* 151:1678–1681, 1995.

Luo et al., *Blood,* 82(Supp.):1,303A, 1994.

Luria et al., *EMBO J.,* 6:3307, 1987.

Lusky and Botchan, *Proc. Natl. Acad. Sci. USA,* 83:3609, 1986.

Lusky et al., *Mol. Cell. Biol.,* 3:1108, 1983.

Maeser and Kahlmann, *Mol. Gen. Genetics,* 230:170–176, 1991.

Majors and Varmus, *Proc. Natl. Acad. Sci. USA,* 80:5866, 1983.

Malanchere, Huetz and Coutinho *Eur. J. Immunol* 27, 788–793, 1997.

Mann et al., *Cell,* 33:153–159, 1983.

Mann, Holgate, Renwick and Cushley, "Airway effects of purine nucleosides and nucleotides and release with bronchial provocation in asthma," *J. Appl. Physiol.* 61:1667–1676, 1986.

Markowitz et al., *J. Virol.,* 62:1120–1124, 1988.

Marquardt, "Adenosine," In: *Asthma.* Vol 1. eds., Barnes, P. J. , Grunstein, M. M., Leff, A. R. and Woolcock, A. J. Lippincott-Raven, Philadelphia, Pa. pp. 585–591, 1997.

Marquart, Gruber, Wasserman, "Adenosine relaese from stimulated mast cells," *Proc. Ntl. Acad. Sci.* 81:6192–6196, 1984.

Marquart, Parker, Sullivan, "Potentiation of mast cell mediator release by adenosine," *J. Immunol.* 120:871–878, 1978.

Martinez, "Viral infections and the development of asthma," Am. J. Respir. Crit. Care Med. 151:1644–1648, 1995.

Mattoli, Stacey, Sun, Bellini, Marini, "Eotaxin expression and eosinophilic inflammation in asthma," *Biochem. Biophys. Res. Commun.* 236:299–301, 1997.

McCarty et al., *J. Virol.,* 65:2936–2945, 1991.

McLaughlin et al., *J. Virol.,* 62:1963–1973, 1988.

McNeall et al., *Gene,* 76:81, 1989.

Mentzer, Rubio, Berne, "Release of adenosine by hypoxic canine lung tissue and its possible role in pulmonary circulation," *Am. J. Physiol.* 229:1625–1632, 1975.

Michael, *Biotechniques,* 16:410–412, 1994.

Migchielsen et al. "Adenosine-deaminase-deficient mice die perinatally and exhibit liver-cell degeneration, atelectasis and small intestine cell death," *Nature Genet.* 10:279–287, 1995.

Miksicek et al., *Cell,* 46:203, 1986.

Mizrahi, *Process Biochem., (August):*9–12, 1983.

Mordacq and Linzer, *Genes and Dev.,* 3:760, 1989.

Moreau et al., *Nucl Acids Res.,* 9:6047, 1981.

Morgan, Levinsky, Hugh, Fairbanks, Morris, Simmonds, *Clin. Exp. Immunol.* 70:491–499, 1987.

Munoz et al., *Eur. Heart J.,* 5:735–738, 1984.

Murray, Churchill *J. Pharmacol. Exp. Therap.,* 232:189–193, 1985.

Musesing et al., *Cell,* 48:691, 1987.

Muzyczka, *Curr. Top. Microbiol. Immunol.,* 158:97–129, 1992.

Nadel, Holtzman, "Regulation of airway responsiveness and secretion: the role of inflammation," In: Asthma: physiology, immunopathology, and treatment. eds., Kay, A. B., Austen, K. F. and Lichtenstein, L. M. Academic Press, London, pp 129–155, 1984.

Najar, Ruhl, Bru-Capdeville, Peters, "Adenosine and its derivatives control human monocyte differentiation into highly accessory cells versus macrophages," *J. Leuk. Biol.* 47:429–439, 1990.

Nakajima, Iwamot, Tomoe, Matsumura, Tomioka, Takatsu, Yoshida, "CD4+ T-lymphocytes and interleukin-5 mediate antigen-induced eosinophil infiltartion into the mouse trachea," *Am. Rev. Respir. Dis.* 146:374–377, 1992.

National Heart, Lung, and Blood Institute National asthma Education Program. "Expert Panel report: guidelines fro the diagnosis and management of asthma," *J. All. Clin. Immunol* 88:425–534, 1991.

Ng et al., *Nuc. Acids Res.,* 17:601, 1989.

Nicolas and Rubinstein, In: *Vectors: A survey of molecular cloning vectors and their uses,* Rodriguez and Denhardt (eds.), Stoneham: Butterworth, 494–513, 1988.

Nicolau and Sene, *Biochim. Biophys. Acta,* 721:185–190, 1982

Nicolau et al., *Methods Enzymol.,* 149:157–176, 1987.

Nilsson and Mosbach, *Dev. Biol. Standard.,* 66:183–193, 1987.

Nyce, Metzger, "DNA antisense therapy for asthma in an animal model," Nature 385:721–725, 1997.

Oettinger et al., *Science,* 248:1517–1523, 1990.

Ohi et al., *Gene,* 89L:279–282, 1990.

Olah, Stiles, "Adenosine receptor subtypes: characterization and therapeutic regulation," *Ann. Rev. Pharmacol. Tox.* 35:581–606, 1995.

Olsson, *Ann. Rev. Physiol,* 43:385–395, 1981.

Ondek et al., *EMBO J.,* 6:1017, 1987.

Onouchi et al., *Mol. Cell. Biol.,* 247:653–660, 1995.

Ornitz et al., *Mol. Cell. Biol.,* 7:3466, 1987.

Palmiter et al., *Cell,* 29:701, 1982.

Palmiter et al., *Nature,* 300:611, 1982.

Paskind et al., *Virology,* 67:242–248, 1975.

Pech et al., *Mol. Cell. Biol.,* 9:396, 1989.

Perales et al., *Proc. Natl. Acad. Sci. USA,* 91:4086–4090, 1994.

Perez-Stable and Constantini, *Mol. Cell. Biol.,* 10:1116, 1990.

Petricciani, *Dev. Biol. Standard,* 66:3–12, 1985.

Pfeffer et al., *Cell,* 73:457–467, 1993.

Phillips et al., In: *Large Scale Mammalian Cell Culture,* Feder and Tolbert, eds., Academic Press, Orlando, Fla, USA, 1985.

Picard and Schaffner, *Nature*, 307:83, 1984.

Pierce, Furlong, Selbie and Shine, "Molecular cloning and expression of an adenosine A2b receptor from human brain," *BBRC* 187:86–93, 1992.

Pinkert et al., *Genes and Dev.*, 1:268, 1987.

Platts-Mills and Chapman, "Dust mite: immunology, allergic disease and environmental control," *J. All. Clin. Immunol.* 80:755–775, 1987.

Platts-Mills, Tovey, Mitchell, Mszoro, Nock and Wilkins, "Reduction of bronchila hyperreactivity during prolonged allergen avoidance, " *Lancet,* 675–678, 1982.

Ponta et al., *Proc. Natl. Acad. Sci. USA.*, 82:1020, 1985.

Porton et al., *Mol. Cell. Biol.*, 10:1076, 1990.

Potter et al., *Proc. Natl. Acad. Sci. USA,* 81:7161–7165, 1984.

Prince and Porter, "The pathogenesis of respiratory syncytial virus in infant ferrets," *Am. J. Pathol.* 82:339–352, 1976.

Prince, Horswood, Berndt, Suffin and Chanock, "Respiratory syncytial virus infection in inbred mice," *Infect. Immunity* 26:764–766, 1979.

Queen and Baltimore, *Cell,* 35:741, 1983.

Quinn et al., *Mol. Cell. Biol.*, 9:4713, 1989.

Racher et al., *Biotechnology Techniques,* 9:169–174, 1995.

Ragot et al., *Nature,* 361:647–650, 1993.

Ratech, Greco, Gallo, Rimoin, Kamino and Hirschhorn, *Am. J. Pathol.* 120:157–169, 1985.

Ratech, Thorbecke and Hirschhorn, *Clin. Immunol. Immunopath.* 21:119–127, 1981.

Ratter, Germer, Fischbach, Schulze-Osthoff, Peter, Droge, Krammer and Lehmann, *Int. Immunol.* 8:1139–1147, 1996.

Redondo et al., *Science,* 247:1225, 1990.

Reeves, Jones, Sheehan, Vardey and Whelan, "Adenosine $A_3$ receptors promote d3egranulation of rat mast cells both in vitro and in vivo, " *Inflamm. Res.* 46:180–184, 1997.

Reisman and Rotter, *Mol. Cell. Biol.,* 9:3571, 1989.

Renan, *Radiother. Oncol.,* 19:197–218, 1990.

Renz, Smith, Henson, Ray, Irvin, Gelfand, "Aerosolized antigen exposure without adjuvant causes increased IgE production and increased airway responsiveness in the mouse," *J. All. Clin. Immunol.* 89:1127–1138, 1992.

Resendez Jr. et al., *Mol. Cell. Biol.*, 8:4579, 1988.

Rich et al., *Hum. Gene Ther.,* 4:461476, 1993.

Richardson, "Blocking adenosine with antisense," *Nature* 385:684–685, 1997.

Ridgeway, In: *Vectors: A survey of molecular cloning vectors and their uses.* Rodriguez and Denhardt, eds., Stoneham: Butterworth, 467–492, 1988.

Ripe et al., *Mol. Cell. Biol.,* 9:2224, 1989.

Rippe et al., *Mol. Cell Biol.,* 10:689–695, 1990.

Rittling et al., *Nucl. Acids Res.,* 17:1619, 1989.

Rivkees and Reppert, "RFL9 Encodes an A2b-adenosine receptor," *Mol. Endocrinol.* 6:1598–1604, 1992.

Robertson, In: *Teratocarcinomas and Embryonic Stem Cells: A Practical Approach,* E. J. Robertson, ed., IRL Press, Washington, D.C., 1987.

Rosen et al., *Cell,* 41:813, 1988.

Rosenfeld et al., *Cell,* 68:143–155, 1992.

Rosenfeld et al., *Science,* 252:431–434, 1991.

Rothenberg, MacLean, Pearlman, Luster and Leder, "Targeted disruption of the chemokine eotaxin partially reduces antigen-induced tissue eosinophilia," *J. Exp. Med.* 185:785–790, 1997.

Roux et al., *Proc. Natl. Acad. Sci. USA,* 86:9079–9083, 1989.

Sakai et al., *Genes and Dev.,* 2:1144, 1988.

Salvatore, Jacobson, Taylor, Linden and Johnson, "Molecular cloning and characterization of the human $A_3$ adenosine receptor, " *Proc. Natl. Acad. Sci. USA* 90:10365–10369, 1993.

Sambrook et al., In: *Molecular Cloning: A Laboratory Manual,* 2nd Ed., Cold Spring Harbor Press, Cold Spring Harbor, N.Y., 1989.

Samulski et al., *EMBO J.,* 10:3941–3950, 1991.

Samulski et al., *J. Virol,* 63:3822–3828, 1989.

Santerre et al., *Gene,* 30:147, 1984.

Satake et al., *J. Virology,* 62:970, 1988.

Sauer, *Methods in Enzymology,* 225:890–900, 1993.

Sauer, *Mol. Cell. Biol.,* 7:2087–2096, 1987.

Schaffner et al., *J. Mol. Biol.,* 201:81, 1988.

Schatz et al., *Cell,* 59:1035–1048, 1989.

Schutz, Schrader and Gerlach, "Different sites of adenosine formation in the heart," *Am. J. Physiol* 240:H963–970, 1981.

Schwarze, Hamelmann, Bradely, Takeda and Gelfand, "Respiratory syncytial virus infection results in airway hyper-responsiveness and enhanced airway sensitization to allergen," *J. Clin. Invest.* 99:226–233, 1997.

Searle et al., *Mol. Cell. Biol.,* 5:1480, 1985.

Sears, Burrows, Flannery, Herbison, Hewitt and Holdaway, "Association of asthma with serum IgE and skin test reactivity to allergens," *N. Engl. J. Med.* 320:271–277, 1991.

Seto, Carrera, Kubota, Wasson and Carson, *J. Clin. Invest.* 75:377–383, 1985.

Sharp and Marciniak, *Cell,* 59:229, 1989.

Shaul and Ben-Levy, *EMBO J.,* 6:1913, 1987.

Shelling and Smith, *Gene Therapy.* 1:165–169, 1994.

Sherman et al., *Mol. Cell. Biol.,* 9:50, 1989.

Shi, Winston, Blackburn, Datta, Hanten and Kellems, *J. Biol. Chem.* 272:2334–2341, 1997.

Shijubo, Shigehara, Hirasawa, Inuzuka and Abe, "Eosinophilic cationic protein in chronic eosinophilic pneumonia and eosinophilic granuloma," *Chest,* 106:1481–1486, 1994.

Sigurs, Bjarnason, Sigurbergson, Kjellman, and Biorksten, "Asthma and immunoglulin E antibodies after respiratory syncytial virus bronchiolitis: a prospective cohort study with matched controls," *Pediatrics* 95:500–505, 1995.

Sleigh and Lockett, *J. EMBO,* 4:3831, 1985.

Spalholz et al., *Cell,* 42:183, 1985.

Spandau and Lee, *J. Virology,* 62:427, 1988.

Spandidos and Wilkie, *EMBO J.,* 2:1193, 1983.

Stehle, Scott, Lee, Weaver, Deeds and Reppert, "Molecular cloning and expression of the cDNA for a novel A2-adenosine receptor subtype," *Mol. Endocrinol.* 6:384–393, 1992.

Stephens and Hentschel, *Biochem. J.,* 248:1, 1987.

Strek and Leff, Eosinophils. In: *Asthma. Vol* 1. eds., Barnes, P. J. , Grunstein, M. M., Leff, A. R. and Woolcock, A. J. Lippincott-Raven, Philadelphia, Pa. pp. 399–417, 1997.

Sternberg and Hamilton, *J. Mol. Biol.,* 150:467–486, 1981.

Sternberg et al., *J. Mol. Bio.,* 187:197–212, 1986.

Stiles, "Adenosine receptors," *J. Biol. Chem.* 267:6451–6454, 1992.

Stratford-Perricaudet and Perricaudet, In: *Human Gene Transfer,* Eds, Cohen-Haguenauer and Boiron, Editions John Libbey Eurotext, France, 51–61, 1991.

Stratford-Perricaudet et al., *Hum. Gene. Ther.,* 1:241–256, 1991.

Stuart et al., *Nature,* 317:828, 1985.

Sullivan and Peterlin, *Mol. Cell. Biol.,* 7:3315, 1987.

Swartzendruber and Lehman, *J. Cell. Physiology,* 85:179, 1975.

Takebe et al., *Mol. Cell. Biol.,* 8:466, 1988.

Tang, Geba, Zheng, Ray, Holmer, Kuhn, Flavell and Elias, "Targeted expression of IL-11 in the murine airway causes lymphocytic inflammation, bronchial remodeling and airway obstruction," *J. Clin. Invest.* 98:2845–2853, 1996.

Tavernier et al., *Nature,* 301:634, 1983.

Taylor et al., *FASEB J.,* 2:1799, 1988.

Taylor and Kingston, *Mol. Cell. Biol.,* 10:165, 1990a.

Taylor and Kingston, *Mol. Cell. Biol.,* 10:176, 1990b.

Taylor et al., *J. Biol. Chem.,* 264:15160, 1989.

Temin, In: *Gene Transfer,* Kucherlapati, ed., New York: Plenum Press, 149–188, 1986.

Ten Have-Opbroek, "Lung development in the mouse embryo," *Exp. Lung Res.* 17:111–130, 1991.

Teran, Noso, Carroll, Davies, Holgate and Schroder, "Eosinophil recruitment following allergen challenge is associated with the release of the chemokine RANTES into asthmatic airways," *J. Immunol.* 157:1806–1812, 1996.

Thiesen et al., *J. Virology,* 62:614, 1988.

Tomic et al., *Nucl. Acids Res.,* 12:1656, 1990.

Top et al., *J. Infect. Dis.,* 124:155–160, 1971.

Tratschin et al., *Mol. Cell. Biol.,* 4:2072–2081, 1984.

Tratschin et al., *Mol. Cell. Biol.,* 5:32581–3260, 1985.

Treisman, *Cell,* 42:889, 1985.

Tronche et al., *Mol. Biol. Med.,* 7:173, 1990.

Tronche et al., *Mol. Cell. Biol.,* 9:4759, 1989.

Trudel and Constantini, *Genes and Dev.,* 6:954, 1987.

Tur-Kaspa et al., *Mol. Cell Biol.,* 6:716–718, 1986.

Tyndall et al., *Nuc. Acids. Res.,* 9:6231, 1981.

Ullman, Gudas, Cohen and Martin, Jr., *Cell* 14:365–375, 1978.

Ullman, Levinson, Hershfield and Martin, Jr., *J. Biol. Chem.* 256:848–852, 1989.

Upender et al., *Biotechniques,* 18:29–31, 1995.

Van Caulker, Muller, Hamprecht, *J. Neurochem.,* 33:999–1003,1979.

Van Wezel, *Nature,* 216:64–65, 1967.

Vannice and Levinson, *J. Virology,* 62:1305, 1988.

Vasseur et al., *Proc. Natl. Acad. Sci. USA.,* 77:1068, 1980.

Von Lubitz et al., *Stroke,* 19:1133, 1988.

Vogel, *New clues to asthma therapies, Science,* 276:1643–1646, 1997.

Wada et al., *Nucleic Acids Res.,* 18:2367–2411, 1990.

Wagner et al., *Science,* 260:1510–1513, 1990.

Wakamiya, Blackburn, Jurecic, McArthur, Geske, Cartwright, Mitani, Vaishnav, Belmont, Kellems, Finegold and Caskey, *Proc. Natl. Acad. Sci. USA* 92:3673–3677, 1995.

Walker, "Effects of adenosine on guinea pig pulmonary eosinophils," *Inflamm.* 20:11–21, 1996.

Walsh et al., *J. Clin. Invest.,* 94:1440–1448, 1994.

Wan, Sutherland, Geiger, *J. Neurochem.,* 55:1763–1771, 1990.

Wang and Calame, *Cell,* 47:241, 1986.

Wardlaw, Dunnette, Gleich, Collins and Kay, "Eosinophils and mast cells in bronchoalveolar lavage in subjects with mild asthma " *Am. Rev. Respir. Dis.* 137:62–69, 1988.

Watson et al., In: *Molecular Biology of the Gene,* 4th Ed., W. A. Benjamin, Inc., Menlo Park, Calif., 1987.

Weber et al., *Cell,* 36:983, 1984.

Wei et al., *Gene Therapy,* 1:261–268, 1994.

Weinberger et al. *Mol. Cell. Biol.,* 8:988, 1984.

Weiss, Gergen and Hodgson, "A economic evaluation of asthma in the United States," *N. Engl. J. Med.* 326:862–866, 1992.

Weiss, Tager, Munoz and Speizer, "The relationship of respiratory infections in early childhood to the occurrence of increased levels of bronchial responsiveness and atopy," *Am. Rev. Respir. Dis.* 131:573–578, 1985.

Welliver, Wong, Sun, Middleton, Vaughn and Ogra, "The development of RSV specific IgE and release of histamine in nasopharyngeal secretion after infection," *N. Engl. J. Med.* 305:841–846, 1981.

Wiginton et al., *Biochemistry,* 25 (25): 8234–8244, 1986.

Wigley et al., *Reprod. Fertil. Dev.,* 6:585–588, 1994.

Winoto and Baltimore, *Cell,* 59:649, 1989.

Winston et al., *J. Biol. Chem.,* 267:13472–13479, 1992.

Wong et al., *Gene,* 10:87–94, 1980.

Wu and Wu, *Adv. Drug Delivery Rev.,* 12:159–167, 1993.

Wu and Wu, *J. Biol. Chem.,* 262:4429–4432, 1987.

Yang et al., *J. Virol.,* 68:4847–4856, 1994.

Yang et al., *Proc. Nat'l Acad. Sci. USA,* 87:9568–9572, 1990.

Yoder et al., *Blood,* 82 (Supp.):1 :347A, 1994.

Yu and Chang, "Submicron polymer membrane hemoglobin nanocapsules as potential blood substitutes: preparation and characterization," *Artif. Cells Blood Substit. Immobil. Biotechnol.,* 24(3): 169–183, 1996.

Yutzey et al. *Mol. Cell. Biol.,* 9:1397, 1989.

Zhang, Lamm, Albert, Chi, Henderson and Lewis, "Influence of the route of allergen administration and genetic background on the murine allergic pulmonary response," *Am. J. Respir. Crit. Care Med.* 155:661–669, 1997.

Zhou et al., *Exp. Hematol. (NY)* 21:928–933, 1993.

Zhou, et al., *J. Exp. Med.,* 179:1867–1875, 1994.

Zhou, Li, Olah, Johnson, Stiles and Civelli, "Molecular cloning and characterization of an adenosine receptor: the A3 adenosine receptor," *Proc. Ntl. Acad. Sci.* 89:7432–7438, 1992.

Zimmermann, "5'-Nucleotidase: molecular structure and functional aspects," *Biochem. J.* 285:345–365, 1992.

---

What is claimed is:

1. A transgenic mouse that is homozygous for a null allele of its endogenous ADA gene, wherein:
   a) the genome of said transgenic mouse comprises a transgene comprising a mouse ADA encoding region operably coupled to a mouse placental specific ADA promoter,
   b) said ADA transgene is expressed during fetal development,
   c) there is substantially no ADA activity present in said mouse after birth, and
   d) said transgenic mouse exhibits a pulmonary abnormality after birth.

2. The mouse of claim 1, preparable by:
   crossing a first mouse comprising the transgene comprising a mouse placental-specific ADA transgene with a second mouse heterozygous for a null Ada allele to obtain a third mouse comprising the transgene and the null Ada allele; and
   crossing the third mouse with a fourth mouse to produce a fifth mouse that comprises the placental-specific ADA transgene and is homozygous for the null Ada allele.

3. The mouse of claim 1, wherein said pulmonary abnormalities mimic those exhibited in human asthma.

4. A transgenic mouse that is homozygous for a null allele of its endogenous ADA gene comprises a transgene comprising a mouse ADA encoding region operably coupled to a mouse placental specific ADA promoter, wherein ADA is present in said mouse during fetal development but substantially no endogenous ADA expression is present after birth, said mouse further characterized as exhibiting pulmonary abnormalities after birth.

5. The mouse of claim 4, comprising the transgene comprising a mouse placental-specific ADA transgene that is homozygous for a null Ada allele.

6. The mouse of claim 5, wherein the transgene comprising a mouse placental-specific ADA transgene is expressed at a developmental stage during fetal development.

7. The mouse of claim 6, wherein the transgene comprising a mouse placental-specific ADA transgene is expressed in trophoblasts during development.

8. The mouse of claim 4, wherein said pulmonary abnormalities mimic those exhibited in human asthma.

9. A method of producing a transgenic mouse that is homozygous for a null allele of its endogenous ADA gene comprises a transgene comprising a mouse ADA encoding region operably coupled to a mouse placental specific ADA promoter, wherein ADA is present in said mouse during fetal development but substantially no endogenous ADA expression is present after birth and said mouse is further characterized as exhibiting pulmonary abnormalities, comprising:
   crossing a first mouse comprising a transgene comprising a mouse placental-specific ADA transgene with a second mouse heterozygous for null Ada allele to obtain a third mouse comprising the transgene and the null Ada allele; and
   crossing the third mouse with a fourth mouse to produce a fifth mouse that comprises the transgene comprising a mouse placental-specific ADA transgene and is homozygous for the null Ada allele.

10. The method of claim 9, wherein the transgene comprising a mouse placental-specific ADA transgene is expressed at a developmental stage during the fetal development of the fifth mouse.

11. The method of claim 10, wherein the transgene comprising a mouse placental-specific ADA transgene is expressed in trophoblasts during development of the fifth mouse.

12. The method of claim 9, wherein the fourth mouse is heterozygous for a null Ada allele.

13. The method of claim 9, wherein the fifth mouse is homozygous for a null Ada allele.

14. The method of claim 13, wherein the fourth mouse comprises the transgene comprising a mouse placental-specific ADA transgene.

15. The method of claim 11, wherein said pulmonary abnormalities mimic those exhibited in human asthma.

* * * * *

UNITED STATES PATENT AND TRADEMARK OFFICE
CERTIFICATE OF CORRECTION

| | |
|---|---|
| PATENT NO. | : 6,207,876 B1 |
| APPLICATION NO. | : 09/301665 |
| DATED | : March 27, 2001 |
| INVENTOR(S) | : Rodney E. Kellems et al. |

It is certified that error appears in the above-identified patent and that said Letters Patent is hereby corrected as shown below:

In column 1, lines 9-14, delete
"The government owns rights in the present invention pursuant to grant number AI43572, DK46207, HD34130, HD07843 and HL61888 from the National Institutes of Health as well as grant number 011618-060 from the Texas Higher Education Coordinating Board Applied Technology Grant." and insert
--This invention was made with government support under Grant Nos. DK46207 and HD34130 awarded by the National Institutes of Health. The government has certain rights in the invention--.

Signed and Sealed this
Twentieth Day of March, 2012

David J. Kappos
*Director of the United States Patent and Trademark Office*